US009439857B2

(12) United States Patent
Tamarkin et al.

(10) Patent No.: US 9,439,857 B2
(45) Date of Patent: Sep. 13, 2016

(54) FOAM CONTAINING BENZOYL PEROXIDE

(75) Inventors: Dov Tamarkin, Ness Ziona (IL);
Doron Friedman, Karmei Yosef (IL);
David Schuz, Moshav Gimzu (IL);
Rita Keynan, Rehovot (IL); Tal Berman, Rishon Lezion (IL); Jorge Danziger, Rishom Lezion (IL)

(73) Assignee: Foamix Pharmaceuticals Ltd., Rehovot (IL)

( * ) Notice: Subject to any disclaimer, the term of this patent is extended or adjusted under 35 U.S.C. 154(b) by 631 days.

(21) Appl. No.: 12/745,417

(22) PCT Filed: Dec. 1, 2008

(86) PCT No.: PCT/IB2008/003908
§ 371 (c)(1),
(2), (4) Date: Nov. 9, 2010

(87) PCT Pub. No.: WO2009/069006
PCT Pub. Date: Jun. 4, 2009

(65) Prior Publication Data
US 2011/0045037 A1 Feb. 24, 2011

Related U.S. Application Data

(60) Provisional application No. 61/004,838, filed on Nov. 30, 2007.

(51) Int. Cl.
| | | |
|---|---|---|
| *A61K 31/19* | (2006.01) | |
| *A61K 31/7056* | (2006.01) | |
| *A61K 47/12* | (2006.01) | |
| *A61K 9/12* | (2006.01) | |
| *A61K 8/04* | (2006.01) | |
| *A61K 8/38* | (2006.01) | |
| *A61K 9/00* | (2006.01) | |
| *A61Q 19/00* | (2006.01) | |

(52) U.S. Cl.
CPC ............. *A61K 9/122* (2013.01); *A61K 8/046* (2013.01); *A61K 8/38* (2013.01); *A61K 9/0014* (2013.01); *A61K 31/19* (2013.01); *A61K 31/7056* (2013.01); *A61K 47/12* (2013.01); *A61Q 19/008* (2013.01)

(58) Field of Classification Search
CPC ...... A61K 9/122; A61K 47/10; A61K 47/12; A61K 8/046; A61K 9/0014; A61K 31/19; A61K 31/7056; A61K 8/34; A61K 31/196; A61K 31/506; A61K 31/522; A61K 31/573; A61K 31/60; A61K 47/24; A61K 47/36; A61K 2300/00; A61K 31/65; A61K 9/12; A61K 45/06; A61K 47/06; A61K 47/44; A61K 31/192; A61K 47/14; A61K 8/342
See application file for complete search history.

(56) References Cited

U.S. PATENT DOCUMENTS

| | | |
|---|---|---|
| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |

(Continued)

FOREIGN PATENT DOCUMENTS

| | | |
|---|---|---|
| AU | 198780257 | 9/1986 |
| CA | 2114537 | 2/1993 |

(Continued)

OTHER PUBLICATIONS

U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
"Burn patients need vitamin D supplements." *Decision News Media*, Jan. 23, 2004, http://www.nutraingredients.com/Research/Burn-patients-need-vitamin-D-supplements, Accessed: May 5, 2010.
"HLB Systems", http://pharmcal.tripod.com/ch17.htm, Accessed Sep. 17, 2010, pp. 1-3.

(Continued)

*Primary Examiner* — Audrea Buckley
(74) *Attorney, Agent, or Firm* — Fish & Richardson P.C.

(57) ABSTRACT

The present invention relates to foamable compositions for treating acne comprising benzoyl peroxide; to a therapeutic kit comprising such compositions; and to a method of treating acne using such compositions.

40 Claims, 15 Drawing Sheets

(56) References Cited

U.S. PATENT DOCUMENTS

| | | |
|---|---|---|
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Shoemaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,627,973 A | 12/1986 | Moran et al. |
| 4,628,063 A | 12/1986 | Haines et al. |
| 4,661,340 A | 4/1987 | Nagy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |

(56) References Cited

U.S. PATENT DOCUMENTS

| | | |
|---|---|---|
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |

(56) References Cited

U.S. PATENT DOCUMENTS

| | | |
|---|---|---|
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Heinkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |

(56) References Cited

U.S. PATENT DOCUMENTS

| | | |
|---|---|---|
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,192,749 B2 | 6/2012 | Ashley |
| 8,211,874 B2 | 7/2012 | Theobald et al. |
| 8,592,380 B2 | 11/2013 | Trumbore et al. |
| 8,623,330 B2 | 1/2014 | Gurge et al. |
| 8,652,443 B2 | 2/2014 | Varanasi et al. |
| 8,735,377 B1 | 5/2014 | Sipos |
| 8,784,780 B2 | 7/2014 | Gurge et al. |
| 8,795,693 B2 | 8/2014 | Tamarkin et al. |
| 8,846,039 B2 | 9/2014 | Chung et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,992,896 B2 | 3/2015 | Tamarkin et al. |
| 9,050,253 B2 | 6/2015 | Tamarkin et al. |
| 9,101,662 B2 | 8/2015 | Tamarkin et al. |
| 9,192,558 B2 | 11/2015 | Chen et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0064541 A1* | 5/2002 | Lapidot et al. ............ 424/401 |

(56) References Cited

U.S. PATENT DOCUMENTS

| | | |
|---|---|---|
| 2002/0072544 A1 | 6/2002 | Miller et al. |
| 2002/0090386 A1 | 7/2002 | Haslwanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Withiam et al. |
| 2004/0002550 A1 | 1/2004 | Mercurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0258628 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1* | 4/2005 | Tamarkin et al. ............. 424/47 |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1* | 8/2005 | Tamarkin et al. ............. 424/47 |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1* | 11/2006 | Friedman et al. ............. 424/45 |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |

(56) References Cited

U.S. PATENT DOCUMENTS

| | | |
|---|---|---|
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1* | 1/2007 | Tamarkin et al. ............ 424/70.1 |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis et al. |
| 2007/0237724 A1* | 10/2007 | Abram et al. ............... 424/47 |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0041680 A1 | 2/2009 | Tamarkin et al. |
| 2009/0053290 A1 | 2/2009 | Sand et al. |
| 2009/0061001 A1 | 3/2009 | Hougaz |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0214628 A1 | 8/2009 | De Rijk |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0137198 A1 | 6/2010 | Eini et al. |
| 2010/0221194 A1 | 9/2010 | Loupenok |
| 2010/0221195 A1 | 9/2010 | Tamarkin et al. |
| 2010/0266510 A1 | 10/2010 | Tamarkin et al. |
| 2010/0286417 A1 | 11/2010 | Mendes et al. |
| 2011/0002857 A1 | 1/2011 | Tamarkin et al. |
| 2011/0002969 A1 | 1/2011 | Serraima et al. |
| 2011/0008266 A1 | 1/2011 | Tamarkin et al. |
| 2011/0045037 A1 | 2/2011 | Tamarkin et al. |
| 2011/0212033 A1 | 9/2011 | Tamarkin et al. |
| 2011/0262542 A1 | 10/2011 | Ashley |
| 2011/0268665 A1 | 11/2011 | Tamarkin et al. |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0195836 A1 | 8/2012 | Tamarkin et al. |
| 2012/0213709 A1 | 8/2012 | Tamarkin et al. |
| 2012/0213710 A1 | 8/2012 | Tamarkin et al. |
| 2012/0237453 A1 | 9/2012 | Tamarkin et al. |
| 2013/0011342 A1 | 1/2013 | Tamarkin et al. |
| 2013/0028850 A1 | 1/2013 | Tamarkin et al. |
| 2013/0053353 A1 | 2/2013 | Tamarkin et al. |
| 2013/0064777 A1 | 3/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0183250 A1 | 7/2013 | Friedman et al. |
| 2013/0183251 A1 | 7/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0189196 A1 | 7/2013 | Tamarkin et al. |
| 2013/0195769 A1 | 8/2013 | Tamarkin et al. |
| 2013/0225536 A1 | 8/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0050673 A1 | 2/2014 | Tamarkin et al. |
| 2014/0066524 A1 | 3/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0147504 A1 | 5/2014 | Salman et al. |
| 2014/0182585 A1 | 7/2014 | Tamarkin et al. |
| 2014/0186269 A1 | 7/2014 | Tamarkin et al. |
| 2014/0186442 A1 | 7/2014 | Mansouri |
| 2014/0193502 A1 | 7/2014 | Tamarkin et al. |
| 2014/0221320 A1 | 8/2014 | Joks et al. |
| 2014/0227199 A1 | 8/2014 | Tamarkin et al. |
| 2014/0228355 A1 | 8/2014 | Kortagere et al. |
| 2014/0248219 A1 | 9/2014 | Tamarkin et al. |
| 2014/0271494 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0118164 A1 | 4/2015 | Tamarkin et al. |
| 2015/0125496 A1 | 5/2015 | Yamamoto |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0190409 A1 | 7/2015 | Tamarkin et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |

(56) References Cited

U.S. PATENT DOCUMENTS

| | | |
|---|---|---|
| 2016/0101051 A1 | 4/2016 | Tamarkin et al. |
| 2016/0101184 A1 | 4/2016 | Tamarkin et al. |
| 2016/0158261 A1 | 6/2016 | Friedman et al. |

FOREIGN PATENT DOCUMENTS

| | | |
|---|---|---|
| CA | 2154438 | 1/1996 |
| CA | 2422244 | 9/2003 |
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 52404 | 5/1982 |
| EP | 0 156 507 | 10/1985 |
| EP | 0 186 453 | 7/1986 |
| EP | 0 211 550 | 2/1987 |
| EP | 0 213 827 | 3/1987 |
| EP | 0 214 865 | 3/1987 |
| EP | 0 216 856 | 4/1987 |
| EP | 0 270 316 | 6/1988 |
| EP | 0 297 436 | 1/1989 |
| EP | 0 326 196 | 8/1989 |
| EP | 0 336 812 | 10/1989 |
| EP | 0 391 124 | 10/1990 |
| EP | 0 404 376 | 12/1990 |
| EP | 0 414 920 | 3/1991 |
| EP | 0 484 530 | 5/1992 |
| EP | 0 485 299 | 5/1992 |
| EP | 0 488 089 | 6/1992 |
| EP | 0 504 301 | 9/1992 |
| EP | 0 528 190 | 2/1993 |
| EP | 0 535 327 | 4/1993 |
| EP | 0 552 612 | 7/1993 |
| EP | 0 569 773 | 11/1993 |
| EP | 0 598 412 | 5/1994 |
| EP | 0 662 431 | 7/1995 |
| EP | 0 676 198 | 10/1995 |
| EP | 0 738 516 | 10/1996 |
| EP | 0 757 959 | 2/1997 |
| EP | 0 824 911 | 2/1998 |
| EP | 0 829 259 | 3/1998 |
| EP | 0 928 608 | 7/1999 |
| EP | 0 979 654 | 2/2000 |
| EP | 0 993 827 | 4/2000 |
| EP | 1 025 836 | 8/2000 |
| EP | 1 055 425 | 11/2000 |
| EP | 0 506 197 | 7/2001 |
| EP | 1 215 258 | 6/2002 |
| EP | 1 287 813 | 3/2003 |
| EP | 1 308 169 | 5/2003 |
| EP | 1 375 386 | 1/2004 |
| EP | 1 428 521 | 6/2004 |
| EP | 1 438 946 | 7/2004 |
| EP | 1 189 579 | 9/2004 |
| EP | 1 475 381 | 11/2004 |
| EP | 1 483 001 | 12/2004 |
| EP | 1 500 385 | 1/2005 |
| EP | 1 537 916 | 6/2005 |
| EP | 1 600 185 | 11/2005 |
| EP | 1 653 932 | 5/2006 |
| EP | 1 734 927 | 12/2006 |
| EP | 1 758 547 | 3/2007 |
| EP | 1 584 324 | 11/2007 |
| EP | 1 889 609 | 2/2008 |
| EP | 1 902 706 | 3/2008 |
| EP | 2 129 383 | 12/2009 |
| FR | 2 456 522 | 12/1980 |
| FR | 2 591 331 | 6/1987 |
| FR | 2 640 942 | 6/1990 |
| FR | 2 736 824 | 1/1997 |
| FR | 2 774 595 | 8/1999 |
| FR | 2 789 371 | 8/2000 |
| FR | 2 793 479 | 11/2000 |
| FR | 2 814 959 | 4/2002 |
| FR | 2 833 246 | 6/2003 |
| FR | 2 840 903 | 12/2003 |
| FR | 2 843 373 | 2/2004 |
| FR | 2 845 672 | 4/2004 |
| FR | 2 848 998 | 6/2004 |
| FR | 2 860 976 | 4/2005 |
| FR | 2 915 891 | 11/2008 |
| GB | 808 104 | 1/1959 |
| GB | 808 105 | 1/1959 |
| GB | 922 930 | 4/1963 |
| GB | 933 486 | 8/1963 |
| GB | 998 490 | 7/1965 |
| GB | 1 026 831 | 4/1966 |
| GB | 1 033 299 | 6/1966 |
| GB | 1 081 949 | 9/1967 |
| GB | 1 121 358 | 7/1968 |
| GB | 1 162 684 | 8/1969 |
| GB | 1 170 152 | 11/1969 |
| GB | 1 201 918 | 8/1970 |
| GB | 1 347 950 | 2/1974 |
| GB | 1 351 761 | 5/1974 |
| GB | 1 351 762 | 5/1974 |
| GB | 1 353 381 | 5/1974 |
| GB | 1 376 649 | 12/1974 |
| GB | 1 397 285 | 6/1975 |
| GB | 1 408 036 | 10/1975 |
| GB | 1 457 671 | 12/1976 |
| GB | 1 489 672 | 10/1977 |
| GB | 2 004 746 | 4/1979 |
| GB | 1 561 423 | 2/1980 |
| GB | 2 114 580 | 8/1983 |
| GB | 2 153 686 | 8/1985 |
| GB | 2 172 298 | 9/1986 |
| GB | 2 206 099 | 12/1988 |
| GB | 2 166 651 | 5/1996 |
| GB | 2 337 461 | 11/1999 |
| GB | 2 367 809 | 4/2002 |
| GB | 2 406 330 | 3/2005 |
| GB | 2 406 791 | 4/2005 |
| GB | 2 474 930 | 7/2012 |
| IL | 49491 | 9/1979 |
| IL | 152 486 | 5/2003 |
| JP | 60001113 | 4/1978 |
| JP | 55069682 | 5/1980 |
| JP | 57044429 | 3/1982 |
| JP | 56039815 | 4/1984 |
| JP | 61275395 | 12/1986 |
| JP | 62241701 | 10/1987 |
| JP | 63119420 | 5/1988 |
| JP | 1100111 | 4/1989 |
| JP | 1156906 | 6/1989 |
| JP | 2184614 | 7/1990 |
| JP | 2255890 | 10/1990 |
| JP | 4-51958 | 2/1992 |
| JP | 4282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 2008/040899 | 2/1996 |
| JP | 8501529 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |

(56) References Cited

FOREIGN PATENT DOCUMENTS

| | | |
|---|---|---|
| JP | 2000/017174 | 1/2000 |
| JP | 2000/080017 | 3/2000 |
| JP | 2000/128734 | 5/2000 |
| JP | 2000/191429 | 7/2000 |
| JP | 2000/239140 | 9/2000 |
| JP | 2000/351726 | 12/2000 |
| JP | 2000/354623 | 12/2000 |
| JP | 2001/002526 | 1/2001 |
| JP | 2001/019606 | 1/2001 |
| JP | 2001/072963 | 3/2001 |
| JP | 2002/012513 | 1/2002 |
| JP | 2002/047136 | 2/2002 |
| JP | 2002/524490 | 8/2002 |
| JP | 2002/302419 | 10/2002 |
| JP | 2003/012511 | 1/2003 |
| JP | 2003/055146 | 2/2003 |
| JP | 2004/047136 | 2/2004 |
| JP | 2004/250435 | 9/2004 |
| JP | 2004/348277 | 12/2004 |
| JP | 2005/314323 | 11/2005 |
| JP | 2005/350378 | 12/2005 |
| JP | 2006/008574 | 1/2006 |
| JP | 2006/036317 | 2/2006 |
| JP | 2006/103799 | 4/2006 |
| JP | 2006525145 | 11/2006 |
| JP | 2007/131539 | 5/2007 |
| JP | 2007326996 | 12/2007 |
| KR | 143232 | 7/1998 |
| KR | 2001/003063 | 1/2001 |
| RU | 2277501 | 6/2006 |
| UA | 66796 | 6/2004 |
| WO | 82/01821 | 6/1982 |
| WO | 86/05389 | 9/1986 |
| WO | 88/01502 | 3/1988 |
| WO | 88/01863 | 3/1988 |
| WO | 88/08316 | 11/1988 |
| WO | 89/06537 | 7/1989 |
| WO | 90/05774 | 5/1990 |
| WO | 91/11991 | 8/1991 |
| WO | 92/00077 | 1/1992 |
| WO | 92/05142 | 4/1992 |
| WO | 92/05763 | 4/1992 |
| WO | 92/11839 | 7/1992 |
| WO | WO 92/13602 | 8/1992 |
| WO | 93/25189 | 12/1993 |
| WO | 94/06440 | 3/1994 |
| WO | 96/03115 | 2/1996 |
| WO | 96/19921 | 7/1996 |
| WO | 96/24325 | 8/1996 |
| WO | 96/26711 | 9/1996 |
| WO | 96/27376 | 9/1996 |
| WO | 96/39119 | 12/1996 |
| WO | 97/03638 | 2/1997 |
| WO | 97/39745 | 10/1997 |
| WO | 98/17282 | 4/1998 |
| WO | 98/18472 | 5/1998 |
| WO | 98/19654 | 5/1998 |
| WO | 98/21955 | 5/1998 |
| WO | 98/23291 | 6/1998 |
| WO | WO 98/31339 | 7/1998 |
| WO | 98/36733 | 8/1998 |
| WO | 98/52536 | 11/1998 |
| WO | 99/08649 | 2/1999 |
| WO | 99/20250 | 4/1999 |
| WO | 99/37282 | 7/1999 |
| WO | 99/53923 | 10/1999 |
| WO | 00/09082 | 2/2000 |
| WO | 00/15193 | 3/2000 |
| WO | 00/23051 | 4/2000 |
| WO | 00/33825 | 6/2000 |
| WO | 00/38731 | 7/2000 |
| WO | 00/61076 | 10/2000 |
| WO | 00/76461 | 12/2000 |
| WO | WO 00/72805 | 12/2000 |
| WO | 01/05366 | 1/2001 |
| WO | WO 01/01949 | 1/2001 |
| WO | 01/08681 | 2/2001 |
| WO | 01/10961 | 2/2001 |
| WO | 01/53198 | 7/2001 |
| WO | 01/54212 | 7/2001 |
| WO | 01/54679 | 8/2001 |
| WO | 01/62209 | 8/2001 |
| WO | 01/70242 | 9/2001 |
| WO | 01/82880 | 11/2001 |
| WO | 01/82890 | 11/2001 |
| WO | 01/85102 | 11/2001 |
| WO | 01/85128 | 11/2001 |
| WO | 01/95728 | 12/2001 |
| WO | 02/00820 | 1/2002 |
| WO | 02/15860 | 2/2002 |
| WO | 02/15873 | 2/2002 |
| WO | WO 02/24161 | 3/2002 |
| WO | 02/28435 | 4/2002 |
| WO | 02/41847 | 5/2002 |
| WO | 02/43490 | 6/2002 |
| WO | 02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | WO 03/005985 | 1/2003 |
| WO | 03/013984 | 2/2003 |
| WO | WO 03/015699 | 2/2003 |
| WO | 03/051294 | 6/2003 |
| WO | 03/053292 | 7/2003 |
| WO | 03/055445 | 7/2003 |
| WO | 03/055454 | 7/2003 |
| WO | 03/070301 | 8/2003 |
| WO | 03/071995 | 9/2003 |
| WO | 03/075851 | 9/2003 |
| WO | 03/092641 | 11/2003 |
| WO | 03/097002 | 11/2003 |
| WO | WO 03/094873 | 11/2003 |
| WO | 2004/017962 | 3/2004 |
| WO | 2004/037197 | 5/2004 |
| WO | 2004/037225 | 5/2004 |
| WO | 2004/003284 | 8/2004 |
| WO | 2004/064769 | 8/2004 |
| WO | 2004/064833 | 8/2004 |
| WO | 2004/071479 | 8/2004 |
| WO | 2004/078158 | 9/2004 |
| WO | 2004/078896 | 9/2004 |
| WO | 2004/093895 | 11/2004 |
| WO | 2004/112780 | 12/2004 |
| WO | 2005/011567 | 2/2005 |
| WO | 2005/018530 | 3/2005 |
| WO | 2005/032522 | 4/2005 |
| WO | 2005/044219 | 5/2005 |
| WO | 2005/063224 | 7/2005 |
| WO | 2005/065652 | 7/2005 |
| WO | 2005/076697 | 8/2005 |
| WO | 2005/097068 | 10/2005 |
| WO | 2005/102282 | 11/2005 |
| WO | 2005/102539 | 11/2005 |
| WO | 2005/117813 | 12/2005 |
| WO | 2006/003481 | 1/2006 |
| WO | 2006/010589 | 2/2006 |
| WO | 2006/011046 | 2/2006 |
| WO | 2006/020682 | 2/2006 |
| WO | 2006/028339 | 3/2006 |
| WO | 2006/031271 | 3/2006 |
| WO | 2006/045170 | 5/2006 |
| WO | 2006/079632 | 8/2006 |
| WO | 2006/081327 | 8/2006 |
| WO | 2006/091229 | 8/2006 |
| WO | 2006/100485 | 9/2006 |
| WO | 2006/120682 | 11/2006 |
| WO | 2006/121610 | 11/2006 |
| WO | 2006/122158 | 11/2006 |
| WO | 2006/129161 | 12/2006 |
| WO | 2006/131784 | 12/2006 |
| WO | 2007/007208 | 1/2007 |
| WO | WO 2007/010494 | 1/2007 |
| WO | 2007/012977 | 2/2007 |

(56) References Cited

FOREIGN PATENT DOCUMENTS

| | | |
|---|---|---|
| WO | 2007/023396 | 3/2007 |
| WO | 2007/031621 | 3/2007 |
| WO | 2007/039825 | 4/2007 |
| WO | 2007/050543 | 5/2007 |
| WO | 2007/054818 | 5/2007 |
| WO | 2007/072216 | 6/2007 |
| WO | WO 2007/082698 | 7/2007 |
| WO | 2007/085899 | 8/2007 |
| WO | 2007/085902 | 8/2007 |
| WO | 2007/099396 | 9/2007 |
| WO | 2007/111962 | 10/2007 |
| WO | 2008/008397 | 1/2008 |
| WO | 2008/010963 | 1/2008 |
| WO | 2008/038147 | 4/2008 |
| WO | 2008/041045 | 4/2008 |
| WO | 2008/075207 | 6/2008 |
| WO | 2008/087148 | 7/2008 |
| WO | 2008/110872 | 9/2008 |
| WO | WO 2008/104734 | 9/2008 |
| WO | 2008/152444 | 12/2008 |
| WO | 2009/007785 | 1/2009 |
| WO | 2009/069006 | 6/2009 |
| WO | 2009/072007 | 6/2009 |
| WO | 2009/087578 | 7/2009 |
| WO | 2009/090495 | 7/2009 |
| WO | 2009/090558 | 7/2009 |
| WO | 2009/098595 | 8/2009 |
| WO | WO 2011/006026 | 1/2011 |
| WO | WO 2011/026094 | 3/2011 |
| WO | 2011/039637 | 4/2011 |
| WO | 2011/039638 | 4/2011 |
| WO | WO 2011/106026 | 9/2011 |
| WO | WO 2011/138678 | 11/2011 |
| WO | WO 2013/136192 | 9/2013 |
| WO | WO 2014/134394 | 9/2014 |
| WO | WO 2014/134427 | 9/2014 |
| WO | WO 2014/151347 | 9/2014 |
| WO | WO 2014/201541 | 12/2014 |
| WO | WO 2015/009416 | 2/2015 |
| WO | WO 2015/075640 | 5/2015 |
| WO | WO 2015/114320 | 8/2015 |
| WO | WO 2015/153864 | 10/2015 |

OTHER PUBLICATIONS

"Minocycline" accessed on Ocotober 21, 2011 at en.wikipedia.org/wiki/Minocycline, 7 pages.

"Reaction Rate" Accessed at en.wikipedia.org/wiki/Reaction_rate on Dec. 18, 2011, 6 pages.

'Niram Chemicals' [online] Niram Chemicals, [retrieved on Jul. 17, 2012]. Retrieved from the Internet: <URL: http://www.indiamart.com/niramchemicals/chemicals.html>, 7 pages.

'Surfactant' [online]. Wikipedia, 2010, [retrieved on Oct. 24, 2010]. Retrieved from the Internet: <URL: http://en.wikipedia.org/wiki/Surfactant>, 7 pages.

Adachi, Shuji. "Storage and Oxidative Stability of O/W/ Nanoemulsions." Foods Food Ingredients. J. Jpn. vol. 209, No. 11. 2004. 1 page.

Alcohol SDA 40B.http://www.pharmco-prod.com/pages/MSDS/SDA.sub.--40B.sub.--200.pdf Accessed Dec. 9, 2008, 2 pages.

Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.

Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society*, Jul. 2006, Vienna, Austria, 2 pages.

Arct et al., "Common Cosmetic Hydrophilic Ingredients as Penetration Modifiers of Flavonoids", International Journal of Cosmetic Science, 24(6):357-366 (2002)—Abstract, 1 page.

Arisan, http://www.arisankimya.com/kozmetik.htm Accessed Dec. 10, 2008, 8 pages.

Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Barry and Badal, "Stability of minocycline, doxycycline, and tetracycline stored in agar plates and microdilution trays," *Current Microbiology*, 1978, 1:33-36.

Barry, B.W. et al, Comparative bio-availability and activity of proprietary topical corticosteroid preparations: vasoconstrictor assays on thirty-one ointments, British Journal of Dermatology, 93, 563-571, 1975.

Benet, et al., Application of NMR for the Determination of HLB Values of Nonionic Surfactants, Journal of the American Oil Chemists Society, vol. 49, 1972, 499-500.

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfactants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carbowax 1000MSDS; http://www.sciencelab.com/xMSDS-Polyethylene.sub.--glycol.sub.--1000-9926- 622. Accessed Dec. 13, 2008, 6 pages.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Cheshire, et al., Disorders of Sweating, www.medscape.com, Semin Neurol 23(4):399-406, 2003.

Chevrant-Breton, et al., "Etude du Traitement Capillaire <<Bioscalin>> dans les Alopecies Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

(56) References Cited

OTHER PUBLICATIONS

Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
Colloidal Silica. Retrieved online on Jun. 4, 2011. <URL:http://www.grace.com/engineeredmaterials/materialsciences/colloidalsilica/default.aspx>. Copyright 2011. 4 pages.
Croda 2. Croda Cetomacrogol 1000 Product Information Sheet. 2011 (no month given). 1 page.
Croda. Aracel 165 Product Summary. 2011 (no month given). 1 page.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Dawber, et al., "Hypertrichosis in Females Applying Minoxidil Topical Solution and in Normal Controls", JEADV, 17:271-275 (2003).
Denatonium Benzoate http://www.newdruginfo.com/pharmaceopeia/usp28/v28230/usp28nf23s0.sub.--m- 22790.htm Accessed Dec. 9, 2008, 2 pages.
Dentinger, et al., "Stability of Nifedipine in an Extemporaneously Compounded Oral Solution", American Journal of Health-System Pharmacy, 60(10):1019-1022 (2003)—Abstract, 1 page.
Disorder. (2007). In the American Heritage Dictionary of the English Language. Retrieved from http://www.credoreference.com/entry/hmdictenglang/disorder. 1 page.
Draelos, Z. D. "Antiperspirants and the Hyperhidrosis Patients." Dermatologic Therapy. 2001. vol. 14. pp. 220-224.
Edens, et al., "Storage Stability and Safey of Active Vitamin C in a New Dual-Chamber Dispenser", Journal of Applied Cosmetology, 17(4):136-143 (1999)—Abstract, 1 page.
Edirisinghe, et al., "Effect of fatty acids on endothelium-dependent relaxation in the rabbit aorta", Clin Sci (Load). Aug. 2006; 111(2): 145-51.
Edwards, "Imiquimod in Clinical Practice", J. Am Acad Dermatol., 43(1, Pt 2):512-517 (2000)—Abstract, 1 page.
Emulsifiers with HLB values. http://www.theherbarie.com/files/resources-center/formulating/Emulsifiers- .sub.--HLB.sub.--Values.pdf accessed Aug. 5, 2009 (3 pps).
Encyclopedia of Pharmaceutical Technology, Second Edition, vol. 3, Copyright 2002, 4 pages.
Esposito, E. et al. "Nanosystems for Skin Hydration: A Comparative Study." International Journal of Cosmetic Science. 29. 2007. pp. 39-47.
Ethanol, Accessed http://www.sigmaaldrich.com/catalog/ProductDetail.do?N4=E7023SIAL&N5=SEAR- CH.sub.--CONCAT.sub.--PNOBRAND.sub.--KEY&F=SPEC Dec. 9, 2008, 2 pages.
Ethylene Oxide Derivatives: An Essence of Every Industry. A definition of Emulsifier. http://www.emulsifiers.In/ethylene_oxide_derivatives2.htm. Accessed Jul. 12, 2011. 3 pages.
Farahmand, et al., "Formulation and Evaluation of a Vitamin C Multiple Emulsion", Pharmaceutical Development and Technology, 11(2):255-261 (2006)—Abstract, 1 page.
Final Office Action for U.S. Appl. No. 11/430,437, Tamarkin et al., Dec. 16, 2008, 24 pages.
Flick, Cosmetic and Toiletry Formulations, vol. 5, 2nd Edition, Copyright 1996, 63 pages. Relevant pp. 251-309.
Fontana, Anthony J., "Water Activity: Why it is Important for Food Safety," International Conference on Food Safety, Nov. 16-18, 1998, pp. 177-185.
Gallarate, et al., "On the Stability of Ascorbic Acid in Emulsified Systems for Topical and Cosmetic Use", International Journal of Pharmaceutics, 188:233-241 (1999).
Galligan, John et al., "Adhesive Polyurethane Liners for Anterior Restorations," J. Dent. Res., Jul.-Aug. 1968, pp. 629-632.

Gelbard et al. "Primary Pediatric Hyperhidrosis: A Review of Current Treatment Options." Pediatric Dermatology. 2008. 25 (6). pp. 591-598.
Gill, A.M, et al., "Adverse Drug Reactions in a Paediatric Intensive Care Unit," Acta Paediatr 84:438-441, 1995.
Gladkikh, "Ascorbic Acid and Methods of Increasing its Stability in Drugs", Translated from Khimiko-Farmatsevticheskii Zhurnal, 4(12):37-42 (1970)—1 page.
Glaser, et al., Hyperhidrosis: A Comprehensive and Practical Approach to Patient Management, Expert Rev. Dermatol. 1(6), 773-775 (2006).
Graves, S. et al. "Structure of Concentrated Nanoemulsions." The Journal of Chemical Physics.. 122 America Institute of Physics. Published Apr. 1, 2005. 6 pages.
Groveman, et al., "Lack of Efficacy of Polysorbate 60 in the Treatment of Male Pattern Baldness", Arch Intern Med, 145:1454-1458 (1985).
Gschnait, F., et al., "Topical Indomethacin Protects from UVB and UVA Irriadiation," Arch. Dermatol. Res. 276:131-132, 1984.
Hakan, et al., "The protective effect of fish oil enema in acetic acid and ethanol induced colitis," The Turkish Journal of Gasroenterology, 2000, vol. 11, No. 2, pp. 155-161.
Hall, Karla, "Diaper Area Hemangiomas: A Unique Set of Concerns," http://members.tripod.com/.about.Michelle.sub.--G/diaper.html, Dec. 1, 2008, 8 pages.
Hallstar. Retrieved online on Jun. 4, 2011. <URL:http://www.hallstar.com/pis.php?product=1H022>. 1 page.
Hargreaves, "Chemical Formulation, An Overview of Surfactant-Based Preparations Used in Everyday Life", *The Royal Society of Chemistry*, pp. 114-115 (2003).
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.
Harrison, et al., "Posttherapy Suppression of Genital Herpes Simplex Virus (HSV) Recurrences and Enhancement of Hsv-Specific T-Cell Memory by Imiquimod in Guinea Pigs", Antimicrobial Agents and Chemotherapy, 38(9):2059-2064 (1994).
Hashim, et al. "Tinea versicolor and visceral leishmaniasis," Int J Dermatol., Apr. 1994; 33(4), pp. 258-259 (abstract only).
Heart Failure, The Merck Manual, 2008 <<http://www.merck.com/mmhe/sec03/ch025/ch025a.html>> 12 pages.
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 Pages).
Hormones. Http://www.greenwillowtree.com/Page.bok?file=libido.html. Jan 2001.
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages
http://www.agworkshop.com/p3.asp, AG&Co. Essential oil workshop. 1 page. Accessed Jan. 31, 2010.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.
hydroxyethylcellulose. Http: //terpconnect.umd.edu/-choi/MSDS/Sigma-Aldrich/HYDROXYETHYL%20CELLULOSE, 5 pages, Jan. 14, 2004.
ICI Americas Inc. "The HLB System: A Time-Saving Guide to Emulsifier Selection." Mar. 1980. pp. 1-22.

(56) References Cited

OTHER PUBLICATIONS

Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
Izquierdo, P. et al. "Formation and Stability of Nano-Emulsions Prepared Using the Phase Inversion Temperature Method." University of Barcelona. Sep. 17, 2001. 1 page.
Jan. "Troubled Times: Detergent Foam." http://zetatalk.com/health/theall7c.htm. Accessed Feb. 9, 2012. 2 pages.
Joseph, "Understanding foams & foaming," University of Minnesota (1997), at http://www.aem.umn.edu/people/faculty/joseph/archive/docs/understandingfoams.pdf, pp. 1-8.
Kalkan, et al., The Measurement of Sweat Intensity Using a New Technique, Tr. J. of Medical Sciences 28, 515-517 (1998).
Kanamoto, et al., "Pharmacokinetics of two rectal dosage forms of ketoprofen in patients after anal surgery," J Pharmacobiodyn., Mar. 1988; 11(3):141-5.
Kang, et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," pp. 1-78, 2000.
Kathon.TM. CG (product information sheet by Rohm and Haas, Jun. 2006).
Kim, "Stability of Minoxidil in Aqueous Solution", Yakhak Hoechi, 30(5):228-231 (1986)—Abstract, 1 page.
Kinnunen, "Skin reactions to hexylene glycol," Contact Dermatitis Sep. 1989; 21(3): 154-8.
Kleber, M.D., H.D. et al., "Treatment of Patients with Substance Use Disorders, Second Edition," pp. 1-276, 2006.
Koerber, S., "Humectants and Water Activity," Water Activity News, 2000, ISSN No. 1083-3943.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetik Konzept. Kosmetische Praxis. 2006 (no month given). (5), 8-10. 3 pages.
Lebwohl et al. "Treatment of Psoriasis. Part 1. Topical Therapy and Phototherapy." *J. Am. Acad. Dermatol.* 45:487-498. Oct. 2001.
Lebwohl et al., "A randomized, double-blind, placebo-controlled study of clobestasol propionate 0.05% foam in the treatment of nonscalp psoriasis," *International Journal of Dermatology*, 2002, 41(5):269-274.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery in Water-Soluble Polymers," American Chemical Society, Chapter 23, 1991, pp. 350-366.
Li, et al., "Solubility Behavior of Imiquimod in Alkanoic Acids", Abstract 3029, Pharmaceutical Research, vol. 14, No. 11 Supplemental (November), p. S475 (1997), 2 pages.
Licking Vaginal Dryness without a Prescription. Accessed http://www.estronaut.com/a/vag.sub.--dryness.htm on Dec. 14, 2008, 3 pages.

Lippacher, A. et al. "Liquid and Semisolid SLN Dispersions for Topical Application" Rheological Characterization. European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale, The extra pharmacopoeia [28th] edition, Eds.: Reynolds, J.E.F. and Prasad, A.B., The Pharmaceutical Press, London, pp. 862-864, 1982.
Martindale. 33 ed. London, Bath Press, 2002. pp. 1073 and 1473.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merck index, 10th edition, Merck & Co., Inc.: Rahway, NJ, 1983, pp. 39 (entry 242 for allantoin).
Merck index, 14th edition, O'Neill, ed., 2006, entry for p-amino benzoic acid.
Merck index, 14th edition, O'Neill, ed., 2006, entry for zinc oxide.
Merck Index, An Encyclopedia of Chemicals, Drugs, and Biologicals. 13$^{th}$ Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.
Merriam-Webster Online Dictionaary, 2008, "Mousse," Merriam-Webster Online, Dec. 8, 2008 http://www.merriam-webster.com/dictionary/mousse, 2 pages.
Messenger, et al., "Minoxidil: Mechanisms of Action on Hair Growth", British Journal of Dermatology, 150:186-194 (2004).
Metronidazole. www.usp.org/pdf/EN/veterinary/metronidazole.pdf. accessed Sep. 10, 2009, 4 pages.
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985) —Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Neutrogena. Http://www.cosmetoscope.com/2010/04/neutrogeaclinic al-with-johnson-johnsons-cytomimic-techology/. Published Apr. 28, 2010. Accessed Sep. 11, 2010, 5 pages.
Nietz, "Molecular orientation at surfaces of solids," *J. Phys. Chem.*, 1928, 32(2): 255-269.
No Author Listed. "Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate. http://www.makingcosmetics.com/sunscreens/OM-Cinnamate-p102.html accessed Sep. 26, 2009, 1 page.
Padhi et al., "Phospho-olicines as positive-electrode materials for rechargeable lithium batteries," *J. Electrochemical Soc.*, 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkyl-benzoate.aspx. Printed Oct. 24, 2010. 1 page.

(56) References Cited

OTHER PUBLICATIONS

Pendergrass, "The shape and dimension of the human vagina as seen in three-dimensional vinyl polysiloxane casts," Gynecol Obstet. Invest. 1996:42(3):178-82.
Prescription Information for Aldara, Mar. 2007 (29 pages).
Prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural and synthetic triphylite," *J. of Power Sources*, 2001, 97-98:503-507.
Raymond, Iodine as an Aerial Disinfectant, Journal of Hygiene, vol. 44, No. 5 (May, 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Savin, et al., "Tinea versicolor treated with terbinafine 1% solution," Int J. Dermatol, Nov. 1999; 38(11), pp. 863-865.
Schmidt A., "Malassezia furfur: a fungus belonging to the physiological skin flora and its relevance in skin disorders," Curtis., Jan. 1997; 59(1), pp. 21-4 (abstract).
Schulze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only).
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, *Langmuir*, 2006, 22: 8337-8345.
Sigma Aldrich, "HLB-Numbers in Lithography Nanopatterning," http://www.sigmaaldrich.com/materials-science/micro-and-nanoelectronics/1- ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, http;//web.archive.org/web/20030810230608/http://www.skinbio.com/cpserum.-html, Dec. 1, 2008, 21 pages.

Skin Deep Cosmetics. PPG-40-PEG-60 Lanolin Oil http://www.cosmeticsdatabase.com/ingredient/722972/PPG-40-PEG-60__Lanolin__Oil/?ingred06=722972. 2010, 3 pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, 0. et al. "Nanoemulsions: A New Vehicle for Skincare Products." Advances in Colloid and Interface Science. 108-109.. 2004. pp. 145-149.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment ofdandruff/seborrhoeic dermatitis," Dermatolog Treat. Jun. 2002;13(2):51-60 (abstract only).
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle et al., Uptake of minoxidil from a new foam formulation devoid of propylene glycol to hamster ear hair follicles, *J. Invest. Dermatol.*, 2005, 124(4), A101.
Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.
Surfactant. Chemistry Glossary. Http://chemistry.about.com/od/chemistryglossary/g/surfactant.htm, 2012, 1 page.
Sweetman, Sean C. Martindale: The Complete Drug Reference. 33rd Edition. London. Pharmaceutical Press. Jun. 21, 2002. pp. 1073 and 1473. 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate-1. Accute toxicity of hydrocortisone 17-butyrate 21-propionate and its analogues in mice, rats and dogs (author's trans), J Toxicol Sci., Jul. 1981; 6 Suppl: 1-16 (Abstract only).
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, Feb. 4, 2009, 4 pages.
Tones-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.

(56) References Cited

OTHER PUBLICATIONS

Tzen, Jason T.C. et al. "Surface Structure and Properties of Plant Seed Oil Bodies." Department of Botany and Plant Sciences, University of California, Riverside, California 92521. Apr. 15, 1992. 9 pages.

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.

Veron, et al., "Stability of Minoxidil Topical Formulations", Ciencia Pharmaceutica, 2(6):411-414 (1992), Abstract, 1 page.

Wermuth, C.G. "Similarity in drugs: reflections on analogue design," Drug Discovery Today, vol. 11, Nos. 7/8, Apr. 2006, pp. 348-354.

Williams, "Scale up of an olive/water cream containing 40% diethylene glycol momoethyl ether", Dev. Ind. Pharm., 26(1):71-77 (2000).

Wormser et al., Protective effect of povidone-iodine ointment against skin lesions induced by sulphur and nitrogen mustards and by non-mustard vesicants, Arch. Toxicol., 1997, 71, 165-170.

Wormser, Early topical treatment with providone-iodine ointment reduces, and sometimes prevents, skin damage following heat stimulus, Letter to the Editor, Burns 24, pp. 383, 1998.

Yamada and Chung, "Crystal Chemistry of the Olivine-Type $Li(Mn_yFe_{1-y})PO_4$ and $(Mn_yFe_{1-y})PO_4$ as Possible 4 V Cathode Materials for Lithium Batteries," *J. Electrochemical Soc.*, 2001, 148(8): A960-967.

"Coal tars and coal-tar pitches," *Report on Carcinogens*, Twelfth Edition, 2011, 3 pages.

Adisen et al. "Topical tetracycline in the treatment of acne vulgaris," *J Drugs Dermatol.*, 2008, 7:953-5.

Baskaran et al., "Poloxamer-188 improves capillary blood flow and tissue viability in a cutaneous burn wound," *J. Surg. Res.*, 2001, 101(1):56-61.

Bell-Syer et al. "A systematic review of oral treatments for fungal infections of the skin of the feet," *J. Dermatolog. Treat.*, 2001, 12:69-74.

Boehm et al. 1994, "Synthesis of high specific activity [.sup.3 H]-9-cis-retinoic acid and its application for identifying retinoids with unusual binding properties," *J. Med. Chem.*, 37:408-414;.

Carapeti et al., "Topical diltiazem and bethanechol decrease anal sphincter pressure and heal anal fissures without side effects," *Dis Colon Rectum*, 2000, 43(10):1359-62.

Cook and Mortensen, "Nifedipine for treatment of anal fissures," *Dis Colon Rectum*, 2000, 43(3):430-1.

Dumortier et al., "A review of poloxamer 407 pharmaceutical and pharmacological characteristics," *Pharmaceutical Res.*, 2006, 23(12):2709-2728.

Ebadi et al., "Healing effect of topical nifedipine on skin wounds of diabetic rats," *DARU*, 2003, 11(1):19-22.

Effendy and Maibach. "Surfactants and Experimental Irritant Contact Dermatitis." *Contact Dermatol.*, 1995, 33:217-225.

Elias and Ghadially, "The aged epidermal permeability barrier," *Clinical Geriatric Medicine*, Feb. 2002, pp. 103-120.

Fantin et al., "Critical influence of resistance to streptogramin B-type antibiotics on activity of RP 59500 (Quinupristin-dalfopristin) in experimental endocarditis due to *Staphylococcus aureus*," Antimicrob Agents and Chemothery, 1999, 39:400-405.

Fluter et al., "Glycerol accelerates recovery of barrier function in vivo," *Acta Derm. Venereol*,. 1999, 79:418-21.

Garti et al. "Sucrose Esters microemulsions," *J. Molec. Liquids*, 1999, 80:253-296.

Hammer et al. "Anti-Microbial Activity of Essential Oils and other Plant extracts," *J. Applied Microbiology*, 1999, 86:985-990.

Hwang et al. "Isolation and identification of mosquito repellents in *Artemisia vulgaris*," *J. Chem. Ecol.*, 11: 1297-1306, 1985

Knight et al., "Topical diltiazem ointment in the treatment of chronic anal fissure," *Br. J. Surg.*, 2001, 88(4):553-6.

Kucharekova et al., "Effect of a lipid-rich emollient containing ceramide 3 in experimentally induced skin barrier dysfunction," *Contact Dermatitis*, Jun. 2002, pp. 331-338.

Leive et al, "Tetracyclines of various hydrophobicities as a probe for permeability of *Escherichia coli* outer membrane," *Antimicrobial Agents and Chemotherapy*, 1984, 25:539-544.

Luepke and Kemper, "The HET-CAM Test: An Alternative to the Draize Eye Test," *FD Chem. Toxic.*, 1986, 24:495-196.

Osborne and Henke, "Skin Penetration Enhancers Cited in the Technical Literature," *Pharm. Technology*, Nov. 1997, pp. 58-86.

Padi. "Minocycline prevents the development of neuropathic pain, but not acute pain: possible anti-inflammatory and antioxidant mechanisms," *Eur J. Pharmacol*, 2008, 601:79-87.

Palamaras and Kyriakis, "Calcium antagonists in dermatology: a review of the evidence and research-based studies," *Derm. Online Journal*, 2005, 11(2):8.

Passi et al., Lipophilic antioxidants in human sebum and aging, *Free Radical Research*, 2002, pp. 471-477.

Perrotti et al., "Topical Nifedipine With Lidocaine Ointment vs. Active Control for Treatment of Chronic Anal Fissure," *Dis Colon Rectum*, 2002, 45(11):1468-1475.

Repa et al. "All-trans-retinol is a ligand for the retinoic acid receptors," *Proc. Natl. Acad Sci, USA*, 90: 7293-7297, 1993.

Ruledge, "Some corrections to the record on insect repellents and attractants," *J. Am. Mosquito Control Assoc*, 1988, 4(4): 414-425.

Sakai et al., "Characterization of the physical properties of the stratum corneum by a new tactile sensor," *Skin Research and Technology*, Aug. 2000, pp. 128-134.

Schaefer, "Silicone Surfactants," *Tenside, Surfactants, Deterg.*, 1990, 27(3): 154-158.

Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.

Smith, "Hydroxy acids and skin again," *Soap Cosmetics Chemical Specialties*, 1993, pp. 54-59.

Solans et al. "Overview of basic aspects of microemulsions," Industrial Applications of Microemulsions, Solans et al Eds, New York, 1997, 66:1-17.

Squillante et al., "Codiffusion of propylene glycol and dimethyl isosorbide in hairless mouse skin," *European J. Pharm. Biopharm.*, 1998, 46(3):265-71.

Todd et al. "Volatile Silicone Fluids for Cosmetics," *91 Cosmetics and Toiletries*, 1976, 27-32.

Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.

USP23/NF 18 the United States Pharmacopeia: The National Formulary, US Pharmacopoeia, 1995, p. 10-14.

Van Slyke, "On the measurement of buffer values and on the relationship of buffer value to the dissociation constant of the buffer and the concentration and reaction of the buffer solution," *J. Biol. Chem.*, 1922, 52:525-570.

Van Cutsem et al., "The antiinflammatory efects of ketoconazole," *J. AM. ACAD. Dermatol.*, 1991, 25(2 pt 1):257-261.

Wang and Chen, "Preparation and surface active properties of biodegradable dextrin derivative surfactants," *Colloids and Surfaces A: Physicochemical and Engineering Aspects*, 2006, 281(1-3): 190-193.

Weindl et al., "Hyaluronic acid in the biological, pharmaceutical and clinical treatment and prevention of skin diseases: molecular aspects," *Skin Pharmacology and Physiology*, 2004, 17: 207-213.

Xynos et al., "Effect of nifedipine on rectoanal motility," *Dis Colon Rectum*, 1996, 39(2):212-216.

Yamada et al., "Candesartan, an angiotensin II receptor antagonist, suppresses pancreatic inflammation and fibrosis in rats," *J. Pharmacol. Exp. Ther.*, 2003, 307(1)17-23.

Paragraph E.3.1 of regulation (EC) No. 2003 (See Directive 67/548/ EEC OJ 196, 16.8, 1967, p. 1.

Tzen et al., Lipids, proteins and structure of seed oil bodies from diverse species; *Plant Physiol.*, 1993, 101:267-276.

(56) References Cited

OTHER PUBLICATIONS

Brown et al. " Structural dependence of flavonoid interactions with Cu2+ inos: implications for their antioxidant properties," *Biochem. J.*, 1998, 330:1173-1178.
Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.
"Mineral oil USP," Chemical Abstracts Service Registry No. 8012-95-1, 2011, 7 pages.
"Tea tree oil," Chemical Abstract No. 68647-73-4, 2012, 2 pages.
Lin et al., "Ferulic acid stabilizes a solution of vitamins c and e and doubles its photoprotection of skin," *J Invest Dermatol*, 2005, 125:826-32.
International Preliminary Report on Patentability from PCT/IB2008/003908 dated, Jun. 2, 2010, 8 pages; International Search Report dated, Sep. 25, 2009, 3 pages.
Al-Mughrabi et al., "Effectiveness of Essential Oils and Their Combinations with Aluminum Starch Octenylsuccinate on Potato Storage Pathogens," TEOP, 2013, 16(1):23-31.
Beauty Banter, "Interesting list of comedogenic ingredients!!!!!!!!!!!!" QVC blog, Interesting list of comedogenic ingredients, 2014, 1-14.
Chemical Characteristics, The Olive Oil Source, ©1998-2015, retrieved on Jun. 12, 2015, http://www.oliveoilsource.com/page/chemical-characteristics, 10 pages.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
CODEX Standard for Olive Oils and Olive Pomace Oils CODEX STAN 33/1981, Adopted in 1981, recently amended 2013, 8 pages.
Communication of a Notice of Opposition in European Application No. 03772600.7, dated Jan. 13, 2015, 36 pages.
Cremophor A Grades, BASF The Chemical Company, Jan. 2008, 6 pages.
Devos and Miller, "Antisense Oligonucleotides: Treating neurodegeneration at the Level of RNA," Neurotherapeutics, 2013, 10:486-497.
Ellis et al., "The Treatment of Psoriasis with Liquor Carbonis Detergens," J. Invest Dermatology, 1948, 10:455-459.
GELS, UNC, The Pharmaceutics and Compounding Laboratory, retrieved on Aug. 25, 2014, http://pharmlabs.unc.edu/labs/gels/agents/htm, 4 pages.
Griffin, "Calculation of HLB Values of Non-Ionic Surfactants," Journal of the Society of Cosmetic Chemists, May 14, 1954, 249-256.
Haw, "The HLB System: A Time Saving Guide to Surfactant Selection," Presentation to the Midwest Chapter of the Society of Cosmetic Chemists, Mar. 9, 2004, 39 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Le Vine et al., "Components of the Goeckerman Regimen," Journal of Investigative Dermatology, 1979, 73:170-173.
Luviquat Polymer Grades, BASF The Chemical Company, May 2012, 32 pages.
Mailer, "Chemistry and quality of olive oil," NSW Dept. of Primary Industries, Aug. 2006, Primefact 227, 1-4.
Material Safety Data Sheet, Luvitol Eho, Caelo, Nov. 28, 2013, 4 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Oh et al., "Antimicrobial activity of ethanol, glycerol monolaurate or lactic acid against Listeria moncylogenes,"Int. J. Food Microbiology, 1993, 20:239-246.
Omega-9 Fatty Acids (Oleic Acid), Orthomolecular.org, Dec. 2004, retrieved on Aug. 15, 2014, http://orthomolecular.org/nutrients/omega9.html. 1 page.
Polystyrene, Wikipedia the free encyclopedia, retrieved Apr. 21, 2014, http://web.archive.org/web/20060312210423/http://en.wikipedia.org/wiki/Polystyrene, 4 pages.
Permethrin (Insecticide), Wildpro, retrieved on Jun. 4, 2015, http://wildpro.twycrosszoo.org/S/00Chem/ChComplex/perm.htm, 5 pages.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Rohstoffinformationen, Hoffmann Mineral, 2008, 8 pages (with English translation).
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
United States Standards for Grades of Olive Oil and Olive-Pomace Oil, United States Dept. of Agriculture, Oct. 25, 2010, 21 pages.
Vera et al., "Scattering optics of Foam," Applied Optics, Aug. 20, 2001, 40(24):4210-4214.
WebMD, "Psoriasis Health Center," 2014, retrieved Apr. 13, 2015, http://www.webmd.com/skin-problems-and-treatments/psoriasis/psoriasis-symptoms, 3 pages.
WebMD, "Understanding Rosacea—the Basics," 2014, retrieved Apr. 13, 2015, http://www.webmd.com/skin-problems-and-treatments/understanding -rosacea-basics, 5 pages.
Williams et al., "Acne vulgaris," Lancet, 2012, 379:361-372.
Ziolkowsky, "Moderne Aerosolschaume in der Kosmetik (Modern Aerosol Foams in Chemical and Marketing Aspects),", Seifen-Ole-Fette-Wachse, Aug. 1986, 112(13): 427-429 (with English translation).
"Alcohol," Wikipedia, the free encyclopedia, retrieved on May 17, 2014, http://en.wikipedia.org/wiki/Alcohol, 17 pages.
"Arquad HTL8-MS,"*AkzoNobel Functional Applications*, retrieved on Mar. 18, 2013, Retrieved from the Internet: <URL: http://sc.akzonobel.com/en/fa/Pages/product-detail.aspx?prodID=8764>, 1 page.
"Can tuberous sclerosis be prevented?," *Sharecare*, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
"Crohn's Disease," *Merck Manual Home Edition*, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
"Dacarbazine," *Chemical Book*, 2010, retrieved on Oct. 18, 2013, <URL: http://www.chemicalbook.com/ChemicalProductProperty_EN_CB7710656.htm>, 2 pages.
"Drug Index (Professional)—Dacarbazine," *BC Cancer Agency*, Jun. 2004, retrieved on Oct. 18, 2013, <URL:http://www.bccancer.bc.ca/HPI/DrugDatabase/DrugIndexPro/Dacarbazine.htm>, 6 pages.
"Fully refined paraffin waxes (FRP Wax)," *Industrial Raw Materials LLC*, Feb. 21, 2008, retrieved on Aug. 22, 2013, <http://irmwax.com/Wax/Paraffin/fully_refined.asp> 1 page.
"Gas Gangrene," Merck Manual Home Edition, 2008, retrieved on Jan. 16, 2013, <http://www.merckmanuals.com/home/infections/bacterial_infections/gas_gangrene.html?qt=gasgangrene&alt=sh>1 page.
"Human Immunodeficiency Virus Infection," Merck Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh>, 11 pages.
"Minocycline (DB01017)," *Drug Bank*, Feb 8, 2013, retrieved on Aug. 15, 2013, <http://www.drugbank.ca/drugs/DB01017>, 10 pages.
"New Nanomaterials to deliver anticancer drugs to cells developed," *Science Daily*, Jun. 2007, retrieved on Oct. 14, 2013, <URL: http://www.sciencedaily.com/releases/2007/06/070607112931.htm>, 3 pages.
"Product Data Sheet for Meclocycline," *bioaustralis fine chemicals*, Jun. 28, 2013, 1 page.

(56) References Cited

OTHER PUBLICATIONS

"Shear," Vocabulary.com, retrieved on Aug. 23, 2013, <URL: https://www.vocabulary.com/dictionary/shear>, 3 pages.
"Sheer," Vocabulary.com, retrieved on Aug. 23, 2013, <URL: https://www.vocabulary.com/dictionary/sheer>, 3 pages.
"View of NCT01171326 on Dec. 7, 2010," ClinicalTrials.gov archive, Dec. 7, 2010, retrieved on Sep. 9, 2013, <http://clinicaltrials.gov/archive/NCT01171326/2010_12_07>, 4 pages.
"View of NCT01362010 on Jun. 9, 2011," ClinicalTrials.gov archive, Jun. 9, 2011, retrieved on Sep. 9, 2013, <http://clinicaltrials.gov/archive/NCT01362010/2011_06_09>, 3 pages.
"What is TSC?," *Tuberous Sclerosis Alliance*, Jan. 1, 2005, retrieved on Feb. 6, 2014, <URL: http://www.tsalliance.org.pages.aspx?content=2>, 3 pages.
Abrams et al., "Ciclopirox gel treatment of scalp seborrheic dermatitis," *Hydroxy-Piridones as Antifungal Agents with Special Emphasis on Onychomycosis*, 1999, Chapter 8, 45-50.
Blaney and Cook, "Topical use of tetracycline in the treatment of acne," *Arch Dermatol*, Jul. 1976, 112:971-973.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Cole and Gazewood, "Diagnosis and Treatment of Impetigo," *Am Fam Physician*, Mar. 15, 2007, 75(6):859-864.
Cunha, "Minocycline versus Doxycycline in the treatment of Lyme Neuroborreliosis," *Clin. Infect. Diseases*, 2000, 30: 237-238
Durian et al., "Scaling behavior in shaving cream," *The American Physical Society*, Dec. 1991, 44(12):R7902-7905.
Google Search Strategy for Minocycline Solubility, retrieved on Aug. 15, 2013, <http://www.googl.com/search?rls=com.microsoft%3Aen-us%3AIE-SearchBox&q-melocycline+solubility>, 1 page.
Harry, "Skin Penetration," The British Journal of Dermatology and Syphilis, 1941, 53:65-82.
Lee et al., "Historical review of melanoma treatment and outcomes," Clinics in Dermatology, 2013, 31: 141-147.
Livingstone and Hubel, "Segregation of form, color, movement, and depth: Anatomy, physiology, and perception," Science, May 1988, 240:740-749.
*Molins PLC v. Textron Inc.*, 48 F.3d 1172, 33 USPQ2d 1823 (Fed. Cir. 1995), 19 pages.
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neves et al., "Rheological Properties of Vaginal Hydrophilic Polymer Gels," *Current Drug Delivery*, 2009, 6:83-92.
Oranje et al., "Topical retapamulin ointment, 1%, versus sodium fusidate ointment, 2%, for impetigo: a randomized, observer-blinded, noninferiority study," *Dermatology*, 2007, 215(4):331-340.
Prud'Homme et al., *Foams: theory, measurements and applications*, Marcel Dekker, Inc., 1996, 327-328.
Purdy et al., "Transfusion-transmitted malaria: unpreventable by current donor exclusion guidelines?" *Transfusion*, Mar. 2004, 44:464.
*Reregistration Eligibility Decision for Pyrethrins*, EPA, Jun. 7, 2006, 108 pages.
Schmolka, "A review of block polymer surfactants," *Journal of the American Oil Chemists Society*, Mar. 1977, 54: 110-116.
Schott, "Rheology," *Remington's Pharmaceutical Sciences*, 17th Edition, 1985, 330-345.
Sciarra, "Aerosol Technology," *Kirk-Othmer Encyclopedia of Chemical Technology*, Jul. 2012, 20 pages.
Scully et al., "Cancers of the oral mucosa treatment and management," *Medscape Drugs, Diseases and Procedures*, Apr. 20, 2012, retrieved on Oct. 12, 2013, <http://emedicine.medscape.com/article/1075729-treatment>, 10 pages.
Sehgal, "Ciclopirox: a new topical pyrodonium antimycotic agent: A double-blind study in superficial dermatomycoses," *British Journal of Dermatology*, 1976, 95:83-88.

SOFTEMUL-165: Product Data Sheet, Mohini Organics PVT LTD, retrieved Apr. 10, 2014, http://www.mohiniorganics.com/Softemul165.html#, 1 page.
*Sun Pharmaceutical Industried Ltd.* v. *Eli Lilly and Co.*, 611 F.3d 1381, 95 USPQ2d 1797 (Fed. Cir. 2010),7 pages.
Tavss et al., "Anionic detergent-induced skin irritation and anionic detergent-induced pH rise of bovine serum albumin," *J. Soc. Cosmet. Chem.*, Jul./Aug. 1988, 39:267-272.
Tirmula et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Allantoin, Römpp Online, retrieved on Sep. 23, 2015, https://roempp.thieme.de/roempp4.0/do/data/Rd-O 1-01552, 5 pages.
Coconut Oil, Wikipedia, the free encyclopedia, retrieved on Jul. 3, 2015, https://en.wikipedia.org/wiki/Coconut_oil, 8 pages.
Communication of a Notice of Opposition in European Application No. 03772600.7, dated Sep. 23, 2015, 42 pages.
Communication of a Notice of Opposition in European Application No. 03772600.7, dated Sep. 24, 2015, 30 pages.
Diethyltoluamid, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Healy, "Gelled Emollient Systems for Controlled Fragrance Release and Enhanced Product Performance," Cosmetics and toiletries, 2002, 117(2): 47-54.
LEUNAPON-F, LEUNA-Tenside, Screenshot, retrieved on Sep. 18, 2015, http://www.leuna-tenside.de/2006_7_14_3143/2006_8_7 5750/2006_8_7 24l/cas-68439-49-6, 1 page.
Mead, "Electrostatic Mechanisms Underlie Neomycin Block of the Cardiac Ryanodine Receptor Channel (RyR2)," Biophysical Journal, 2004, (87): 3814-3825.
Rowe et al., "Glyceryl Monooleate," Handbook of Pharmaceutical Excipients, 2011, pp. 1-5, retrieved on Dec. 19, 2011, http://www.medicinescomplete.com/mc/excipients/current/1001938996.htm?q=glyceryl%20monooleate&t=search&ss=text&p=1# hit.
Rowe et al., "Octyldodecanol," Handbook of Pharmaceutical Excipients, 2011, pp. 1-4, retrieved on Dec. 19, 2011, URL:http://www.medicinescomplete.com/mc/excipients/current/1001942450.htm?q=octyldodecanol&t=search&ss=text&p=1# hit.
Rowe et al., "Sucrose Palmitate," Handbook of Pharmaceutical Excipients, 2011, pp. 1-5, retrieved on Dec. 19, 2011, URL:http://www.medicinescomplete.com/mc/excipients/current/EXP-TD-c46-mn0001.htm?q=sucrose%20stearate&t=search&ss=text&p=1# hit.
Rowe et al., "Sucrose Stearate," Handbook of Pharmaceutical Excipients, 2011, pp. 1-4, retrieved on Dec. 19, 2011, URL:http://www.medicinescomplete.com/mc/excipients/current/EXP-TD-cll-mnOOO1-mnOOO1.htm?q=sucrose%20stearate&t=search&ss=text&p=3# hit.
RSES (Oil in Refrigerator Systems, Service Application Manual, 2009).
Security Datasheet, Luvitol EHO, Cetearyloctanoat, Nov. 27, 2013, 10 pages.
Sigma-Aldrich. http://www.sigmaaldrich.com/catalog/product/sial/p1754?lang=en® ion=. Published: Mar. 5, 2014.
Triethanolamine, haute.de, retrieved on Sep. 14, 2015, http://www.haut.de/service/inci/anzeige&id=16384&query=Triethanolamine &funktio . . . , 3 pages.
Wenninger et al., "International Cosmetic Ingredient Dictionary and Handbook," The Cosmetic, Toiletry, and Fragrance Association, Washington, DC., 1997, vol. 1, 4 pages.
Williams et al., "Urea analogues in propylene glycol as penetration enhancers in human skin," International Journal of Pharmaceutics, 1989, 36, 43-50.
Wu et al., "Interaction of Fatty Acid Monolayers with Cobalt Nanoparticles," NANO Letters, 2004, 4(2): 383-386.
Everything but the Olive, (the Olive Oil Source 1998-2016). http://www.oliveoilsource.com/pageAchemical-characteristics).

(56) References Cited

OTHER PUBLICATIONS

Kaur et al., "Formulation Development of Self Nanoemulsifying Drug Delivery System (SNEDDS) of Celecoxib for Improvement of Oral Bioavailability," Pharmacophore, 2013, 4(4):120-133.
Lamisil, Lamisil.http://www.fda.gov/downloads/Drugs/DrugSafety/PostmarketDrugSafetyInformationforPatientsandProviders/ucm052213.pdf, Published: Apr. 2001.
Sanders et al., "Stabilization of Aerosol Emulsions and Foams," J. Soc. Cosmet. Chem., 1970, 21:377-391.
Suppositories?, CareCure, http://sci.rutgers.edu/forum/showthread.php?4176-Suppositories. Published: Apr. 16, 2002.
Valenta, "Effects of Penetration Enhancers on the In-vitro Percutaneous Absorption of Progesterone," J. Phann Pharrnacol., 1997, 49: 955-959.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Albrecht et al., "Topical minocycline foam for moderate to severe acne vulgaris: Phase 2 randomized double-blind, vehicle-controlled study results," J. Am. Acad. Dermatol., 2016, 74(6):1251-1252.
Chapter 1 Meaning of HLB Advantages and Limitations 1980; 4 pages.
Material Safety Data Sheet, Squalane, TCI America, 5 pages, https://www.spectrumchemical.com/MSDS/TC1-H0096.pdf. Published: Oct. 6, 2014.
Sorbitan Esters, [online] retrieved on Jul. 1, 2016 from: http://www.drugfuture.com/chemdata/sorbitan-esters.html 2 pages.
Sreenivasan et al., "Studies on Castor Oil. I. Fatty Acid Composition of Castor Oil," Journal of the American Oil Chemists Society. 1956, 33:61-66.

\* cited by examiner 1  2  3

FOAM CONTAINING BENZOYL PEROXIDE

CROSS REFERENCE TO RELATED APPLICATIONS

This application claims priority under 35 U.S.C. 371 to PCT/IB08/03908, filed on Dec. 1, 2008, which claims priority under 35 U.S.C. §119(e) to U.S. Provisional Application No. 61/004,838, filed on Nov. 30, 2007, each of which is incorporated by reference herein in its entirety.

FIELD

The present invention relates to foamable compositions for treating inter alia acne comprising benzoyl peroxide; to a therapeutic kit comprising such compositions; and to a method of treating acne using such compositions.

BACKGROUND

Acne Vulgaris is an inflammatory disease of the skin, caused by changes in the pilosebaceous units (skin structures consisting of a hair follicle and its associated sebaceous gland). Acne develops as a result of blockages in follicles. Hyperkeratinization and formation of a plug of keratin and sebum (a microcomedo) is the earliest change. Enlargement of sebaceous glands and an increase in sebum production occur with increased androgen (DHEA-S) production at adrenarche. The microcomedo may enlarge to form an open comedo (blackhead) or closed comedo (whitehead). In these conditions the naturally occurring largely commensual bacteria *Propionibacterium acnes* can cause inflammation, leading to inflammatory lesions (papules, infected pustules, or nodules) in the dermis around the microcomedo or comedo, which results in redness and may result in scarring or hyperpigmentation. See, e.g., Webster GF (2002), "Acne vulgaris," *BMJ* 325 (7362): 475-9, PMID 12202330.

Benzoyl peroxide ("BPO") has been widely used for the treatment of acne. Gel or cream containing benzoyl peroxide is usually rubbed into the pores over the affected region. In addition to its therapeutic effect as a keratolytic (a chemical that dissolves the keratin plugging the pores), benzoyl peroxide also prevents new lesions by killing *P. acnes*. Benzoyl peroxide has the advantage of being a strong oxidizer and thus does not appear to generate bacterial resistance. However, the disadvantage associated with the use of benzoyl peroxide is that it routinely causes dryness, local irritation and redness.

Additionally, compositions containing benzoyl peroxide for topical treatment of acne are available primarily in cream, lotion gel and ointment forms. Rubbing creams or ointments into the skin is inherently inefficient and difficult to achieve a constant and balanced application over large area of skin. Lotions on the other hand are not ideal as they can run and drip and may not be homogenous. Therefore, while semi-solid compositions, such as creams, gels and ointments are commonly used by consumers, new forms are desirable in order to achieve better control of the application, while maintaining or bestowing the skin beneficial properties of such products. Hence, the development of new compositions, having breakable foam consistency when released from a container and liquid properties when applied onto the skin is advantageous. Further, the development of new foamable compositions that can reduce or diminish the dryness and irritation associated with the use of benzoyl peroxide is especially desirable. Benzoyl peroxide is a sensitive active agent which reacts readily and degrades for example in oil. As a powerful oxidant, it can cause the breakdown of other active agents such as certain antibiotics if present in the same formulation and is itself sensitive to formulation conditions which have different values. Hence, there is a need to provide foamable compositions in which benzoyl peroxide is stable in the presence of other excipients.

Whilst it may be predictable to add a moisturizing agent to a BPO formulation to counter the drying effect of BPO this per se is not sufficient to prevent dryness. Identifying formulations in which BPO remains stable and homogenous that are able to improve skin moisture rapidly and effectively on application to the skin is a challenge.

Foams and, in particular, foam emulsions are complex dispersion systems which do not form under all circumstances. Slight shifts in foam emulsion composition, such as by the addition of active ingredients, may destabilize the foam. Foams are very complex and sensitive systems and are not formed at will. Mere addition of basic ingredients like oil, water, surfactant and propellant is far from sufficient to produce foams of quality that are homogenous, stable, breakable upon mechanical force and can be used to provide a shelf stable pharmaceutical or cosmetic composition. Small deviations may lead to foam collapse. Much consideration needs to be given to facilitate the introduction of an active agent, such as examining compatibility and non reactivity with the various excipients and container and determining shelf life chemical stability.

Neubourg (US 2006/0099151), for example, notes that the stability of foam is strongly dependent on the specific composition of the foam forming components, so that even small deviations in the composition may lead to a collapse of the foam. Gordon et al. (U.S. Pat. No. 3,456,052). also teaches that one cannot generate a good quality foam by simply adding a propellant to a mixture of components:

SUMMARY

In one aspect, a foamable composition for treating acne is provided, comprising (a) a prefoam emulsion composition comprising: i. benzoyl peroxide; ii. one or more surface-active agents; iii. about 0.001% to about 1% by weight of the total composition of at least one polymeric additive; and iv. water; (b) up to about 2% by weight of the total composition of a buffer system, wherein the buffer system is selected to provide a viscosity of the prefoam composition of less than about 8000 centipoises (cps) at room temperature; and (c) a liquefied or compressed gas propellant at a concentration of about 3% to about 25% by weight of the total composition, wherein the viscosity of the foamable composition is less than about 8000 centipoises (cps) at room temperature. In one embodiment, the foam produced from the foamable composition has an average bubble size of less than about 150 microns.

In one embodiment, the prefoam emulsion composition further comprises a pH adjusting component selected from the group consisting of, a base or a buffer system, said pH adjusting component selected to be able to gel the polymeric additive. In another embodiment, the pH of the prefoam emulsion composition is between about 4.0 and about 6.0. In another embodiment, the buffer system is at a pH less than the pH of the prefoam emulsion before addition of the buffer and is selected to provide a liquid prefoam emulsion. In another embodiment, the buffer system comprises citric acid and sodium citrate or lactic acid and ammonium lactate.

In one embodiment, the composition further comprises about 5% to about 15% a moisturizing complex comprising glycerine and a salt of 2-pyrrolidone-5-carboxylic acid (PCA). In another embodiment, the composition further comprises about 5% to about 30% of a moisturizing complex comprising an oil and at least one of glycerine and a salt of 2-pyrrolidone-5-carboxylic acid (PCA), wherein the oil comprises mineral oil and a silicone oil. In another embodiment, the moisturizing complex has at least three of the following characteristics: (a) improves the chemical stability of BPO in the composition; (b) improves the homogeneity of BPO in the composition; (c) improves the quality of the foam produced from the foamable propellant composition; (d) improves the hydration of skin after 7 hours by at least about 20%.

In one embodiment, the composition further comprises about 1% glycerol stearate and one of about 1% stearol alcohol or about 1% cetostearyl alcohol.

In one embodiment, the polymeric additive comprises an amphiphilic polymer. In another embodiment, the amphiphilic polymeric additive comprises a carbomer. In another embodiment, the polymeric additive further comprises a polymeric agent selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose, Sodium CMC, carboxymethylhydroxyethylcellulose, xanthan gum, guar gum, carrageenin gum, locust bean gum and tragacanth gum and mixtures of two or more thereof.

In one embodiment, the concentration range of benzoyl peroxide is selected from the group of (i) between about 0.005% and about 0.5%; (ii) between about 0.5% and about 2%; (iii) between about 2% and about 5%; (iv) between about 5% and about 10%; and (v) between about 10% and about 15%.

In one embodiment, the concentration of the one or more surface-active agents is between about 0.1% and about 5%. In another embodiment, the surface-active agent is selected from the group consisting of Steareth-21, Steareth-2, steareth 20, Polysorbate 80, Polysorbate 60, Polysorbate 20, ceteth 20, PEG 40-stearate, PEG 100-stearate, PEG-30 dipolyhydroxystearate, sorbitan stearate (span 60), sorbitan palmitate (span 40), sorbitan laurate (span 20), sorbitan monooleate (span 80), glycerol monostearate, glyceryl stearate, laureth 4, ceteareth 20, macrogol cetostearyl ether, ceteth 2 (Lipocol C-2), sucrose distearate (Sisterna SP30), polyoxyethylene (100) stearate, and mixtures thereof.

In one embodiment, the composition comprises about 1% to about 15% by weight of an oil. In another embodiment, the composition comprises about 1% to about 15% by weight of an oil, wherein the oil is selected from the group consisting of mineral oil, silicone oil, jojoba oil, MCT oil and mixtures of two or more thereof.

In one embodiment, the composition comprises about 0.1% to about 5% by weight of a therapeutically active foam adjuvant selected from the group consisting of fatty alcohols having 15 or more carbons in their carbon chain; fatty acids having 16 or more carbons in their carbon chain; fatty alcohols derived from beeswax and including a mixture of alcohols, a majority of which has at least 20 carbon atoms in their carbon chain; fatty alcohols having at least one double bond; fatty acids having at least one double bond; branched fatty alcohols; branched fatty acids; fatty acids substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid and mixtures thereof. In another embodiment, the composition comprises at least one additional therapeutic agent, which is an antibiotic agent, selected from the group consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroides, sulfonamides, tetracycline, lincomycin class, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof, and naturally occurring antibiotic compounds. In one embodiment, the antibiotic is clindamycin.

In another aspect, a foamable composition for treating acne is provided, comprising: (a) a prefoam emulsion composition comprising: i. benzoyl peroxide; ii. one or more surface-active agents; iii. about 0.001% to about 1% by weight of the total composition of at least one polymeric additive; iv. about 5% to about 15% by weight of the total composition of a moisturizing complex; and v. water; (b) up to about 2% by weight of the total composition of a buffer system, wherein the buffer system is selected to provide a prefoam composition that is fluid at room temperature; and (c) a liquefied or compressed gas propellant at a concentration of about 3% to about 25% by weight of the total composition, wherein the foamable propellant composition is fluid at room temperature. In one embodiment, the foam produced from the foamable propellant composition has an average bubble size of less than about 150 microns.

In one embodiment, the prefoam emulsion composition further comprises a pH adjusting component selected from the group consisting of a base or a buffer system, said pH adjusting component selected to be able to gel the polymeric additive. In one embodiment, the pH of the prefoam emulsion composition is between about 4.0 and about 6.0. In another embodiment, the buffer system is at a pH less than the pH of the prefoam emulsion before addition of the buffer and is selected to provide a liquid prefoam emulsion.

In another aspect, a method of treating acne is provided, the method comprising administering topically to a subject having acne a foamable composition provided herein.

In another aspect, a foamable composition is provided, comprising: (a) a prefoam composition comprising: i. a suspended solid active agent; ii. one or more surface-active agents; iii. about 0.001% to about 1% by weight of the total composition of at least one polymeric additive; iv. up to about 2% by weight of the total composition of a buffer system; and v. water, wherein the viscosity of the prefoam composition is less than about 8000 centipoises (cps) at room temperature; and (b) a liquefied or compressed gas propellant at a concentration of about 3% to about 25% by weight of the total composition, wherein the viscosity of the foamable composition is less than about 8000 centipoises (cps) at room temperature.

In another aspect, a foamable composition is provided, comprising: (a) a prefoam composition comprising: i. a suspended solid active agent; ii. one or more surface-active agents; iii. about 0.001% to about 1% by weight of the total composition of at least one polymeric additive; iv. about 5% to about 15% by weight of the total composition of a moisturizing complex; and v. water; (b) up to about 2% by weight of the total composition of a buffer system, wherein the buffer system is selected to provide a prefoam composition that is fluid at room temperature; and (c) a liquefied or compressed gas propellant at a concentration of about 3% to about 25% by weight of the total composition, wherein the foamable propellant composition is fluid at room temperature.

In one embodiment, the foam produced from the foamable propellant composition has an average bubble size of less than about 150 microns.

In one embodiment, the suspended solid agent has an average particle size of less than about 35 microns.

In one embodiment, the buffer system comprises citric acid and sodium citrate or lactic acid and ammonium lactate.

In one embodiment, the composition further comprises about 5% to about 15% a moisturizing complex comprising glycerine and a salt of 2-pyrrolidone-5-carboxylic acid (PCA). In another embodiment, the composition further comprises about 5% to about 30% of a moisturizing complex comprising an oil and at least one of glycerine and a salt of 2-pyrrolidone-5-carboxylic acid (PCA), wherein the oil comprises mineral oil and a silicone oil.

In one embodiment, the composition further comprises at least one organic carrier selected from the group consisting of a hydrophobic organic carrier, an organic polar solvent, an emollient and mixtures thereof, at a concentration of about 2% to about 50% by weight. In another embodiment, the at least one organic carrier is present in an amount selected from the group consisting of (i) about 2% to about 5%; (ii) about 5% to about 10%; (iii) about 10% to about 20%; and (iv) about 20% to about 50% by weight.

In one embodiment, the composition further comprises a penetration enhancer. In another embodiment, the penetration enhancer is selected from the group consisting of propylene glycol, butylene glycols, hexylene glycol, glycerol, pentaerythritol, sorbitol, mannitol, oligosaccharides, dimethyl isosorbide, monooleate of ethoxylated glycerides having about 8 to 10 ethylene oxide units, polyethylene glycol 200-600, transcutol, glycofurol and cyclodextrins.

In one embodiment, the composition further comprises at least one additional therapeutic agent selected from the group consisting of an a steroidal anti-inflammatory agent, an immunosuppressive agent, an immunomodulator, an immunoregulating agent, a hormonal agent, an androgen, an estrogen, a prostaglandin, an antiandrogen agent, a testosterone inhibitor, a dihydrotestosterone inhibitor, an antifungal agent, an antiviral agent, an antiparasitic agent, a retinoid, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, a keratolytic agent, urea, a urea derivative, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, an organo-metallic compound, and organo-boron compound, an organo-berrilium compound, talc, carbon, an anti wrinkle agent, a skin whitening agent, a skin protective agent, a masking agent, an anti-wart agent, a refatting agent, a lubricating agent and mixtures thereof. In another embodiment, the additional therapeutic agent is sensitive to oxidation and wherein the composition includes a stabilizing agent which acts as an effective barrier to the possible degredative interaction of the peroxide and the additional therapeutic agent.

In one embodiment, the surface active agent comprises about 0.1% to about 5% by weight of a mixture of Glyceryl monostearate and PEG-40 Stearate.

In one embodiment, the composition about 1% to about 25% by weight of a polar solvent. In another embodiment, the polar solvent is selected from polyols, glycerol (glycerin), propylene glycol, hexylene glycol, diethylene glycol, propylene glycol n-alkanols, terpenes, di-terpenes, tri-terpenes, terpen-ols, limonene, terpene-ol, l-menthol, dioxolane, ethylene glycol, other glycols, sulfoxides, dimethylsulfoxide (DMSO), dimethylformanide, methyl dodecyl sulfoxide, dimethylacetamide, monooleate of ethoxylated glycerides (with 8 to 10 ethylene oxide units), azone (1-dodecylazacycloheptan-2-one), 2-(n-nonyl)-1,3-dioxolane, esters, isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, acetamide oleates, triolein; various alkanoic acids, caprylic acid; lactam compounds, azone; alkanols, dialkylamino acetates, and admixtures thereof. In another embodiment, the polar solvent is selected from polyethylene glycol (PEG), PEG200 (MW (molecular weight) about 190-210 kD), PEG300 (MW about 285-315 kD), PEG400 (MW about 380-420 kD), PEG600 (MW about 570-630 kD), PEG 4000, PEG 6000, PEG 10000 and mixtures thereof.

In another aspect, provided herein is a therapeutic kit to provide a safe and effective dosage for treating acne, including an aerosol packaging assembly comprising: (a) a container accommodating a pressurized product; and (b) an outlet capable of releasing the pressurized product as a foam; wherein the pressurized product comprises a foamable composition provided herein. In one embodiment, upon release from the container, a shear-sensitive foam, having a density range selected from (1) between about 0.02 g/mL and about 0.1 g/mL; and (2) between about 0.02 g/mL and about 0.1 g/mL, is produced.

In another aspect, provided herein is a therapeutic kit to provide a safe and effective dosage for treating acne, including an aerosol packaging assembly comprising: (a) a first container accommodating a first pressurized product; (b) a second container accommodating a second pressurized product and (b) at least one outlet capable of releasing the first pressurized product and the second pressurized product as a foam; wherein the first pressurized product comprises a foamable composition provided herein, and the second pressurized product comprises a foamable composition containing one additional therapeutic agent. In one embodiment, the additional therapeutic agent is selected from antibiotics, retinoids, keratolytics and azelaic acid (AZA). In another embodiment, the additional therapeutic agent is an antibiotic selected from the group consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroides, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds. In another embodiment, the additional therapeutic agent is clindamycin.

In another aspect, provided herein is a method of enhancing the stability of a foamable composition comprising benzoyl peroxide for treating acne, the method comprising adding a moisturizing complex to the foamable composition. In one embodiment, the moisturizing complex comprises about 5% to about 15% by weight of the total composition. In another embodiment, the moisturizing complex comprises glycerin and sodium PCA. In another embodiment, the moisturizing complex includes an oil and comprises about 5% to about 30% by weight of the total composition and at least one of glycerine and a salt of 2-pyrrolidone-5-carboxylic acid (PCA), wherein the oil comprises mineral oil and a silicone oil.

In another aspect, provided herein is a method of reducing the dryness, irritation, or both associated with the use of a foamable composition containing benzoyl peroxide for treating acne, the method comprising adding a moisturizing complex to the foamable composition. In one embodiment, the moisturizing complex comprises about 5% to about 15% by weight of the total composition. In another embodiment, the moisturizing complex comprises glycerin and sodium PCA. In another embodiment, the moisturizing complex includes an oil and comprises about 5% to about 30% by weight of the total composition and at least one of glycerine and a salt of 2-pyrrolidone-5-carboxylic acid (PCA), wherein the oil comprises mineral oil and a silicone oil.

In another aspect, provided herein is a method of making a foamable composition comprising containing a suspended solid active agent, comprising: (a) forming a prefoam emulsion comprising a solid active agent, one or more surface-active agents; about 0.001% to about 1% by weight of the total composition of at least one polymeric additive; a pH adjusting component selected to be able to gel the polymeric additive; about 5% to about 15% by weight of the total composition of a moisturizing complex; and water, wherein the aqueous phase has a thickness sufficient to suspend the active agent; (b) adding a buffer system to the prefoam emulsion to reduce the viscosity of the prefoam formulation, said buffer system at a pH that is less than that of the prefoam emulsion before addition of the buffer and is selected to provide a liquid prefoam emulsion; and (c) introducing a liquefied or compressed gas propellant at a concentration of about 3% to about 25% by weight of the total composition to the reduced viscosity prefoam emulsion to obtain a foamable composition having a stable suspended active solid and that is fluid at room temperature. In one embodiment, the prefoam emulsion has a pH in the range for 4 to 6. In another embodiment, the prefoam emulsion has a pH of less than about 5. In another embodiment, the foam produced from the foamable composition has an average bubble size of less than about 150 microns.

BRIEF DESCRIPTION OF THE DRAWINGS

The invention is described with reference to the figures which are presented for the purpose of illustration and are not intended to be limiting.

DETAILED DESCRIPTION

Figure 1:
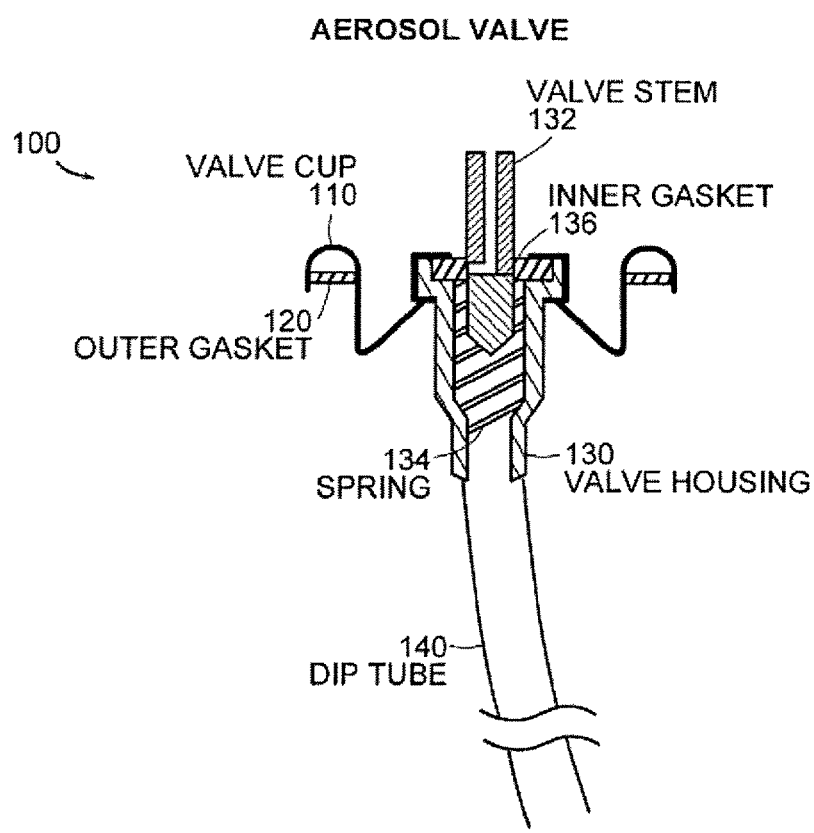
FIG. 1 is a schematic illustration of an aerosol valve suitable for use in the aerosol packaging assembly according to in one or more embodiments.

The present invention provides a foamable composition for treating acne comprising benzoyl peroxide; a therapeutic kit comprising such composition; and a method of treating acne using such composition.

Pharmaceutical Composition

All % values are provided on a weight (w/w) basis.

Benzoyl peroxide ("BPO") is commercially available or can be prepared by interaction of benzoyl chloride and a cooled solution of sodium peroxide. For laboratory procedures, see, e.g, A. I. Vogel, *Practical Organic Chemistry* (Longmans, London, $3^{rd}$ ed., 1954) p 807; Gattermann-Wieland, *Praxis des organischen Chemikers* (de Gruyter, Berlin, $40^{th}$ ed., 1961) p 115.

BPO is commonly used for one or more of the following indications acne (main indication), fungal skin infections and decubitus or stasis ulcers. It may also be of effect in alopecia areata, in progressive macular hypomelanosis (in combination with clindamyin and UVA), and in seborrheic keratoses.

BPO can also be used in combination with antibiotics. A non limiting list of antibiotics includes clindamycin phosphate, erythromycin, clindamycin, and erythromycin estolate.

BPO can also be used in combination with other drugs A non limiting list of combinations is as follows: BPO+urea; BPO+sodium hyaluronate; BPO+potassium hydroxyquinoline sulfate; BPO+hydrocortisone; BPO+sulphur; BPO+cetylpyridinium chloride; BPO+miconazole nitrate; BPO+potassium hydroxyquinoline sulfate+hydrocortisone; BPO+silver+kaolin+calcium gluconate (Katoxyn); It may also be effective as BPO+adapalene; and BPO+allylamine.

It is preferable to have an average particle size of less than about 35 microns, more preferably less than about 25 microns. In the Examples described herein the formulations are homogenized resulting in an average BPO particle size distribution of about 2 to about 24 microns, The particle size is determined by light microscope in which the level of detection is about 1 micron. Thus, particles may be present below the level of detection. The particle size can depend on one or more of, the formulation, homogenization time and quality of homogenization. The homogenizer used is a Silverson L4RT.

Foam Formulations, Breakable Foam and BPO

The term "foam" is a general term that encompasses a range of substances. Accordingly, the context in which "foam" is discussed must be examined carefully. The type and quality of the foam is of critical importance. There are many different types of foams and within each foam type there are many levels of qualities. For example, the froth on the head of beer, lather of shampoo, and lather of shaving cream have been loosely described as foam but all are different from one another. At one end of the cosmetic or pharmaceutical foam spectrum the foam can be long lasting and essentially not readily breakable like shaving foams. At the other end of the spectrum the foam can be quick breaking and collapses upon release.

Thermolabile foams are an example of type of quick breaking foam. They can contain significant amounts of thermolabile substances that aid their collapse upon being exposed to an increased temperature for example when applied to a body surface at 37 C. Upon being exposed to the higher temperature they collapse rapidly. Examples are foam formulations that comprise significant amounts of volatile solvents.

Breakable foam is a specialized type of foam. It is a low density foam that is stable on release at least in the short time span of several minutes, which facilitates application to a target area; but can break readily upon the application of shear force such as gentle rubbing to spread easily over a target surface. It is not thermolabile (and does not melt at skin temperature) and nor does it display late or long delayed expansion over minutes.

Some foams expand slowly whilst others do so quickly. Some foams foam immediately and some demonstrate delayed foaming. Some require mechanical lathering and some expulsion by propellant. Whilst they all fall under the so called term "foam" and may appear to have some common ingredients the results and properties of these products are different.

A suitable foamable formulation for a particular application may present challenges at several levels. For example, a foam formulation may require a stable pre foam formulation; a stable pre foam propellant formulation and ultimately deliverly an effective measured amount of active agent to a target. Each of these objectives poses its own unique challenges.

The pharmaceutical and cosmetic foams discussed herein are generated in general terms by manufacturing a suitable foamable carrier composition and loading the carrier in a pressurized valved canister with an appropriate propellant. Upon expelling the canister contents a foam can be released. The type, nature and quality of the foam depends inter alia on the carrier composition, the active agent, the propellant and the method of manufacture and storage. Making a stable (physically and chemically) formulation that can be stored in a canister with a propellant that remains stable and can produce a breakable foam of quality on release is far from trivial.

An additional difficulty frequently encountered with propellant foams is their inability to dispense a uniform application of the medically active ingredient throughout the use of the entire aerosol container. This is particularly due to the fact that the active material is not stably dispersed in the foamable composition so that it will have a tendency to settle to the bottom. Further, the dispersed material will sometimes clog the spray dispensing valve to further interfere with the uniform dispensing of the medicament.

The foamable composition carries BPO as solid particles in suspension and upon discharge from an aerosol container forms a breakable foam, which is rich and creamy in appearance, and shows very fine bubble structure. The foam does not break down immediately upon discharge, neither does it break down upon exposure to skin temperature. However, it collapses to spread easily and deposits BPO uniformly onto a skin area upon slight rubbing. The composition is able to hold BPO physically and chemically stable despite the fact it is of low viscosity. The composition is further able to ameliorate the irritating and drying effects of BPO and actually improves skin moisture.

BPO is an insoluble solid. It has a tendency to cake or form lumps and to sediment, which could make the product non-uniform. It is a skin irritant, and its irritation potential is concentration-dependent. It dries the skin.

In order to formulate BPO in an emulsion comprising oil droplets in water the BPO emulsion must be stabilized to prevent phase separation. Simultaneously, in order to formulate BPO as a homogenous suspension the BPO emulsion must be stabilized to prevent sedimentation and also to prevent caking at the bottom of the container or BPO aggregates. Stabilization is dependent inter alia upon counteracting repellant molecular forces, particle motion and gravity.

A method of trying to achieve these objectives is to create a formulation in which the viscosity is increased to a level (high) such that the emulsion oil globules and also the suspended BPO particles have a reduced level (low) of mobility. In practical terms this means that at the viscosity range in which a BPO emulsion formulation is determined as aforesaid to have low mobility the formulation is substantially not flowable because of the high viscosity required to achieve low mobility. This may be fine for creams and ointments but it creates a unique challenge in trying to achieve breakable foams of quality. Simply adding a miscible liquid propellant to a viscous cream or ointment—putting to one side for a moment that merely adding propellant to a cream or ointment will not of itself achieve a breakable foam of quality—the addition of propellant will cause the formulation to become diluted and the viscosity reduced. In turn the BPO will have a higher motion and be more likely to cake and to sediment and in turn the emulsion formulation will be more vulnerable to phase separation.

As can be appreciated from the above discussion, forming a homogeneous suspension of a BPO foamable formulation using an emulsion formulation with high viscosity—so that even after addition of propellant the formulation has high viscosity—in order to try and stabilize the oil droplets and BPO particles, minimize molecular motion and discourage gravitational sedimentation in the canister in which the formulation is stored simply will not do for foamable compositions. Such high viscous formulations are not desirable for foamable compositions since they have low flowability and may exhibit one or more of the following: are not shakable; form a block, i.e., a solid no flowable mass, in the canister; do not result in uniform expulsion; and if expulsed may be accompanied by unwanted phenomena such as one or more of jets, tailing and noise.

Unexpectedly it has been surprisingly discovered that it is possible to make compositions which are truly flowable and have low viscosity in which the propellant forms part of the oil phase of the emulsion formulation but nevertheless surprisingly does not make the formulation substantially vulnerable to phase separation and or sedimentation. Moreover these compositions are stable and are able to form breakable foam of quality that spreads easily and is able to deliver an effective and measurable amount of active agent homogeneously to a target surface.

One key element is the polymeric agent used in the formulation. The polymeric agent can contribute to the stability and stabilization of the formulation. Concentrations of polymeric agents and other thickeners have in the past been used to achieve very high viscosities of at least 20,000 centipoises (cps) to a million or more cps. Surprisingly, it has been unexpectedly found that by using low viscosities of the order of about 7000 to about 8000 cps or less for the pre-foam formulation whose viscosity is further reduced upon inclusion of propellant it has been possible to achieve a stable BPO formulation that produces breakable (non thermolabile) foam of good quality even after addition of propellant and even though the foamable formulation with propellant is fluid and easily shakable. In a preferred embodiment the viscosity of a formulation comprising propellant is below about 5000 cps and in a more preferred embodiment it is below about 3000 cps. At such low levels of viscosity, one would expect a suspended solid active agent such as BPO to precipitate out of solution. In the low viscosity formulations provided herein, BPO unexpectedly remains homogeneously dispersed in suspension. For pharmaceutical applications, BPO needs to be homogeneous to ensure that the amount of BPO in the first dose and the last dose.

An important factor in the use of a polymeric agent is to ensure the polymer(s) is appropriately and correctly swelled in the presence of water by adding an effective amount of base. Without being bound by any theory it may be the case that the lower levels of polymeric agent still form a semi water gel like infrastructure that unexpectedly is able to stabilize the BPO physically and chemically at low viscosities.

In an embodiment the polymer is an amphphilc polymer, such as, an acrylates/C10-30 alkyl acrylate crosspolymer The hydrophilic and hydrophobic regions of these polymers serve to interact with and stabilize hydrophilic and lipophilic components, respectively, of a composition. In one embodiment the polymeric agent is a carbomer.

By way of example, suitable polymeric surfactants include cross linked copolymers of acrylic acid and a hydrophobic comonomer, such as Pemulen TR-1 and Pemulen TR-2, ETD 2020 and Carbopol 1382 (all, Acrylates/C10-30 alkyl acrylate crosspolymer), Natrosol CS Plus 330 and 430 and Polysurf 67 (all, cetyl hydroxyethyl cellulose), Aculyn 22 (acrylates/steareth-20 methacrylate copolymer), Aculyn 25 (acrylates/laureth-25 methacrylate copolymer), Aculyn 28 (acrylates/beheneth-25 methacrylate copolymer), Aculyn 46 (PEG-150/stearyl alcohol/SMDI copolymer), Stabylen 30 (acrylates/vinyl isodecanoate), Structure 2001 (acrylates/steareth-20 itaconate copolymer), Structure 3001 (acrylates/ceteth-20 itaconate copolymer) and Structure Plus (acrylates/aminoacrylates/C10-30 alkyl PEG 20 itaconate copolymer), where PEG is polyethylene glycol, PPG is polypropylene glycol.

Other exemplary amphiphilic copolymers include silicone polymers such as amphiphilic silicone polyols or copolyol, for example cetyl dimethicon copolyol and dimethicone copolyol PPG-3 oleyl ether, acetylated starch derivatives, amphiphilic modified starches, and amphiphilic block copolymers of ethylene oxide, propylene oxide and/or propylene glycol (also known as "poloxamer").

The gelling agent may include other types of gelling agents, in combination with an amphiphilic copolymer. A non limiting list of other types such as water soluble cellulose, or gums like guar and xantham is provided below.

On comparing different polymers and combinations of polymers it was noted that whilst formulations with non ampiphilic polymers like methocel and xantham produced homogenous BPO formulations, nevertheless such formulations separated over time albeit reversibly such that homogeneity was seen to be restored on shaking. In contrast these formulations with the addition of relatively low levels of ampiphilic polymer carbopol were found to be homogenous over time.

The comparative analysis of Example 24 showed that carbapol was better than pemulen was better than xanthan. It is difficult to try and explain why in a fluid hydrocarbon low viscosity medium one polymer is better than another. Moreover, it is completely unexpected that in a fluid viscous emulsion medium carbopol can hold the BPO in a homogenous distribution even after six months.

A further element and aid to reducing viscosity in the presense of gelling agents is the use of a buffer or buffer complex. It was observed that when small amounts of citrate buffer or alternatively lactate buffer was added to the carbomer gel it results in a viscous liquid. Thus, the presence of citrate or lactate buffer was noted to cause a thick emulsion gel or paste containing carbomer to become fluid. Other similar buffers may work. Non limiting examples of appropriate possible buffers, which may achieve the same objective are acetate, malate, sorbate, succinate and tartrate. As is explained below and as is seen in the Examples when the acid of the buffer is added first this alone can break the gel. Thus, in one or more embodiments when a buffer is added it is added sequentially. In other embodiments it is added simultaneously as a stock solution. In further embodiments a pH adjuster is added.

A further element and complication is that in certain circumstances it has been observed that the propellant itself can cause the BPO to chemically degrade. Therefore it is not sufficient to merely dilute the formulation with propellant but the formulation must also be formulated such that the BPO remains substantially un-degraded following application of propellant and its absorption into the oil phase of the emulsion.

According to one aspect, a foamable composition is provided for treating acne comprising: (a) a prefoam emulsion composition comprising: i. benzoyl peroxide; ii. one or more surface-active agents; iii. about 0.001% to about 1% by weight of the total composition of at least one polymeric additive; and iv. water; (b) up to about 2% by weight of the total composition of a buffer system, wherein the buffer system is selected to provide a viscosity of the prefoam composition of less than about 8000 centipoises (cps) at room temperature; and (c) a liquefied or compressed gas propellant at a concentration of about 3% to about 25% by weight of the total composition, wherein the viscosity of the foamable composition is less than about 8000 centipoises (cps) at room temperature. In one embodiment, the foam produced from the foamable composition has an average bubble size of less than about 150 microns.

In certain embodiments, the composition further comprises about 5% to about 15% a moisturizing complex comprising glycerine and a salt of 2-pyrrolidone-5-carboxylic acid (PCA). In some cases, the composition further comprises about 5% to about 30% of a moisturizing complex comprising an oil and at least one of glycerine and a salt of 2-pyrrolidone-5-carboxylic acid (PCA), wherein the oil comprises mineral oil and a silicone oil. In other embodiments, the moisturizing complex has at least three of the following characteristics: (a) improves the chemical stability of BPO in the composition; (b) improves the homogeneity of BPO in the composition; (c) improves the quality of the foam produced from the foamable propellant composition; (d) improves the hydration of skin after 7 hours by at least about 20%.

In certain embodiments, the composition described hereinabove may further comprise at least one organic carrier at least one organic carrier selected from the group consisting of a hydrophobic organic carrier, an organic polar solvent, an emollient and mixtures thereof, at a concentration of about 2% to about 50% by weight. In some cases, the at least one organic carrier is present in an amount selected from the group consisting of (i) about 2% to about 5%; (ii) about 5% to about 10%; (iii) about 10% to about 20%; and (iv) about 20% to about 50% by weight.

In certain embodiments, the composition described hereinabove may further comprise about 0.1% to about 5% by weight of a therapeutically active foam adjuvant is selected from the group consisting of fatty alcohols having 15 or more carbons in their carbon chain; fatty acids having 16 or more carbons in their carbon chain; fatty alcohols derived from beeswax and including a mixture of alcohols, a majority of which has at least 20 carbon atoms in their carbon chain; fatty alcohols having at least one double bond; fatty acids having at least one double bond; branched fatty alcohols; branched fatty acids; fatty acids substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid and mixtures thereof.

In other embodiments, the composition comprises at least one additional therapeutic agent, which is an antibiotic agent, selected from the group consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroides, sulfonamides, tetracycline, lincomycin class, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof, and naturally occurring antibiotic compounds. In one embodiment, the antibiotic is clindamycin.

In certain embodiments, the concentration range of benzoyl peroxide is selected from the group of (i) between about 0.005% and about 0.5%; (ii) between about 0.5% and about 2%; (iii) between about 2% and about 5%; (iv) between about 5% and about 10%; and (v) between about 10% and about 15%. In certain other embodiments, the concentration of the surface-active agent is between about 0.1% and about 5%.

In another aspect, a foamable composition is provided, comprising: (a) a prefoam composition comprising: i. a suspended solid active agent; ii. one or more surface-active agents; iii. about 0.001% to about 1% by weight of the total composition of at least one polymeric additive; iv. up to about 2% by weight of the total composition of a buffer system; and v. water, wherein the viscosity of the prefoam composition is less than about 8000 centipoises (cps) at room temperature; and (b) a liquefied or compressed gas propellant at a concentration of about 3% to about 25% by weight of the total composition, wherein the viscosity of the foamable composition is less than about 8000 centipoises (cps) at room temperature.

In another aspect, a foamable composition is provided, comprising: (a) a prefoam composition comprising: i. a suspended solid active agent; ii. one or more surface-active agents; iii. about 0.001% to about 1% by weight of the total composition of at least one polymeric additive; iv. about 5% to about 15% by weight of the total composition of a moisturizing complex; and v. water; (b) up to about 2% by weight of the total composition of a buffer system, wherein the buffer system is selected to provide a prefoam composition that is fluid at room temperature; and (c) a liquefied or compressed gas propellant at a concentration of about 3% to about 25% by weight of the total composition, wherein the foamable propellant composition is fluid at room temperature.

In one embodiment, the foam produced from the foamable propellant composition has an average bubble size of less than about 150 microns.

In one embodiment, the suspended solid agent has an average particle size of less than about 35 microns.

In one embodiment, the buffer system comprises citric acid and sodium citrate or lactic acid and ammonium lactate.

In one embodiment, the composition further comprises about 5% to about 15% a moisturizing complex comprising glycerine and a salt of 2-pyrrolidone-5-carboxylic acid (PCA). In another embodiment, the composition further comprises about 5% to about 30% of a moisturizing complex comprising an oil and at least one of glycerine and a salt of 2-pyrrolidone-5-carboxylic acid (PCA), wherein the oil comprises mineral oil and a silicone oil.

In certain embodiments, the polymeric agent includes, but not limited to, a water-soluble polymer, a water-insoluble polymer, a gelling agent, an inorganic gelling agent, a mucoadhesive macromolecule and a film forming polymer. In certain other embodiments, the water-soluble polymer includes, but not limited to, methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose, carboxymethylhydroxyethylcellulose, xanthan gum, guar gum, carrageenin gum, locust bean gum and tragacanth gum.

In one embodiment, the polymeric additive comprises an amphiphilic polymer. In another embodiment, the amphiphilic polymeric additive comprises a carbomer. In another embodiment, the polymeric additive further comprises a polymeric agent selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose, Sodium CMC, carboxymethylhydroxyethylcellulose, xanthan gum, guar gum, carrageenin gum, locust bean gum and tragacanth gum and mixtures of two or more thereof.

In certain embodiments, the composition described herein above may further contain a penetration enhancer. In some cases, the penetration enhancer includes, without Illumination, propylene glycol, butylene glycols, hexylene glycol, glycerol, pentaerythritol, sorbitol, mannitol, oligosaccharides, dimethyl isosorbide, monooleate of ethoxylated glycerides having about 8 to 10 ethylene oxide units, polyethylene glycol 200-600, transcutol, glycofurol and cyclodextrins.

In certain embodiments, the composition described herein above may further contain the composition further comprises a pH adjusting agent (or a pH adjuster). In some cases, the pH adjusting agent is selected from an acid, a base and a buffering agent. In some other cases, the pH adjusting agent is selected from citric acid, sodium citrate and mixtures thereof. In certain embodiments, the pH of the foamable composition is between about 3.0 and about 7.0, for example, about 3.0, about 3.5, about 4.0, about 4.5, about 5.0, about 5.5, about 6.0, about 6.5 and about 7.0. In certain other embodiments, the pH of the foamable composition is between about 3.0 and about 6.0. In certain other embodiments, the pH of the foamable composition is between about 4.0 and about 7.0. In certain other embodiments, the pH of the foamable composition is between about 4.0 and about 5.0.

In some embodiments, the prefoam emulsion composition further comprises a pH adjusting component selected from the group consisting of, a base or a buffer system, said pH adjusting component selected to be able to gel the polymeric additive. In other embodiments, the pH of the prefoam emulsion composition is between about 4.0 and about 6.0. In some cases, the buffer system is at a pH less than the pH of the prefoam emulsion before addition of the buffer and is selected to provide a liquid prefoam emulsion. In other embodiments, the buffer system comprises citric acid and sodium citrate or lactic acid and ammonium lactate.

A pH adjuster includes buffer but a buffer does not necessarily include a pH adjuster. A pH adjuster can be, for example, an acid alone or an acidic agent alone or a base alone or a basic agent alone or a buffer. A simple buffer is a solution which resists change of pH upon addition of small amounts of acid or base, or upon dilution. It is an aqueous solution consisting of a mixture of a weak acid and its conjugate base or a weak base and its conjugate acid. In some case the buffer can be a biological buffer such as Tris. In the Examples herein a buffer primarily comprises an acid and its salt (for example, citric acid/sodium citrate). The buffer can be used to bring the formulation to a desired pH and is designed to maintain the pH at the desired pH so that the pH remains substantially unchanged when a composition is exposed to small amounts of acidic or basic substances. In the absence of buffer the same composition may have shown a significant pH change.

Polymeric agents used to form gels have different sensitivities to changes in pH. For example, methocel and xantham gum are not expected to be sensitive to pH changes, whereas carbopols are sensitive to pH. Carbopols obtained from one manufacturer may have a different sensitivity range than that obtained from a different manufacturer. Thus, it is important to look at what the manufacturer says about its product. The carbopols used in the Examples provided herein were obtained from Noveon. The pH sensitivity appears to be reversible. When buffer is added to the gel, there is a small reduction in pH but this appears to destroy the carbomer matrix and turn the gel into a liquid. In fact when the acid component of the buffer is added first this was seen to destroy the gel. As such, it is expected that addition of any acids that can reduce the pH of the formulation to below about pH 4 would have this effect. Thus, buffers can break the gel, and acids alone can also be expected to break the gel. Non-limiting examples of acids include alpha hydroxyl acid, an aliphatic beta hydroxyacid, an aromatic acid, an aromatic hydroxyl acid, an alpha ketoacid, an aliphatic carboxylic acid, a branched aliphatic carboxylic acid, a short chain carboxylic acid, a fatty acid, an omega-3 fatty acid, an omega-6 fatty acid, an omega-9 fatty acid, a dicarboxylic acid, a branched dicarboxylic acid, an unsaturated dicarboxylic acid, an amino acid and a dimer or oligomer of amino acids. For the acid to have an appropriate effect it is envisaged that it should be miscible in water. If the acid has low or poor miscibility its effect will be reduced, although incorporating it into an aqueous emulsion may help.

In one embodiment, the concentration of the one or more surface-active agents is between about 0.1% and about 5%. In another embodiment, the surface-active agent is selected from the group consisting of Steareth-21, Steareth-2, steareth 20, Polysorbate 80, Polysorbate 60, Polysorbate 20, ceteth 20, PEG 40-stearate, PEG 100-stearate, PEG-30 dipolyhydroxystearate, sorbitan stearate (span 60), sorbitan palmitate (span 40), sorbitan laurate (span 20), sorbitan monooleate (span 80), glycerol monostearate, glyceryl stearate, laureth 4, ceteareth 20, macrogol cetostearyl ether, ceteth 2 (Lipocol C-2), sucrose distearate (Sisterna SP30), polyoxyethylene (100) stearate, and mixtures thereof.

In certain other embodiments, the surfactant is selected from Steareth-21, Steareth-2, Polysorbate 60, and mixtures thereof. In certain embodiments, the foam adjuvant is Stearyl alcohol. In certain other embodiments, the emollient or emulsifier is Glyceryl monostearate or PEG-40 Stearate. In certain embodiments, the gelling agent is selected from Sodium CMC, Xanthan gum, Methocel K100, and mixtures thereof. In certain other embodiments, the pH adjusting agent is present and is selected from an acid, a base and a buffering agent. In certain embodiments, the pH adjusting agent is selected from citric acid, sodium citrate and mixtures thereof. In certain other embodiments, the moisturizing complex comprises glycerin and sodium PCA.

In certain embodiments of this aspect, the gelling agent is selected from acrylates/C10-30 alkyl acrylate crosspolymer, a carbomer, xanthan, Methocel (hydroxypropyl methyl cellulose), sodium carboxmethylcellulose ("CMC"), Klucel (hydroxypropylcellulose) and mixtures thereof. According to various embodiments the agent or mixtures thereof are selected to achieve a viscosity of less than about 8000 cps, which is preferably less than 6000 cps and more preferably less than about 3000 cps after addition of propellant.

In certain embodiments of this aspect, the surfactant is selected from Polysorbate 60, Polysorbate 20, sorbitan laurate (span 20), and mixtures thereof. In certain other embodiments, the film forming agent comprises Klucel EF.

In certain embodiments of this aspect, the film forming agent comprises Klucel EF. In certain other embodiments, the oil comprises Jojoba oil. Jojoba oil (pronounced "ho-HO-bah") is the liquid wax produced in the seed of the Jojoba (*Simmondsia chinensis*) plant. Jojoba oil is a straight chain wax ester, 36 to 46 carbon atoms in length. Each molecule consists of a fatty acid and a fatty alcohol joined by an ester bond. Each molecule has two points of cis-unsaturation, both located at the 9th carbon atom from either end of the molecule. Jojoba oil comprises approximately 66-71% eicosenoic acid, 14-20% docosenoic acid and 10-13% oleic acid. Refined jojoba oil is colorless and odorless. The melting point of jojoba oil is approximately 10° C. Jojoba oil is relatively shelf-stable when compared with other vegetable oils. Unlike common vegetable oils, jojoba oil is chemically very similar to human sebum. Most jojoba oil is used as an ingredient in cosmetics and personal care products, especially skin care and hair care. Therapeutically it can aid in the healing process.

In certain embodiments of this aspect, the oil comprises silicone. Non-limiting examples of silicone include dimethicone, cyclomethicone, polyalkyl siloxane, polyaryl siloxane, polyalkylaryl siloxane, a polyether siloxane copolymer and a poly(dimethylsiloxane)-(diphenyl-siloxane) copolymer. In one embodiment, the oil is volatile. In an embodiment, the volatile silicone is cyclic, such as, cyclomethicone.

In certain embodiments of this aspect, the polar solvent is selected from polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, l-menthol, dioxolane, ethylene glycol, other glycols, sulfoxides, such as dimethylsulfoxide (DMSO), dimethylformanide, methyl dodecyl sulfoxide, dimethylacetamide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

In certain other embodiments of this aspect, the polar solvent is selected from polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof. In certain embodiments of this aspect, the polar solvent is propylene glycol. In certain embodiments, the film forming agent is Klucel EF. In certain other embodiments, the surfactant is selected from Polysorbate 60, Polysorbate 20, Ceteth 20, sorbitan laurate (span 20), PEG 100-stearate, and mixtures thereof. In certain embodiments, the foam adjuvant comprises stearyl alcohol.

In certain embodiments of this aspect, the surfactant comprises polysorbate 60. In certain other embodiments, the foam adjuvant comprises stearyl alcohol. In some cases, the gelling agent comprises sodium CMC.

In certain embodiments, the foamable composition described hereinabove may further comprise at least one additional therapeutic agent, which is an antibiotic agent, selected from the group consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroides, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds.

In certain embodiments, the additional antibiotic is an antibiotic of the lincomycin family. In one embodiment, the antibiotic is clindamycin.

In certain embodiments, the foamable composition described hereinabove may further include at least one additional therapeutic agent selected from the group consisting of an a steroidal anti-inflammatory agent, an immunosuppressive agent, an immunomodulator, an immunoregulating agent, a hormonal agent, an androgen, an estrogen, a prostaglandin, an antiandrogen agent, a testosterone inhibitor, a dihydrotestosterone inhibitor, an antifungal agent, an antiviral agent, an antiparasitic agent, a retinoid, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, a keratolytic agent, urea, a urea derivative, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, an organo-metallic compound, and organoboron compound, an organo-berrilium compound, talc, carbon, an anti wrinkle agent, a skin whitening agent, a skin protective agent, a masking agent, an anti-wart agent, a refatting agent, a lubricating agent and mixtures thereof.

In certain embodiments, the additional therapeutic agent is sensitive to oxidation and wherein the composition includes a stabilizing agent which acts as an effective barrier to the possible degrative interaction of the peroxide and the additional therapeutic agent.

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable solvents or polar solvents due to their skin-irritating effect. This disadvantage is particularly meaningful in the case of an antibiotic treatment, which is often directed to open wounds and damaged skin and mucosal tissues. Thus, in one or more embodiments, the composition is substantially alcohol-free and includes less than about 5% final concentration of lower alcohols, preferably less than about 2%, more preferably less than about 1%.

In one or more embodiments, the concentration of surface-active agent about 0.1% to about 5%, or from about 0.2% to about 2%.

Aerosol Packaging Assembly

The aerosol packaging assembly typically includes a container suitable for accommodating a pressurized product and an outlet capable of releasing a foam. The outlet is typically a valve. FIG. 1 illustrates a typical aerosol valve 100. The valve is made up of the valve cup 110 typically constructed from tinplated steel, or aluminum, an outer gasket 120, which is the seal between the valve cup and the aerosol can (not shown), a valve housing 130, which contains the valve stem 132, spring 134 and inner gasket 136, and a dip tube 140, which allows the liquid to enter valve. The valve stem is the tap through which the product flows. The inner gasket 136 covers the aperture 150 (hole) in the valve stem. The valve spring 134 is usually made of stainless steel.

The valve stem is fitted with small apertures 150 (also termed "orifices" and "holes"), through which the product flows. Valves may contain one, two, three, four or more apertures, depending on the nature of the product to be dispensed. In the closed position, the aperture(s) is covered by the inner gasket. When the actuator is depressed it pushes the valve stem through the inner gasket, and the aperture(s) is uncovered, allowing liquid to pass through the valve and into the actuator.

The valve can have a stem with 1 to 4 apertures, or 1 to 2 apertures. Each aperture can have a diameter of about 0.2 mm to about 1 mm, or a diameter of about 0.3 mm to about 0.8 mm. The total aperture area, i.e., the sum of areas of all apertures in a given stem, is between about 0.01 mm² and 1 mm² or the total aperture area is between about 0.04 mm² and 0.5 mm².

In order to provide proper therapy, precise dosing is desired. According to one or more embodiments, the valve is attached, directly, or through a tube, to a metered dose device, which for dispensing an accurate dose of drug in the form of a foam. The metered dose valve is selected to release a foam in a volume that provides an adequate therapeutic dose to the target site of the skin, a body surface, a body cavity or mucosal surface, e.g., the mucosa of the nose, mouth, eye, ear, respiratory system, vagina or rectum.

In one or more embodiments, the meter dose valve provides a unit dose of between about 10 µL and about 1000 µL. Assuming a representative foam density (specific gravity) of 0.06 g/mL, a 10 µL valve provides a volume of about 0.17 mL of foam, and a 1000 µL metered dose valve provides about 17 mL of foam. Thus, by selecting a specific metered dosing valve and adjusting the foam density by fine tuning formulation parameters and adjusting the ratio between the liquid components of the composition and the propellant, one can design an adequate dosage form according to the specific target site. Exemplary metered dose devices may be found in co-pending application Ser. No. 11/406,133, entitled "Apparatus and Method for Releasing a Measured Amount of Content from a Container," filed Apr. 18, 2006, which is hereby incorporated in its entirety by reference.

According to one aspect, a therapeutic kit is provided to afford a safe and effective dosage for treating acne, including an aerosol packaging assembly comprising:
 (a) a container accommodating a pressurized product; and
 (b) an outlet capable of releasing the pressurized product as a foam;
wherein the pressurized product comprises a foamable composition.

In certain embodiments of this aspect, the kit produces a shear-sensitive foam having a density range selected from between about 0.02 gr/mL and about 0.1 gr/mL upon release from the container.

According to another aspect, the aerosol packaging assembly may include two containers suitable for contemporaneously mixing and/or combining two foamable compositions. In some cases, the aerosol packaging assembly comprises:
 a. a first container accommodating a first pressurized product;
 b. a second container accommodating a second pressurized product and
 c. at least one outlet capable of releasing the first pressurized product and the second pressurized product as a foam;
wherein the first pressurized product comprises a foamable composition according to claim 1, and the second pressurized product comprises a foamable composition containing one additional therapeutic agent.

In certain embodiments of this aspect, the additional therapeutic agent is selected from antibiotics, retinoids, keratolytics and azelaic acid(AZA). In certain other embodiments, the additional therapeutic agent is an antibiotic selected from the group consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds. In some cases, the additional therapeutic agent is clindamycin.

Figure 2:
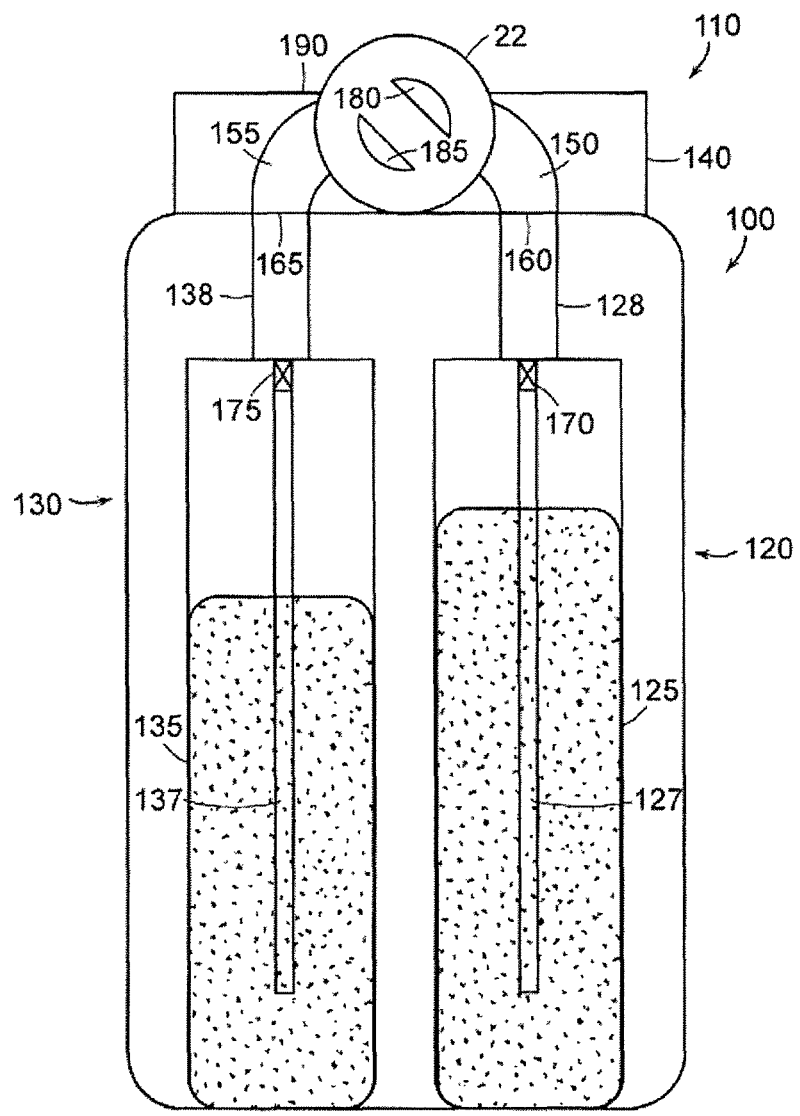
FIG. 2 is a cross sectional view of an apparatus for substantially contemporaneously releasing, mixing and/or combining at least two foamable compositions measure of content from at least two containers.

US 2007/0069046 describes a therapeutic kit for releasing a predetermined quantity of a foamable composition from a plurality of pressurized containers, which is incorporated herein by its entirety. FIG. 2 shows a kit 100 including a dispenser head engaged with a pair of pressurized containers 120, 130.

In one embodiment, FIG. 2 shows in cross-section a kit 100 including a dispenser head 110 mounted on two containers 120 and 130 containing contents 125 and 135 for dispensing and mixing. The dispenser head and the containers are accommodated in a housing. The dispenser head 110 includes a flow guide 140, which also functions as an actuator. Flow guide 140 houses a flow conduits 150, 155, whose function is described in greater detail below. The cross-sectional area of each conduit may be the same or different. The container contents include a foamable composition that is flowable, e.g., a fluid, a liquid and a semi-liquid. Container 120 has stem 128 that extends from container 120 and engages with fluid conduit at an inlet 160. Similarly, container 130 has stem 138 that extends from container 130 and engages with fluid conduit at an inlet 165.

Each container 120 or 130 in the embodiment described is of the pressurized aerosol can type and has its own internal valve (170, 175) fitted with a valve stems 128, 138, respectively. Container 120 includes a hollow tube 127 that is attached to or integrally formed with, a internal valve 170, thereby readily facilitating flow of liquids, fluids and gas through tube 127 through valve 170 and into stem 128. The stem 128 is hollow and depressing the stem opens the valve so that the container contents are dispensed through the hollow stem. Similarly, container 130 includes a hollow tube 137 that is attached to or integrally formed with, a internal valve 175, thereby readily facilitating flow of liquids, fluids and gas through tube 137 through valve 175 and into stem 138. The stem 138 is hollow and depressing the stem opens the valve so that the container contents are dispensed through the hollow stem. The valve in some types of containers includes a return spring for returning the stem to its initial position so as to close the valve when the force depressing the stem is removed.

Flow guide 140 has a pair of flow conduits 150, 155, each defined by a tubular wall having an inlet 160, 165, respectively, and an outlet 180, 185, respectively. Inlets 160, 165 of flow conduits 150, 155 abut of the upper ends of stems 128, 138 respectively, when the containers 120, 130 are fully mounted on the dispenser head 140. When the flow conduits 150, 155 are in place in the flow guide 140, outlets 160, 165 are positioned coaxial with the respective container stems 128, 138.

The foamed material exits from outlets 180, 185, where it is combined and/or mixed. The position and location of the outlets can be adjusted to obtain the desired degree of combining and/or mixing. Because the individual foamed components do not mix inside the dispenser head, the foam is able to expand to its optimal extent. Furthermore, the outlets are positioned to achieve a reasonable, good or high degree of combination/mixing/interaction without loss or substantial loss of foam quality.

The dispenser head of the current invention is advantageous compared to the prior art dispensing apparatus, in which some mixing occurs within the apparatus and/or end nozzles attached to the apparatus, thereby resulting in contamination and/or requiring disposal of the end nozzles and/or cleaning of some or all of the apparatus.

The dispenser assembly 140 is used as follows. The user attaches appropriate containers 120, 130 onto the dispensing head. The containers may contain the some or different contents. In one or more embodiments, the contents may include a cosmetic and/or pharmaceutical carrier, and/or an active agent. The carrier may be in each of the containers, or may be obtained upon mixing of the contents of two or more containers. In one embodiment, one or more containers may include a cosmetic and/or pharmaceutical carrier and an additional container may include an active therapeutic or cosmetic agent. To start dispensing the container contents, the user activates the valve stems, causing the flow conduits 150, 155 to move down, thereby pressing the stems 128, 138 downward and opening the valves 170, 175 of containers 120, 130, respectively. In this embodiment, activation occurs by pressing on an upper surface 190 of the Flow guide to displace the flow guide towards the stems.

Alternatively, a separate member of the dispensing head may serve as the actuator, so that when the user presses against an upper surface of the dispenser, the dispenser head is displaced downwards and against the upper stems of the containers. Other levers, buttons or switches may be provided to actuate the kit.

When the actuator is at rest, stems valves 170, 175 are sealed, causing the container contents to remain in the pressurized containers 120, 130. When the actuators is activated, the stem 128, 138 are pressed downwards causing stem valves 170, 175 to open and the container contents to be released. The contents flows through stems 128, 138 to inlets 160, 165 and into flow conduits 150, 155. The contents then reaches outlets 180, 185, so as to be dispensed.

Thus, the flow guide includes a plurality of exit ducts that release foamed content from their respective containers such that the contents are substantially contemporaneously mixed and/or combined at a location external to the flow guide.

By a location external, this means at an area or space that is at a point of exit, that is at a point of reference just or somewhat beyond the point or exit or that is at a point of reference just before a point of exit (for example, the latter may apply where the ends of the exit conduits are formed at an angle).

It is also envisaged that one of the containers can be a non aerosol mechanical foamer. By way of a non-limiting example only, such a non aerosol mechanical first foamer container can include non aerosol mechanical foamers as disclosed in any of U.S. Pat. No. 4,018,396; U.S. Pat. No. 4,440,320; U.S. Pat. No. 4,603,812 and U.S. Pat. No. 4,738,396 all of which are hereby incorporated in their entirety by reference. So in an embodiment there is provided a dual canister configuration in which one of the canisters is a propellant driven system and one of the canisters is a mechanical driven system.

In an embodiment where it is intended that the canisters and head are to be operated in an inverse position, the hollow tubes 127,137 of FIG. 2 may be provided inverted substantially in the shape of a "U" wherein the inlet end of the hollow tubes 127,128 for the composition is submerged below the surface of the composition when the canister is inverted.

The dispensing head may be detachable from the canisters, or it may be permanently attached. In detachable embodiments, outlets 160, 165 abut or sealably contact container stems 128, 138, respectively. In disposable embodiments, outlets 160, 165 may be integral with container stems 128, 138, respectively.

Antibiotic Agents

In some embodiments, the composition or kit includes an active agent, such as antibiotics. In the context herein, an antibiotic agent is a substance that has the capacity to inhibit the growth of or to destroy bacteria and other microorganisms. In one or more embodiments the antibiotic agent is used in combination with BPO. Where the agent is compatible with BPO they can be presented in the same formulation in the same canister. Where the antibiotic agent destabilizes BPO then the other agent can be presented using a dual chamber delivery system or kit like that described above. Thus, in one embodiment BPO is presented in a first foamable formulation and stored in a first canister and the agent in a second foamable formulation and stored in a second canister. Upon release from the dual canister system the two foams are simultaneously expelled and can be delivered to a target site.

In one or more embodiments, the antibiotic agent is selected from the classes consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds. A non limiting list of antibiotics includes clindamycin phosphate, erythromycin, clindamycin and erythromycin estolate.

Oxidizing agents and substances that release free radicals and/or active oxygen. In one or more embodiments, the antibiotic agent comprises strong oxidants and free radical liberating compounds, such as oxygen, hydrogen peroxide, elemental halogen species, as well as oxygenated halogen species, bleaching agents (e.g., sodium, calcium or magnesium hypochloride and the like), perchlorite species, iodine and iodate. Organic oxidizing agents are also included in the definition of "oxidizing agent" according to the present invention, such as quinones. Such agents possess a potent broad-spectrum activity.

Additional non-limiting examples of combinations of an antibiotic agent and an additional active agent are provided in the following table:

| Disorder | Exemplary Additional Active Agent |
|---|---|
| acne | At least one agent selected from the group consisting of a retinoid; a keratolytic acid, an alpha-hydroxy acid and derivatives thereof, a beta-hydroxy acid and derivatives thereof, a skin-drying agent, an anti-seborrhea agent, a corticosteroid and a non-steroidal anti-inflammatory agent. |

| Disorder | Exemplary Additional Active Agent |
|---|---|
| Rosacea | At least one agent selected from the group consisting of a retinoid; a keratolytic acid, an alpha-hydroxy acid, a beta-hydroxy acid and derivatives thereof. |
| Otitis | At least one agent selected from the group of an antifungal agent, a local anesthetic agent, a corticosteroid and a non-steroidal anti-inflammatory agent. |
| Psoriasis | At least one agent selected from the group consisting of a corticosteroid, coal tar, anthralin and a photodynamic therapy agent |

Hence, in many cases, the inclusion of an additional therapeutic agent in the foamable composition, contributes to the clinical activity of the antibiotic agent. Thus, in one or more embodiments, the foamable composition further includes at least one additional therapeutic agent, in a therapeutically effective concentration.

In one or more embodiments, the at least one additional therapeutic agent is selected from the group consisting of a steroidal anti-inflammatory agent, a nonsteroidal anti-inflammatory drug, an immunosuppressive agent, an immunomodulator, an immunoregulating agent, a hormonal agent, an antifungal agent, an antiviral agent, an antiparasitic agent, a vasoactive agent, a vasoconstrictor, a vasodilator, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, an antibiotic agent, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and mixtures thereof.

In certain cases, the disorder to be treated involves unaesthetic lesions that need to be masked. For example, rosacea involves papules and pustules, which can be treated with an antibiotic agent, as well as erythema, telangiectasia and redness, which partially respond to treatment with an antibiotic agent. Thus, in one or more embodiments, the additional active agent is a masking agent, i.e., a pigment. Non limiting examples of suitable pigments include brown, yellow or red iron oxide or hydroxides, chromium oxides or hydroxides, titanium oxides or hydroxides, zinc oxide, FD&C Blue No. 1 aluminum lake, FD&C Blue No. 2 aluminum lake and FD&C Yellow No. 6 aluminum lake.

The foamable composition can be an emulsion, or microemulsion, including an aqueous phase and an organic carrier phase. The organic carrier is selected from a hydrophobic organic carrier (also termed herein "hydrophobic solvent"), an emollient, a polar solvent, and a mixture thereof. The identification of a "solvent", as used herein, is not intended to characterize the solubilization capabilities of the solvent for any specific active agent or any other component of the foamable composition. Rather, such information is provided to aid in the identification of materials suitable for use as a carrier in the foamable compositions described herein.

Hydrophobic Organic Carrier

A "hydrophobic organic carrier" as used herein refers to a material having solubility in distilled water at ambient temperature of less than about 1 gm per 100 mL, more preferable less than about 0.5 gm per 100 mL, and most preferably less than about 0.1 gm per 100 mL. It is liquid at ambient temperature. The identification of a hydrophobic organic carrier or "hydrophobic solvent", as used herein, is not intended to characterize the solubilization capabilities of the solvent for any specific active agent or any other component of the foamable composition. Rather, such information is provided to aid in the identification of materials suitable for use as a hydrophobic carrier in the foamable compositions described herein.

In one or more embodiments, the hydrophobic organic carrier is an oil, such as mineral oil. Mineral oil (Chemical Abstracts Service Registry number 8012-95-1) is a mixture of aliphatic, naphthalenic, and aromatic liquid hydrocarbons that derive from petroleum. It is typically liquid; its viscosity is in the range of between about 35 CST and about 100 CST (at 40° C.), and its pour point (the lowest temperature at which an oil can be handled without excessive amounts of wax crystals forming so preventing flow) is below 0° C. The hydrophobic organic carrier does not include thick or semi-solid materials, such as white petrolatum, also termed "Vaseline", which, in certain compositions is disadvantageous due to its waxy nature and semi-solid texture.

According to one or more embodiments, hydrophobic solvents are liquid oils originating from vegetable, marine or animal sources. Suitable liquid oil includes saturated, unsaturated or polyunsaturated oils. By way of example, the unsaturated oil may be olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils or mixtures thereof, in any proportion.

Suitable hydrophobic solvents also include polyunsaturated oils containing poly-unsaturated fatty acids. In one or more embodiments, the unsaturated fatty acids are selected from the group of omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). Such unsaturated fatty acids are known for their skin-conditioning effect, which contribute to the therapeutic benefit of the present foamable composition. Thus, the hydrophobic solvent can include at least 6% of an oil selected from omega-3 oil, omega-6 oil, and mixtures thereof. In the context herein, oils that possess therapeutically beneficial properties are termed "therapeutically active oil".

Another class of hydrophobic solvents is the essential oils, which are also considered therapeutically active oil, which contain active biologically occurring molecules and, upon topical application, exert a therapeutic effect, which is conceivably synergistic to the beneficial effect of the antibiotic agent in the composition.

Another class of therapeutically active oils includes liquid hydrophobic plant-derived oils, which are known to possess therapeutic benefits when applied topically.

Silicone oils (discussed earlier) also may be used and are desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers. These are chosen from cyclic or linear polydimethylsiloxanes containing from about 3 to about 9, preferably from about 4 to about 5, silicon atoms. Volatile silicones such as cyclomethicones can also be used. Silicone oils are also considered therapeutically active oil, due to their barrier retaining and protective properties.

In one or more embodiments, the hydrophobic carrier includes at least 2% by weight silicone oil or at least 5% by weight.

The solvent may be a mixture of two or more of the above hydrophobic solvents in any proportion.

A further class of solvents includes "emollients" that have a softening or soothing effect, especially when applied to body areas, such as the skin and mucosal surfaces. Emollients are not necessarily hydrophobic. Examples of suitable emollients include hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, sucrose esters of fatty acids, octyl hydroxystearate and mixtures thereof.

An additional class of emollients, suitable according to the present invention consists of polypropylene glycol (PPG) alkyl ethers, such as PPG stearyl ethers and PPG Butyl Ether, which are polypropylene ethers of stearyl ether that function as skin-conditioning agent in pharmaceutical and cosmetic formulations. PPG alkyl ethers can be incorporated in the foamable composition in a concentration between about 1% and about 20%. The sensory properties of foams containing PPG alkyl ethers are favorable, as revealed by consumer panel tests. Surprisingly, it has been discovered that foams comprising PPG alkyl ethers are non-flammable, as shown in a test according to European Standard prEN 14851, titled "Aerosol containers—Aerosol foam flammability test", while foams containing other oils are inflammable.

According to one or more embodiments, the hydrophobic organic carrier includes a mixture of a hydrophobic solvent and an emollient. According to one or more embodiments, the foamable composition is a mixture of mineral oil and an emollient in a ratio between 2:8 and 8:2 on a weight basis.

Polar Solvents

A "polar solvent" is an organic solvent, typically soluble in both water and oil. Examples of polar solvents include polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, sulfoxides, such as dimethylsulfoxide (DMSO), dimethylformanide, methyl dodecyl sulfoxide, dimethylacetamide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one or more embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

According to one or more embodiments, a moisturizing complex is refers to mixtures of chemical agents specially designed to make the external layers of the skin (epidermis) softer and more pliable, by increasing its hydration (water content). Naturally occurring skin lipids and sterols as well as artificial or natural oils, humectants, emollients, lubricants, etc. may be used as part of the moisturizing complex. Besides imparting or restoring normal levels of hydration to the skin, the moisturizing complex can have several additional intended and unintended effects on their users, including building a barrier against the loss of water through the epidermis (skin), repairing scaly, damaged or dry skin resulting from external environmental aggressions or internal changes (such as in acne or naturally dry skin), repairing or postponing the aging effects on the skin, etc.

Hydration or Moisturizing Agents

To combat the potential drying effests of the active agents on the skin, the formulations incorporate a moisturizing complex.

A moisturizing complex can be prepared from two or more chemical agents, such as stearate, olive oil, water and glycerin. Non-limiting examples of such chemicals may include:

(a) Humectants, such as glycerin, urea, lactic acid and sorbitol;

(b) Natural moisturizing factors (NMF) include low molecular weight substances such as ammonia, amino acids, glucosamine, creatinine, citrate and ionic solutions such as sodium, potassium, chloride, phosphate, calcium and magnesium;

(c) Emollients, such as lanolin (the earliest complex organic substances used in facial and body moisturizers, which is extracted from wool). Lanolin acts as a barrier (occlusion effect) against loss of water and also as a softener of stratum corneum, by means of lubrication and smoothing. Other emollients are oil-water emulsions of varying composition and may include several esters and oils such as octyl dodecanol, hexyl decanol, oleyl alcohol, decyl oleate, isopropyl stearate, isopropyl palmitate, isopropyl myristate, hexyl laureate, and dioctyl cyclohexane; and (d) Emulsifier, preserving and fragrance agents are also part of commercial preparations.

The hydrophobic solvent selected can surprisingly play a significant co moisturizing or hydration effect. For example mineral oil is seen to contribute to the hydration effect in combination with glycerin or with sodium PCA.

In certain embodiments, the moisturizing complex is a mixture of glycerin and sodium PCA (sodium salt of 2-pyrrolidone-5-carboxylic acid). In certain other embodiments the complex is a mixture of mineral oil glycerin and sodium PCA.

Derived from the saponification of fats, glycerin (also spelled glycerin and usually referred to in the literature as glycerol) is a strong, nonvolatile trihydroxylated humectant that exhibits hygroscopic ability very similar to that associated with natural moisturizing factor (J. Soc. Cosmet. Chem. 1976; 27:65; Acta Derm. Venereol. 1999; 79:418-21). Natural moisturizing factor is found in corneocytes and can absorb large quantities of water, even when humidity levels are low, which allows the stratum corneum (SC) to maintain a sufficient hydration level in dry environments. Numerous ingredients have been used in moisturizing products to mimic the activity of natural moisturizing factor, and glycerol is one of the more successful.

Natural Moisturizing Factors

One of the primary elements in keeping skin healthy is making sure the structure of the epidermis (outer layer of skin) is intact. That structure is defined and created by skin cells that are held together by the intercellular matrix. The intercellular matrix is the "glue" or "mortar" between skin cells that keep them together. It helps prevent individual skin cells from losing water and creates the smooth, non-flaky appearance of healthy, intact skin. The components that do this are often called natural moisturizing factors (NMFs) or ingredients that mimic the structure and function of healthy skin. While the oil and fat components of skin prevent evaporation and provide lubrication to the surface of skin, it is actually the intercellular matrix along with the skin's lipid content that gives skin a good deal of its surface texture and feel.

The intercellular matrix is the skin's first line of defense against water loss. When the lipid and NMF content of skin is reduced, we experience surface roughness, flaking, fine lines, and a tight, uncomfortable feeling. The longer the skin's surface layer (stratum corneum) is impaired, the less effective the skin's intercellular matrix becomes (Sources: *Skin Research and Technology*, August 2000, pages 128-134; and *Dermatologic Therapy*, Volume 17, Supplement 1, 2004, pages 43-48). Moreover, the skin's healing process is impaired. NMFs make up an expansive group of ingredients that include amino acids, ceramides, hyaluronic acid, cholesterol, fatty acids, triglycerides, phospholipids, glycosphingolipids, urea, linoleic acid, glycosaminoglycans, glycerin, mucopolysaccharide, and sodium PCA (sodium salt of 2-pyrrolidone-5-carboxylic acid). Ingredients that mimic the lipid content of skin are apricot oil, canola oil, coconut oil, corn oil, jojoba oil, jojoba wax, lanolin, lecithin, olive oil, safflower oil, sesame oil, shea butter, soybean oil, squalane, and sweet almond oil, which can all be extremely helpful for making dry skin look and feel better.

All of the skin's supporting NMFs and lipids are present in the intercellular structure of the epidermis, both between skin cells and in the lipid content on the surface of skin. When any of these ingredients are used in skin-care products, they appear to help stabilize and maintain this complex intercellular-skin matrix. Although none of these very good NMFs and lipids can permanently affect or change skin, they are great at temporarily keeping depleted skin from feeling dry and uncomfortable. More important, all of these ingredients, and many more, can help support the intercellular area of the skin by keeping it intact. This support helps prevent surface irritation from penetrating deeper into the skin, works to keep bacteria out, and aids the skin's immune/healing system. Selecting moisturizers of any kind with NMFs (whether they are labeled as being antiaging, antiwrinkle, serums, lotions, or sunscreens) allows your skin to do its job of repairing and regenerating itself without the impedances brought on when skin is suffering from dryness and excess irritation (Sources: *Clinical Geriatric Medicine*, February 2002, pages 103-120; *Progressive Lipid Research*, January 2003, pages 1-36; *Journal of the European Academy of Dermatology and Venereology*, November 2002, pages 587-594; *Contact Dermatitis*, June 2002, pages 331-338; *Journal of Investigative Dermatology*, May 1996, pages 1096-1101; *British Journal of Dermatology*, November 1995, pages 679-685; *Skin Pharmacology and Physiology*, September-October 2004, pages 207-213; *Free Radical Research*, April 2002, pages 471-477; and *Journal of Lipid Research*, May 2002, pages 794-804).

According to one or more embodiments, the moisturizing complex comprises a NMF. In certain embodiments, the NMF is used in combination with one or both of glycerin, sodium pCA. In certain other embodiments the NMF is used in combination with mineral oil and or one or more of glycerin and sodium pCA.

Polymeric Agent

According to one or more embodiments, the polymeric agent serves to contibute to the viscosity of the formulation, stabilize the foam composition and to control drug residence in the target organ. Exemplary polymeric agents are classified below in a non-limiting manner. In certain cases, a given polymer can belong to more than one of the classes provided below.

In one or more embodiments, the composition includes at least one gelling agent. A gelling agent controls the residence of a therapeutic composition in the target site of treatment by increasing the viscosity of the composition, thereby limiting the rate of its clearance from the site. Many gelling agents are known in the art to possess mucoadhesive properties. Surprisingly, it has been found that selected and sparing use of such polymeric agents allows the formation of low viscous formulations which nevertheless can hold BPO particles in a suspension that is able to be physically and chemically stable for pharmaceutical use. Moreover the presence of these polymeric agents enables the foam formulation to contribute to controlling the residence of the active agent at the target site.

The gelling agent can be a natural gelling agent, a synthetic gelling agent and an inorganic gelling agent. Exemplary gelling agents that can be used in accordance with one or more embodiments include, for example, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), guar gum, hydroxypropyl guar gum, soluble starch, cationic celluloses, cationic guars, and the like, and synthetic polymeric materials, such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Mixtures of the above compounds are contemplated.

Further exemplary gelling agents include the acrylic acid/ethyl acrylate copolymers and the carboxyvinyl polymers sold, for example, by the B.F. Goodrich Company under the trademark of Carbopol® resins. In a preferred embodiment the agent is a Carbopol. These resins consist essentially of a colloidal water-soluble polyalkenyl polyether crosslinked polymer of acrylic acid crosslinked with from 0.75% to 2% of a crosslinking agent such as polyallyl sucrose or polyallyl pentaerythritol. Examples include Carbopol® 934, Carbopol® 940, Carbopol® 950, Carbopol® 980, Carbopol® 951 and Carbopol® 981. Carbopol® 934 is a water-soluble polymer of acrylic acid crosslinked with about 1% of a polyallyl ether of sucrose having an average of about 5.8 alkyl groups for each sucrose molecule.

In one or more embodiment, the composition includes at least one polymeric agent, which is a water-soluble cellulose ether. Preferably, the water-soluble cellulose ether is selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose and carboxymethylhydroxyethylcellulose. More preferably, the water-soluble cellulose ether is selected from the group consisting of methylcellulose, hydroxypropyl cellulose and hydroxypropyl methylcellulose (Methocel). In one or more embodiments, the composition includes a combination of a water-soluble cellulose ether; and a naturally occurring polymeric materials, selected from the group including xanthan gum, guar gum, carrageenan gum, locust bean gum and tragacanth gum.

Yet, in other embodiments, the gelling agent includes inorganic gelling agents, such as silicone dioxide (fumed silica).

Mucoadhesive/bioadhesion has been defined as the attachment of synthetic or biological macromolecules to a biological tissue. Mucoadhesive agents are a class of polymeric biomaterials that exhibit the basic characteristic of a hydrogel, i.e. swell by absorbing water and interacting by means of adhesion with the mucous that covers epithelia. Compositions may contain a mucoadhesive macromolecule or polymer in an amount sufficient to confer bioadhesive properties. The bioadhesive macromolecule enhances the delivery of biologically active agents on or through the target surface. The mucoadhesive macromolecule may be selected from acidic synthetic polymers, preferably having at least one acidic group per four repeating or monomeric subunit moieties, such as poly(acrylic)- and/or poly(methacrylic) acid (e.g., Carbopol®, Carbomer®), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral synthetic polymers, such as polyvinyl alcohol or their mixtures. An additional group of mucoadhesive polymers includes natural and chemically modified cyclodextrin, especially hydroxypropyl-β-cyclodextrin. Such polymers may be present as free acids, bases, or salts, usually in a final concentration of about 0.01% to about 0.5% by weight.

A suitable bioadhesive macromolecule is the family of acrylic acid polymers and copolymers, (e.g., Carbopol®). These polymers contain the general structure —[CH$_2$—CH(COOH)—]$_n$. Hyaluronic acid and other biologically-derived polymers may be used.

Exemplary bioadhesive or mucoadhesive macromolecules have a molecular weight of at least 50 kDa, or at least 300 kDa, or at least 1,000 kDa. Favored polymeric ionizable macromolecules have not less than 2 mole percent acidic groups (e.g., COOH, SO$_3$H) or basic groups (NH$_2$, NRH, NR$_2$), relative to the number of monomeric units. The acidic or basic groups can constitute at least 5 mole percent, or at least 10 mole percent, or at least 25, at least 50 more percent, or even up to 100 mole percent relative to the number of monomeric units of the macromolecule.

Yet, another group of mucoadhesive agent includes inorganic gelling agents such as silicon dioxide (fumed silica), including but not limited to, AEROSIL 200 (DEGUSSA).

Many mucoadhesive agents are known in the art to also possess gelling properties.

The foam composition may contain a film-forming component. The film-forming component may include at least one water-insoluble alkyl cellulose or hydroxyalkyl cellulose. Exemplary alkyl cellulose or hydroxyalkyl cellulose polymers include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross-linking agent may be used to modify the polymer's characteristics. For example, esters such as dibutyl or diethyl phthalate, amides such as diethyldiphenyl urea, vegetable oils, fatty acids and alcohols such as oleic and myristyl acid may be used in combination with the cellulose derivative.

In one or more embodiments, the composition includes a phase change polymer, which alters the composition behavior from fluid-like prior to administration to solid-like upon contact with the target mucosal surface. Such phase change results from external stimuli, such as changes in temperature or pH and exposure to specific ions (e.g., Ca$^{2+}$). Non-limiting examples of phase change polymers include poly(N-isopropylamide) and Poloxamer 407®.

The polymeric agent is present in an amount in the range of about 0.01% to about 5.0% by weight of the foam composition. In one or more embodiments, it is typically less than about 1 wt % of the foamable composition. In one or more embodiments, it is formulated to achieve a viscosity in the pre foam formulation of less than about 8000 cps. In certain embodiments the foamable formulation with propellant has a viscosity of less than about 8000 cps and a preferred viscosity in the foamable formulation with propellant of less than about 7000 cps and more preferably less than about 3000 cps. In certain embodiments the ratio of viscosity of the foamable formulation with propellant to the ratio of the viscosity of the pre foam formulation without propellant is between about 1:1, about 19:20; about 9:10; about 4:5; about 3:4; about 3:5; about 2:5 to about 1:5 to about 1:10 preferably between about 19:20 to about 2:5.

One of the surprising discoveries was that the interaction of the BPO polymeric agent was not destroyed upon addition of high pressure volatile liquid propellant. Without being bound by any theory one possible explanation for the phenomena is that when the emulsion formulation is very viscous and propellent is added the formulation becomes fluid and the change in state from thick to liquid effects the polymeric hold on the BPO, which can then move more and tends to sediment and cake. In contrast when the viscosity was such that the pre-foam formulation was liquid and of low viscosity then adding the high pressurized propellant had only a small or minimal effect on the fluidity of the composition and since the hydrophobic propellant will presumably disperse in the oil phase of the emulsion it will now have relatively minor effect on the formulation, which remains with a similar fluidity and the motion of the BPO is relatively unchanged. Why some polymers are better than others at holding BPO in a fluid homogenous suspension in an emulsion formulation over a prolonged time is not currently understood other than perhaps the ability to have polymer at levels were it would otherwise form a gel but for the use of buffer or pH adjuster to prevent gel formation. In other words the selection of gelling agents which are reversibly susceptible to buffer or pH adjuster addition is an unexpected advantage herein.

Surface Active Agent

The composition further contains a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants is usually preferable where the vehicle is an emulsion. In an emulsion environment a combination of surfactants can be significant in producing breakable forms of good quality. It has been further discovered that the generally thought considerations for HLB values for selecting a surfactant or surfactant combination are not always binding for emulsions and that good quality foams can be produced with a surfactant or surfactant combination both where the HLB values are in or towards the lipophilic side of the scale and where the HLB values are in or towards the hydrophilic side of the scale. Surfactants also play a role in foam formation where the foamable formulation is a single phase composition.

According to one or more embodiments the composition contains a single surface active agent having an HLB value between about 2 and 9, or more than one surface active agent and the weighted average of their HLB values is between about 2 and about 9. Lower HLB values may in certain embodiments be more applicable to water in oil emulsions.

According to one or more embodiments the composition contains a single surface active agent having an HLB value between about 7 and 14, or more than one surface active agent and the weighted average of their HLB values is between about 7 and about 14. Mid range HLB values may in certain embodiments be more suitable for oil in water emulsions.

According to one or more other embodiments the composition contains a single surface active agent having an HLB value between about 9 and about 19, or more than one surface active agent and the weighted average of their HLB values is between about 9 and about 19. In a waterless or substantially waterless environment a wide range of HLB values may be suitable.

Preferably, the composition contains a non-ionic surfactant. Nonlimiting examples of possible non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, steareths such as steareth 2, brij 21, brij 721, brij 38, brij 52, brij 56 and brij W1, a sucrose ester, a partial ester of sorbitol and its anhydrides, sorbitan monolaurate, sorbitan monolaurate, a monoglyceride, a diglyceride, isoceteth-20 and mono-, di- and tri-esters of sucrose with fatty acids. In certain embodiments, suitable sucrose esters include those having high monoester content, which have higher HLB values.

In certain embodiments with wax as emollient, surfactants are selected which can provide a close packed surfactant layer separating the oil and water phases. To achieve such objectives combinations of at least two surfactants are selected. Preferably, they should be complex emulgators and more preferably they should both be of a similar molecular type. For example, a pair of ethers like steareth 2 and steareth 21, or a pair of esters for example, PEG-40 stearate and polysorbate 80. In Certain circumstances POE esters cannot be used and a combination of sorbitan laurate and sorbitan stearate or a combination of sucrose stearic acid ester mixtures and sodium laurate may be used. All these combinations due to their versatility and strength may also be used satisfactorily and effectively with wax formulations, although the amounts and proportion may be varied according to the formulation and its objectives as will be appreciated by a man of the art.

It has been discovered also that by using a derivatized hydrophilic polymer with hydrophobic alkyl moieties as a polymeric emulsifier such as pemulen it is possible to stabilize the emulsion better about or at the region of phase reversal tension. Other types of derivatized polymers like silicone copolymers, derivatized starch [Aluminum Starch Octenylsuccinate (ASOS)]/[DRY-FLO AF Starch], and derivatized dexrin may also a similar stabilizing effect.

A series of dextrin derivative surfactants prepared by the reaction of the propylene glycol polyglucosides with a hydrophobic oxirane-containing material of the glycidyl ether are highly biodegradable. [Hong-Rong Wang and Keng-Ming Chen, Colloids and Surfaces A: Physicochemical and Engineering Aspects Volume 281, Issues 1-3, 15 Jun. 2006, Pages 190-193].

Non-limiting examples of non-ionic surfactants that have HLB of about 7 to about 12 include steareth 2 (HLB~4.9); glyceryl monostearate/PEG 100 stearate (Av HLB~11.2); stearate Laureth 4 (HLB~9.7) and cetomacrogol ether (e.g., polyethylene glycol 1000 monocetyl ether).

Non-limiting examples of preferred surfactants, which have a HLB of 4-19 are set out in the Table below:

| Surfactant | HLB |
| --- | --- |
| steareth 2 | ~4.9 |
| glyceryl monostearate/PEG 100 stearate | Av ~11.2 |
| Glyceryl Stearate | ~4 |
| Steareth-21 | ~15.5 |
| peg 40 stearate | ~16.9 |
| polysorbate 80 | ~15 |
| sorbitan stearate | ~4.7 |
| laureth 4 | ~9.7 |
| Sorbitan monooleate (span 80) | ~4.3 |
| ceteareth 20 | ~15.7 |
| steareth 20 | ~15.3 |
| ceteth 20 | ~15.7 |
| Macrogol Cetostearyl Ether | ~15.7 |
| ceteth 2 (Lipocol C-2) | ~5.3 |

-continued

| Surfactant | HLB |
|---|---|
| PEG-30 Dipolyhydroxystearate | ~5.5 |
| sucrose distearate (Sisterna SP30) | ~6 |
| polyoxyethylene (100) stearate | ~18.8 |

More exemplary stabilizing surfactants which may be suitable for use in the present invention are found below.

PEG-Fatty Acid Monoester Surfactants

| Chemical name | Product example name | HLB |
|---|---|---|
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants:

| Chemical name | Product example name | HLB |
|---|---|---|
| PEG-4 dilaurate | Mapeg .RTM. 200 DL (PPG), Kessco .RTM.PEG 200 DL (Stepan), LIPOPEG 2-DL (Lipo Chem.) | 7 |
| PEG-4 | distearate Kessco .RTM. 200 DS (Stepan.sub) | 5 |
| PEG-32 dioleate | Kessco .RTM. PEG 1540 DO (Stepan) | 15 |
| PEG-400 dioleate | Cithrol 4DO series (Croda) | >10 |
| PEG-400 disterate | Cithrol 4DS series (Croda) | >10 |
| PEG-20 glyceryl oleate | Tagat .RTM. O (Goldschmidt) | >10 |

Transesterification Products of Oils and Alcohols

| Chemical name | Product example name | HLB |
|---|---|---|
| PEG-30 castor oil | Emalex C-30 (Nihon Emulsion) | 11 |
| PEG-40 hydrogenated castor oil | Cremophor RH 40 (BASF), Croduret (Croda), Emulgin HRE 40 (Henkel) | 13 |

Polyglycerized Fatty Acids, such as:

| Chemical name | Product example name | LB |
|---|---|---|
| Polyglyceryl-6 dioleate | Caprol .RTM. 6G20 (ABITEC); PGO-62 (Calgene), PLUROL OLEIQUE CC 497 (Gattefosse)Hodag | 8.5 |

PEG-Sorbitan Fatty Acid Esters

| Chemical name | Product example name | HLB |
|---|---|---|
| PEG-20 sorbitan monolaurate | Tween-20 (Atlas/ICI), Crillet 1 (Croda), DACOL MLS 20 (Condea) | 17 |
| PEG-20 sorbitan Monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |

| Chemical name | Product example name | HLB |
|---|---|---|
| PEG-20 sorbitan monooleate | Tween-80 (Atlas/ICI), Crillet 4 (Croda) | 15 |

Polyethylene Glycol Alkyl Ethers

| Chemical name | Product example name | HLB |
|---|---|---|
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | laureth-4Brij 30 (Atlas/ICI) | 9.7 |
| PEG-23 lauryl ether | laureth-23Brij 35 (Atlas/ICI) | 17 |
| PEG-10 stearyl ether | Brij 76 (ICI) | 12 |
| PEG-2 cetyl ether | Brij 52 (ICI) | 5.3 |

Sugar Ester Surfactants

| Chemical name | Product example name | HLB |
|---|---|---|
| Sucrose distearate | Sisterna SP50, Surfope 1811 | 11 |

Sorbitan Fatty Acid Ester Surfactants

| Chemical name | Product example name | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a complex emulgator in which the combination of two or more surface active agents can be more effective than a single surfactant and provides a more stable emulsion or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

Specific non limiting examples of surfactant systems are, combinations of polyoxyethylene alkyl ethers, such as Brij 59/Brij10; Brij 52/Brij 10; Steareth 2/Steareth 20; Steareth 2/Steareth 21 (Brij 72/Brij 721); combinations of polyoxyethylene stearates such as Myrj 52/Myrj 59; combinations of sucrose esters, such as Surphope 1816/Surphope 1807; combinations of sorbitan esters, such as Span 20/Span 80; Span 20/Span 60; combinations of sucrose esters and sorbitan esters, such as Surphope 1811 and Span 60; combinations of liquid polysorbate detergents and PEG compounds, such as Tween 80/PEG-40 stearate; methyl glucaso sequistearate; polymeric emulsifiers, such as Permulen (TRI or TR2); liquid crystal systems, such as Arlatone (2121), Stepan (Mild RM1), Nikomulese (41) and Montanov (68) and the like.

In certain embodiments the surfactant is preferably one or more of the following: a combination of steareth-2 and steareth-21 on their own or in combination with glyceryl monostearate (GMS); in certain other embodiments the surfactant is a combination of polysorbate 80 and PEG-40 stearate. In certain other embodiments the surfactant is a combination of glyceryl monostearate/PEG 100 stearate. In certain other embodiments the surfactant is a combination of two or more of stearate 21, PEG 40 stearate, and polysorbate 80. In certain other embodiments the surfactant is a combination of two or more of laureth 4, span80, and polysorbate 80. In certain other embodiments the surfactant is a combination of two or more of GMS and ceteareth. In certain other embodiments the surfactant is a combination of two or more of steareth 21, ceteareth 20, ceteth 2 and laureth 4 In certain other embodiments the surfactant is a combination of ceteareth 20 and polysorbate 40 stearate. In certain other embodiments the surfactant is a combination of span 60 and GMS. In certain other embodiments the surfactant is a combination of two or all of PEG 40 stearate, sorbitan stearate and polysorbate 60

In certain other embodiments the surfactant is one or more of sucrose stearic acid esters, sorbitan laureth, and sorbitan stearate.

Without being bound by any particular theory or mode of operation, it is believed that the use of non-ionic surfactants with significant hydrophobic and hydrophilic components, increase the emulsifier or foam stabilization characteristics of the composition. Similarly, without being bound by any particular theory or mode of operation, using combinations of surfactants with high and low HLB's to provide a relatively close packed surfactant layer may strengthen the emulsion.

In one or more embodiments the stability of the composition can be improved when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is preferably between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is preferably between about 5 and about 18.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect.

In one or more embodiments the surfactant is a surfactant or surfactant combination is capable of or which tends to form liquid crystals. Surfactants which tend to form liquid crystals may improve the quality of foams. Non limiting examples of surfactants with postulated tendency to form interfacial liquid crystals are: phospholipids, alkyl glucosides, sucrose esters, sorbitan esters.

In one or more embodiments the at least one surface active agent is liquid.

In one or more embodiments the liquid surfactant is a polysorbate, preferably polysorbate 80 or 60.

In one or more embodiments the at least one surface active agent is solid, semi solid or waxy.

It should be noted that HLB values may not be so applicable to non ionic surfactants, for example, with liquid crystals or with silicones. Also HLB values may be of lesser significance in a waterless or substantially non-aqueous environment.

In one or more embodiments the surfactant can be, a surfactant system comprising of a surfactant and a co surfactant, a waxy emulsifier, a liquid crystal emulsifier, an emulsifier which is solid or semi solid at room temperature and pressure, or combinations of two or more agents in an appropriate proportion as will be appreciated a person skilled in the art. Where a solid or semi solid emulsifier combination is used it can also comprise a solid or semi solid emulsifier and a liquid emulsifier.

In one or more embodiments, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. Non-ionic surfactants alone can provide formulations and foams of good or excellent quality in the carriers and compositions provided herein.

Thus, in a preferred embodiment, the surface active agent, the composition contains a non-ionic surfactant. In another preferred embodiment the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1

In one or more embodiments, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1; for example, about 1:1, about 4:1, about 8:1, about 12:1, about 16:1 and about 20:1 or at a ratio of 4:1 to 10:1, for example, about 4:1, about 6:1, about 8:1 and about 10:1.

In selecting a suitable surfactant or combination thereof it should be borne in mind that the upper amount of surfactant that may be used may be limited by the shakability of the composition. If the surfactant is non liquid, it can make the formulation to viscous or solid. This can be particularly significant if the formulation has high molecular weight, e.g., a high molecular weight PEG or polymeric agents or petroleum or if the surfactants are large. Solvents and polymeric agents which have high molecular weight and are very viscous or solid or waxy (e.g., Peg 1500, 2000, etc. or petrolatum) can exacerbate the effect of a waxy or solid surfactant on shakability or flowability In general terms, as the amount of non-liquid surfactant is increased the shakability of the formulation reduces until a limitation point is reached where the formulation becomes non shakable and unsuitable. Thus in one embodiment, an effective amount of surfactant may be used provided the formulation remains shakable. In other certain exceptional embodiments the upper limit may be determined by flowability such as in circumstances where the composition is marginally or apparently non-shakable. The formulation is sufficiently flowable to be able to flow through an actuator valve and be released and still expand to form a good quality foam.

In certain embodiments the amount of surfactant or combination of surfactants is between about 0.05% to about 20%; between about 0.05% to about 15%. or between about 0.05% to about 10%. In a preferred embodiment the concentration of surface active agent is between about 0.2% and about 8%. In a more preferred embodiment the concentration of surface active agent is between about 1% and about 6%.

In one or more embodiments the surfactant comprises a polymeric surfactant.

In some embodiments, it is desirable that the surface active agent does not contain a polyoxyethylene (POE) moiety, such as polysorbate surfactants, POE fatty acid esters, and POE alkyl ethers, because the active agent is incompatible with such surface active agents. For example, the active agent pimecrolimus is not stable the presence of POE moieties, yet benefits greatly from the use of dicarboxylic esters as penetration enhancers. In such cases, alternative surface active agents are employed. In an exemplary manner, POE—free surfactants include non-ethoxylated sorbitan esters, such as sorbitan monopalmitate, sorbitan monostearate, sorbitan tristearate, sorbitan monooleate, sorbitan trioleate, sorbitan monolaurate and sorbitan sesquioleate; glycerol fatty acid esters, such as glycerol monostearate and glycerol monooleate; mono-, di- and tri-esters of sucrose with fatty acids (sucrose esters), sucrose stearate, sucrose distearate sucrose palmitate and sucrose laurate; and alkyl polyglycosides, such as lauryl diglucoside.

If the composition as formulated is a substantially non shakable composition it is nevertheless possible as an exception in the scope for the formulation to be flowable to a sufficient degree to be able to flow through an actuator valve and be released and still expand to form a good quality foam. This surprising and unusual exception may be due one or more of a number of factors such as the high viscosity, the softness, the lack of crystals, the pseudoplastic or semi pseudo plastic nature of the composition and the dissolution of the propellant into the composition.

In one or more embodiments, the surface-active agent includes mono-, di- and tri-esters of sucrose with fatty acids (sucrose esters), prepared from sucrose and esters of fatty acids or by extraction from sucro-glycerides. Suitable sucrose esters include those having high monoester content, which have higher phase inversion and tension.

Phase inversion is a factor in the preparation and stabilization of emulsions and can be both an aid and a detriment. Phase inversion involves the change of emulsion type from o/w to w/o or vice versa. Prior to phase inversion occurring there is a tension in the emulsion which if destabilized or driven will lead to phase inversion and if controlled or ameliorated or dissipated will result in a more stable emulsion. The occurrence of phase inversion during preparation can be a sign of instability. If controlled, it can result in a finer product but if due to other factors after the emulsion was prepared it can cause problems. Inversion can occur by for example adding calcium chloride to an o/w emulsion stabilized with sodium stearate to form calcium stearate. Inversion can also occur as the product of changes to the phase-volume ratio. For example if a small amount of water is added to surfactant mixed with oil and agitated a w/o emulsion is formed. As the amount of water added is gradually increased a point will be reached where the water and emulsifier envelop the oil as small droplets to form an o/w emulsion. The amount of each ingredient including the surfactants will have their part to play in the phenomenon.

Substantially Alcohol-Free

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butaneol, iso-butaneol, t-butaneol and pentanol, are considered less desirable solvents or polar solvents due to their skin-irritating effect. Thus, the composition is substantially alcohol-free and includes less than about 5% final concentration of lower alcohols, preferably less than about 2%, more preferably less than about 1%.

Substantially Non Aqueous

In certain cases, the active agent degrades in the presence of water, and therefore, in such cases the present of water in the composition is not desirable. Thus, in certain preferred embodiments, the composition is substantially non-aqueous. The term "substantially non-aqueous" or "substantially waterless" is intended to indicate that the composition has a water content below about 25%.

Shakability

'Shakability' means that the composition contains some or sufficient flow to allow the composition to be mixed or remixed on shaking. That is, it has fluid or semi fluid properties. In some very limited cases possibly aided by the presence of silicone it may exceptionally be possible to have a foamable composition which is flowable but not apparently shakable.

Breakability

A breakable foam is one that is thermally stable, yet breaks under sheer force.

The breakable foam herein is not "quick breaking" and is not "thermolabile", i.e., it does not collapse quickly upon expulsion and it does not readily collapse or melt upon exposure to body temperature environment. The breakable foam further does not display a long delayed expansion over minutes. Stability over a short time frame of minutes has advantages over foam which collapses quickly upon release. Similarly sheer-force breakability of the foam is clearly advantageous over thermally induced breakability. Both these factors allow for comfortable application and well directed administration to the target area. Breakable foam can break readily upon the application of shear force such as gentle rubbing to spread easily over a target surface. The sheer-force breakable foams herein are of low density, which further assists spreadability and contributes to a light pleasant feel.

Foam Adjuvant

Preferably, a therapeutically effective foam adjuvant is included in the foamable compositions herein to increase the foaming capacity of surfactants and/or to stabilize the foam.

In one or more embodiments, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

In one or more embodiments, a combination of a fatty acid and a fatty ester is employed.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

An important property of the fatty alcohols and fatty acids used in context of the compositions herein is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and anti-inflammatory properties (see, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess anti-infective characteristics.

Thus, in preferred embodiments, a combined and enhanced therapeutic effect is attained by including BPO, an antibiotic agent and a therapeutically effective foam adjuvant in the same composition, thus providing a simultaneous anti-inflammatory and antiinfective effect from both components. Furthermore, in a further preferred embodiment, the composition concurrently comprises an antibiotic agent, a therapeutically effective foam adjuvant and a therapeutically active oil, as detailed above. Such combination provides an even more enhanced therapeutic benefit. Thus, the foamable carrier, containing the foam adjuvant provides an extra therapeutic benefit in comparison with currently used vehicles, which are inert and non-active.

The foam adjuvant according to one or more preferred embodiments includes a mixture of fatty alcohols, fatty acids and hydroxy fatty acids and derivatives thereof in any proportion, providing that the total amount is 0.1% to 5% (w/w) of the carrier mass. More preferably, the total amount is 0.4%-2.5% (w/w) of the carrier mass.

Optionally, the composition further contains a penetration enhancer. Non limiting examples of penetration enhancers include propylene glycol, butylene glycols, glycerol, pentaerythritol, sorbitol, mannitol, oligosaccharides, dimethyl isosorbide, monooleate of ethoxylated glycerides having about 8 to 10 ethylene oxide units, polyethylene glycol 200-600, transcutol, glycofurol and cyclodextrins.

The therapeutic foam may further optionally include a variety of formulation excipients, which are added in order to fine-tune the consistency of the formulation, protect the formulation components from degradation and oxidation and modify their consistency. Such excipients may be selected, for example, from stabilizing agents, antioxidants, humectants, preservatives, colorant and odorant agents and other formulation components, used in the art of formulation.

Propellants

Aerosol propellants are used to generate and administer the foamable composition as a foam. Suitable propellants include volatile hydrocarbons such as butane, propane, isobutane and fluorocarbon gases, or mixtures thereof.

In an embodiment the propellant is AP 70 which is a mixture of propane, isobutene and butane. In another embodiment the propellant is AP 46 which is a similar mixture of propane, isobutene and butane but having a lower pressure. AP 70 offers about 50% higher pressure than AP 46.

The propellant makes up about 3-25 wt % of the foamable composition. In some circumstances the propellant may be up to 35%. The propellants are used to generate and administer the foamable composition as a foam. The total composition including propellant, foamable compositions and optional ingredients can be referred to as the foamable composition.

Alcohol and organic solvents render foams inflammable. It has been surprisingly discovered that fluorohydrocarbon propellants, other than chloro-fluoro carbons (CMOs), which are non-ozone-depleting propellants, are particularly useful in the production of a non-flammable foamable composition. A test according to European Standard prEN 14851, titled "Aerosol containers—Aerosol foam flammability test" revealed that compositions containing an organic carrier that contains a hydrophobic organic carrier and/or a polar solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect include propellants made by DuPont under the registered trademark Dymel, such as 1,1,1,2 tetrafluorethane (Dymel 134), and 1,1,1,2,3, 3,3 heptafluoropropane (Dymel 227). HFCs possess Ozone Depletion Potential of 0.00 and thus, they are allowed for use as propellant in aerosol products.

Notably, the stability of foamable emulsions including HFC as the propellant can be improved in comparison with the same composition made with a hydrocarbon propellant.

In one or more embodiments foamable compositions comprise a combination of a HFC and a hydrocarbon propellant such as n-butane or mixtures of hydrocarbom propellants such as propane, isobutane and butane.

Aging

In order to project the potential shelf life and stability of the compositions and their ingredients particularly active or benefit agents the compositions can subjected to a number of tests, including centrifugation to look for resistance to creaming, phase separation; one or more freeze thaw cycles, standing at room and higher temperatures as an indicator of resistance to aging.

Composition and Foam Physical Characteristics

A pharmaceutical or cosmetic composition manufactured using the foam carrier according to one or more embodiments is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foam composition creates a stable formulation having an acceptable shelf-life of at least six months, preferably at least one year, or more preferably at least two years at ambient temperature. A feature of a product for cosmetic or medical use is long term stability. Propellants, which are usually a mixture of low molecular weight hydrocarbons, tend to impair the stability of emulsions and can cause accelerated breakdown of the active ingredient. It has been observed, however, that foam compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administratable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

A further aspect of the foam is breakability. The breakable foam is thermally stable, yet breaks easily under sheer force. Sheer-force breakability of the foam is clearly advantageous over thermally induced breakability. Thermally sensitive foams immediately collapse upon exposure to skin temperature and begin to be absorbed, and therefore, cannot be applied on the hand and afterwards delivered to the afflicted area a minute or so later since the foam will have practically disappeared.

Another property of the foam is density (specific gravity), as measured upon release from the aerosol can. Typically, foams have low specific gravity of (1) less than 0.12 g/mL; or (2) the range between 0.02 and 0.12; or (3) the range between 0.04 and 0.10; or (4) the range between 0.06 and 0.10.

A further factor is Bubble size. Typically, quality foams have a low bubble size with the average bubble size being below about 300 microns, preferably being below about 200 microns more preferably being below about 120 microns.

Methods

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Canisters Filling and Crimping

Each aerosol canister is filled with the pre-foam formulation ("PFF") and crimped with valve using vacuum crimping machine. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing

Propellant Filling

Pressurizing is carried out using a hydrocarbon gas or gas mixture. Canisters are filled and then warmed for 30 sec in a warm bath at 50° C. and well shaken immediately thereafter.

Closure Integrity Test.

Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.

Tests

By way of non limiting example the objectives of hardness, collapse time, viscosity, bubble size and FTC stability tests are briefly set out below as would be appreciated by a person of the art.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can effect the degree of dermal penetration, efficacy, spreadability and acceptability to the user. The results can also be looked at as an indicator of softness. Note: the foam sample is dispensed into an aluminum sample holder and filled to the top of the holder.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 min.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude. Unless otherwise stated viscosity of the pre-foam formulation (PFF) is provided. It is not practical to try and measure the viscosity of the foamable formulation with regular propellants since they have to be stored in sealed pressurized canisters or bottles. In order to simulate the viscosity in the foamable formulations with propellant an equivalent weight of pentane (a low volatile hydrocarbon) is added to and mixed with the pre-foam formulation and left overnight. The viscosity is then measured as above.

FTC (Freeze Thaw Cycles)

To check the foam appearance under extreme conditions of repeated cycles of cooling, heating, (first cycle) cooling, heating (second cycle) etc., commencing with −10° C. (24 hours) followed by +40° C. (24 hours) measuring the appearance and again repeating the cycle for up to four times.

Density

In this procedure, the foam product is dispensed into vessels (including dishes or tubes) of a known volume and weight. Replicate measurements of the mass of foam filling the vessels are made and the density is calculated. The canister and contents are allowed to reach room temperature. Shake the canister to mix the contents and dispense and discard 5-10 mL. Then dispense foam into a preweighed tube, filling it until excess is extruded. Immediately remove (level off) excess foam at both ends and weigh the filled tube on the weighing balance.

Creaming by Centrifugation

Principle of Test

The centrifugation used in this procedure serves as a stress condition simulating the aging of the liquid dispersion under investigation. Under these conditions, the centrifugal force applied facilitates the coalescence of dispersed globules or sedimentation of dispersed solids, resulting in loss of the desired properties of the formulated dispersion.

Procedure

Following preparation of the experimental formulation/s, allow to stand at room temperature for ≥24 h. Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.

Transfer each mixture to 1.5 mL microtubes. Tap each microtube on the table surface to remove entrapped air bubbles.

Place visually balanced microtubes in the centrifuge rotor and operate the centrifuge at one or more of 10,000 rpm for 10 min, 3,000 rpm for 10 min or at 1,000 rpm for 10 min.

Visual Stability Tests

Spillability

An objective in designing formulations it to formulate so the composition does not lose fluidity, and stays spillable after the incorporation of active agent. Spillability means free moving or rotating of formulation inside the glass bottle upon inversion.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels.

Microscope Size:

The light microscope enables observing and measuring particles from few millimeters down to one micron. Light microscope is limited by the visible light wavelength and therefore is useful to measuring size of particles above 800 nanometers and practically from 1 micron (1,000 nanometers).

Shakability

Shakability represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non shakable. This property may be of particular importance in cases where shaking is required for affecting proper dispersion of the contents.

Shakability Scoring:

| Shakability | |
|---|---|
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

BPO Analytical Method (Used in Section C)

UPLC Determination of Benzoyl Peroxide and Degradation Products in Pressurized Formulation and Pre Foam Formulation An ultra performance liquid chromatography (UPLC) method was used for determining the concentration of the active ingredient BPO and the main degradation product, benzoic acid, and the presence of other degradation products in benzoyl peroxide pre-foam formulations (PFF) and pressurized formulations (PF).

About 270 mg of foam or pre-foam formulation is dissolved in acetonitrile (ACN), sonicated in cold water, mixed and filtered. The filtrate is analyzed by UPLC using a C-18 column; elution is performed with a mobile phase containing water:ACN:Methanol:Acetic acid, 45:45:10:0.1 (v/v/v/v). The peak area is determined.

The content of benzoyl peroxide, benzoic acid and other impurities in the tested sample is calculated from the ratio between the respective peak area of the samples and the average peak area of an ethyl benzoate (EB) standard (0.32 mg/mL) with respect to a response factor (based on the absorbance ratio between EB and BPO). Ethyl Benzoate was found to be a more reliable standard for BPO since discrepancies are observed in the potency of BPO standards on prolong testing probably due to inter alia the variability of moisture in the BPO standard.

Fields of Pharmaceutical Applications

According to one aspect, a method of treating acne is provided, the method comprising administering topically to a subject having acne a foamed composition as described herein. According to another aspect a method of treating other disorders responsive to BPO is provided. According to further aspects a method of treating acne and or other disorders responsive to BPO and antibiotics is provided. According to still further aspects a method of treating acne and or other disorders responsive to BPO and other drugs is provided.

According to another aspect, there is provided a method of enhancing the stability of a foamable composition comprising benzoyl peroxide for treating acne, the method comprising adding a moisturizing complex to the foamable composition. In certain embodiments of this aspect, the moisturizing complex comprises about 5% to about 15% by weight of the total composition not including any oils, which may contribute to improved hydration. In certain other embodiments of this aspect, the moisturizing complex comprises glycerin and sodium PCA. In further aspects the moisturizing complex comprises mineral oil together with one or both of glycerin and sodium PCA. Applicants have surprisingly found that the stability of foamable compositions containing benzoyl peroxide can be enhanced by adding glycerin/pCA to the compositions. Without being bound by any theory the presence of mineral oil or other occlusive oils may also help to prevent water loss and encourage rehydration.

According to a further aspect, there is provided a method of reducing the dryness and/or irritation associated with the use of a composition containing benzoyl peroxide in treating acne, the method comprising adding a moisturizing complex to the composition. In certain embodiments of this aspect, the moisturizing complex comprises about 5% to about 15% by weight of the total composition not including any oils, which may contribute to improved hydration. In certain other embodiments of this aspect, the moisturizing complex comprises glycerin and sodium PCA. In further aspects the moisturizing complex comprises mineral oil together with one or both of glycerin and sodium PCA.

The foamable composition herein is suitable for administration to an inflicted area, in need of treatment, including, but not limited to the skin, a body surface, a body cavity, a mucosal surface, the nose, the mouth, the eye, the ear canal, the respiratory system, the vagina and the rectum (severally and interchangeably termed herein "target site").

Not only are the foamable carrier formulations described herein suitable for delivering BPO on its own or in combination with a one or more compatible active agents that do not help or cause break down of BPO but active agents may be used in and delivered by the said foamable carrier formulations without BPO. In other words whilst the specification describes carriers suitable for BPO, these novel carriers having been discovered and developed can also be used to carry other API's and cosmetic agents described herein. In a particular aspect such foamable carriers can be used to provide homogenous suspensions of insoluble active agents. Non-limiting examples of other solid active agents include Imiquimod (for example, at about 1-5%) and similar compounds; Acyclovir (for example, at about 5%) and similar compounds such as Cyclovir, Acivir, and Zovir; corticosteroids (for example, at about 0.5% or more); encapsulated drugs, wherein the encapsulation or entrapping agent is insoluble, such as Microsponge, silica and other such species; particles, such as polymer microspheres (for example, polyheal); zinc oxide, titanium oxide, silicone oxide (silica) and other insoluble inorganic therapeutic agents Antibiotic agents are initially thought to affect disorders that involve blood circulation abnormalities, yet, in many case, circulation lays a secondary, yet influential role, which must be taken into account in order to optimize treatment. For example, cutaneous malignant tumors are characterized by poor blood circulation, which make them less responsive to drug treatment, and therefore usage of an antibiotic agent would be beneficial to the cancer therapy.

Thus, by including an appropriate antibiotic agent and optionally, additional active agents in the composition, the kit and the composition herein are useful in treating an animal or a patient having one of a variety of dermatological disorders (also termed "dermatoses") and/or having any secondary condition resulting from infections, which disorders and/or conditions are classified in a non-limiting exemplary manner according to the following groups:

Any disorders that involve a microbiological infection, or disorders that respond to treatment with an antibiotic agent, An infection, selected from the group of a bacterial infection, a fungal infection, a yeast infection, a viral infection and a parasitic infection.

Any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Dermatitis including contact dermatitis, atopic dermatitis, seborrheic dermatitis, nummular dermatitis, chronic dermatitis of the hands and feet, generalized exfoliative dermatitis, stasis dermatitis; lichen simplex chronicus; diaper rash;

Bacterial infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, erythrasma;

Fungal Infections including dermatophyte infections, yeast Infections; parasitic Infections including scabies, pediculosis, creeping eruption;

Viral Infections, including, but not limited to herpes genitalis and herpes labialis;

Disorders of hair follicles and sebaceous glands including acne, rosacea, perioral dermatitis, hypertrichosis (hirsutism), alopecia, including male pattern baldness, alopecia greata, alopecia universalis and alopecia totalis; pseudofolliculitis barbae, keratinous cyst;

Scaling papular diseases including psoriasis, pityriasis rosea, lichen planus, pityriasis rubra pilaris;

Benign tumors including moles, dysplastic nevi, skin tags, lipomas, angiomas, pyogenic granuloma, seborrheic keratoses, dermatofibroma, keratoacanthoma, keloid;

Malignant tumors including basal cell carcinoma, squamous cell carcinoma, malignant melanoma, Paget's disease of the nipples, Kaposi's sarcoma;

Reactions to sunlight including sunburn, chronic effects of sunlight, photosensitivity;

Bullous diseases including pemphigus, bullous pemphigoid, dermatitis herpetiformis, linear immunoglobulin A disease;

Pigmentation disorders including hypopigmentation such as vitiligo, albinism and postinflammatory hypopigmentation and hyperpigmentation such as melasma (chloasma), drug-induced hyperpigmentation, postinflammatory hyperpigmentation;

Disorders of cornification including ichthyosis, keratosis pilaris, calluses and corns, actinic keratosis;

Pressure sores;

Disorders of sweating; and

Inflammatory reactions including drug eruptions, toxic epidermal necrolysis; erythema multiforme, erythema nodosum, granuloma annulare.

According to one or more embodiments, the compositions are also useful in the therapy of non-dermatological disorders by providing transdermal delivery of an active antibiotic agent that is effective against non-dermatological disorders.

The same advantage is expected when the composition is topically applied to a body cavity or mucosal surface (e.g., the mucosa of the nose and mouth, the eye, the ear canal, vagina or rectum) to treat conditions such aschlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment, the composition is useful for the treatment of one or more of skin irritations, wound, ulcer and burn. This use is particularly important since the composition preads easily on the afflicted area, without the need of extensive rubbing. Similarly it can be used for prophylactic purposes and as a disinfectant.

In light of the expansion of the foam upon administration, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising an antibiotic agent and optionally, appropriate protective agents, the foam is suitable for the treatment or prevention of post surgical adhesions.

Other foamable compositions are described in: U.S. Publication No. 05-0232869, published on Oct. 20, 2005, entitled NONSTEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No. 06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. Publication No. 2007-0292355 published on Dec. 20, 2007 and entitled ANTI-INFECTION AUGMENTATION OF FOAMABLE COMPOSITIONS AND KIT AND USES THEREOF; U.S. Publication No. 2008-0069779 and entitled DICARBOXYLIC ACID FOAMABLE VEHICLE AND PHARMACEUTICAL COMPOSITIONS THEREOF; U.S. Publication 20080206159, published on Aug. 28, 2008 and entitled COMPOSITIONS WITH MODULATING AGENTS; U.S. patent application Ser. No. 11/767,442, filed on Jun. 22, 2007, entitled FOAMABLE COMPOSITIONS AND KITS COMPRISING ONE OR MORE OF A CHANNEL AGENT, A CHOLINERGIC AGENT, A NITRIC OXIDE DONOR, AND RELATED AGENTS AND THEIR USES; U.S. Publication 2008-0069779, published on Mar. 20, 2008 and entitled FOAMABLE VEHICLE AND VITAMIN AND FLAVONOID PHARMACEUTICAL COMPOSITIONS THEREOF, all of which are incorporated herein by reference in their entireties with reference to any of the active ingredients; penetration enhancers; humectants; moisturizers; listed therein can be applied herein and are incorporated by reference.

The invention is described with reference to the following examples. This invention is not limited to these examples and experiments. Many variations will suggest themselves and are within the full-intended scope of the appended claims.

| Table of Ingredients Used | | | | |
|---|---|---|---|---|
| Ingredients | Brand name | Category | HLB | RHLB |
| Polysorbate 60 | Tween 60 | Surfactant | 14.9 | |
| Polysorbate 20 | Tween 20 | Surfactant | 16.7 | |
| Polysorbate 80 | Tween 80 | Surfactant | 15 | |
| Ceteth 20 | Lipocol C-20 | Surfactant | 15.4 | |

-continued

| Ingredients | Brand name | Category | HLB | RHLB |
|---|---|---|---|---|
| Steareth 2 | Brij 72 | Surfactant | 4.9 | |
| sreareth 21 | Brij 721 | Surfactant | 15.5 | |
| PEG 40-stearate | Myrj 52 | Surfactant | 16.9 | |
| PEG 100-stearate | Myrj 59 | Surfactant | 18.8 | |
| sorbitan laurate | Span 20 | Surfactant | 8.6 | |
| sorbitan stearate | Span 60 | Surfactant | 4.7 | |
| sorbitan palmitate | Span 40 | Surfactant | 6.7 | |
| Glyceryl monostearate | Cutina GMS | Surfactant | 3.8 | |
| Stearyl alcohol | Speziol C-18 | Foam adjuvant | | 15.5 |
| Cetostearyl alcohol | Speziol C 16-18 | Foam adjuvant | | 15.5 |
| Cocoglycerides | Novata A | Thickener | | ~8 |
| Sodium Carboxymethyl cellulose (30000) | Cekol 30000 | Polymer | | |
| Hydroxypropyl methylcellulose | Methocel K100M | Polymer | | |
| Xanthan gum | Xantural 11K | Polymer | | |
| hydroxypropyl cellulose | Klucel EF | Polymer | | |
| Aluminum starch octenylsuccinate | DryFlo plus | Polymer | | |
| Carbomer 941 | Carbopol 981 | Polymer | | |
| Carbomer 940 | Carbopol 980 | Polymer | | |
| Carbomer 934P | Carbopol 974P | Polymer | | |
| Crospovidone CL-M | Poly (Vinylpolypyrrolidone) | Polymer | | |
| Cyclopentasiloxane | Cyclomethicone | Emollient | | 7.75 |
| Jojoba Oil | Jojoba Oil | Emollient | | 6.5 |
| light Mineral oil | pioneer 2076p | Emollient | | 10.5 |
| Caprylic/Capryc triglycerides | MCT oil | Emollient | | 5 |
| Citric acid | Citric acid | buffer agent | | |
| Sodium Citrate | Sodium Citrate | buffer agent | | |
| Sodium hydroxide | Sodium hydroxide | pH agent | | |
| Triethanolamine | Triethanolamine | pH agent | | |
| Purified water | Purified water | Solvent | | |
| Propylene glycol | Propylene glycol | Humectant | | |
| Glycerin | Glycerin | Humectant | | |
| sodium salt of pyrrolidone carbonic acid | Sodium PCA | Humectant | | |
| Benzoyl Peroxide | Benzoyl Peroxide | API | | |
| propane + butane + + isobutene (AP-70) | | Propellant | | |

As BPO can be an irritant the ingredients used in the formulations were identified as being non irritants in the concentrations used.

EXAMPLES

The Examples below describe the experimental development of the BPO formulations provided herein.

Section A—Non Oil Aqueous Formulations with BPO

The examples below have between about in excess of 70% to about in excess of 90% water and no oil save some examples contain either an emollient foam adjuvant or an emulsifying mix.

Example 1

Over about 90% Water and 1% CMC as Polymer

| chemical name | 009 | 010 | 011 | 013 | 017 |
|---|---|---|---|---|---|
| Polysorbate 60 | 1.00 | | 1.00 | | |
| Stearyl alcohol | | | 1.00 | 1.00 | 2.00 |
| Sodium Carboxymethyl cellulose (30000) | 1.00 | 1.00 | 1.00 | 1.00 | 1.00 |
| Purified water | 92.0 | 93.0 | 91.0 | 92.0 | 91.0 |
| Benzoyl Peroxide | 6.0 | 6.0 | 6.0 | 6.0 | 6.0 |
| Control: | 100.00 | 100.00 | 100.00 | 100.00 | 100.00 |
| Propellant (AP-70) | 8.00 | 8.00 | 8.00 | 8.00 | 8.00 |

|  | 009 | 010 | 011 | 013 | 017 |
|---|---|---|---|---|---|
| Results |  |  |  |  |  |
| QUALITY | G-E | P | G-E | FG | FG |
| COLOR | W |  | W | W | W |
| ODOR | NO ODOR |  | NO ODOR | NO ODOR | NO ODOR |
| SHAKABILITY visual inspection (presurized glass bottle) | GOOD non homog.-white, opaque amorphous particals dispensed in liquid, no reversibility |  | GOOD non homog.-white, opaque amorphous particals dispensed in liquid, no reversibility | GOOD | GOOD |
| Collapse time (sec.) | 110/F |  | 90/FG |  |  |

G-E = Good to Excellent;
FG = Fairly Good; and
P = Poor;
No reversibility - = Upon shaking large BPO large particals were still observed during shaking, which immediately sedimented when shaking ended.

Comments: In this case, a surfactant (e.g. Polysorbate 60) is required to obtain good foam. In the presence of BPO, CMC polymer without surfactant resulted in poor foam. Addition of foam adjuvant improved matters and produced fairly good foam. However, doubling the amount of the foam adjuvant did not result in any further significant improvement. CMC polymer with surfactant did result in good quality foam but addition of foam adjuvant did not in this case appear to help. Collapse time is moderate and homogenity requires attention.

Manufacturing Procedure (009)
    Step 1: Preparation of Water Phase (A)
        1.1. Heat water to 60-65° C., add CMC while stirring
        1.2. add Polysorbate 60 while mixing
        1.3. cool to RT
    Step 2: Benzoyl peroxide addition
    Add Benzoyl peroxide. Mix thoroughly
    Step 3: Homogenization
    Homogenize 15 minutes.
    Step 4: Canisters Filling and Crimping
    Fill canister with PFF and crimped with valves
    Step 5: Pressurizing
    Canisters are filled with 8% propellant.

Manufacturing Procedure (010)
Step 1: Preparation of Water Phase (A)
    1.1. Heat water to 60-65° C., add CMC while stirring
    1.2. cool to RT
Step 2: Benzoyl peroxide addition
    Add Benzoyl peroxide. Mix thoroughly
Step 3: Homogenization
    Homogenize 15 minutes
Step 4: Canisters Filling and Crimping
    Fill canister with PFF and crimped with valves
Step 5: Pressurizing
    Canisters are filled with 8% propellant.

Manufacturing Procedure (011)
Step 1: Preparation of Water Phase (A)
    1.1. Heat water to 60-65° C., add CMC stirring.
    1.2. add Polysorbate 60 and Stearyl alcohol
    1.3. cool to RT
Step 2: Benzoyl peroxide addition
    Add Benzoyl peroxide. Mix thoroughly.
Step 3: Homogenization
    Homogenize 15 minutes.
Step 4: Canisters Filling and Crimping
    Fill canister with PFF and crimped with valves
Step 5: Pressurizing
    Canisters are filled with 8% propellant.

Manufacturing Procedure (013)
Step 1: Preparation of Water Phase (A)
    1.1. Heat water to 60-65° C., add CMC while stirring.
    1.2. add Stearyl alcohol
    1.3. cool to RT
Step 2: Benzoyl peroxide addition
    Add Benzoyl peroxide. Mix thoroughly.
Step 3: Homogenization
    Homogenize 15 minutes
Step 4: Canisters Filling and Crimping
    Fill canister with PFF and crimped with valves
Step 5: Pressurizing
    Canisters are filled with 8% propellant.

Manufacturing Procedure (017)
Step 1: Preparation of Water Phase (A)
    1.1. Heat water to 60-65° C., add CMC while stirring
    1.2. add Stearyl alcohol
    1.3. Cool to RT
Step 2: Benzoyl peroxide addition
    Add Benzoyl peroxide. Mix thoroughly.
Step 3: Homogenization
    Homogenize 15 minutes.
Step 4: Canisters Filling and Crimping
    Fill canister with PFF and crimped with valves
Step 5: Pressurizing
    Canisters are filled with 8% propellant.

Example 2

Over about 90% Water and 0.7% Xanthan/Methocel as Polymer

|  | 012 | 015 | 014 | 016 |
|---|---|---|---|---|
| chemical name | | | | |
| Polysorbate 60 | 1.00 | | 1.00 | |
| Stearyl alcohol | | | 1.00 | 1.00 |
| Hydroxypropyl methylcellulose (Methocel K100M) | 0.35 | 0.35 | 0.35 | 0.35 |
| Xanthan gum | 0.35 | 0.35 | 0.35 | 0.35 |
| Purified water | 92.3 | 93.3 | 91.3 | 92.3 |
| Benzoyl Peroxide | 6.0 | 6.0 | 6.0 | 6.0 |
| Control: | 100.00 | 100.00 | 100.00 | 100.00 |
| Propellant (AP-70) | 8.00 | 8.00 | 8.00 | 8.00 |
| Results | | | | |
| QUALITY | G-E | G-E | G-E | F |
| COLOR | W | W | W | |
| ODOR | NO ODOR | NO ODOR | NO ODOR | |
| SHAKABILITY | GOOD | GOOD | GOOD | |
| visual inspection (presurized glass bottle) | non homog.- white, opaque amorphous particals dispensed in liquid, no reversibility | non homog.- white, opaque amorphous particals dispensed in liquid, no reversibility | non homog.- white, opaque amorphous particals dispensed in liquid, no reversibility | non homog.- white, opaque amorphous particals dispensed in liquid, no reversibility |
| Collapse time (sec.) | 100/F | >300/E | 180/FG | |

No reversibility- = Upon shaking large BPO large particals were still observed during shaking, which immediately sedimented when shaking ended Comments: Replacing CMC polymer with xanthan/methocel as polymer results in good to excellent foam even without surfactant that has a collapse time in excess of 5 minutes. Methocel is a gelling polymer that in addition to being a gelling agent can have a stabilizing effect of suspensions and emulsions. Surprisingly the addition of surfactant reduces the collapse time and although the addition of foam adjuvant improves the collapse time the polymeric combination alone surprisingly results in the better formulation. Also surprising is that addition of Foam Adjuvant to the xanthan/methocel polymer formulation without surfactant results in only Fair foam, where as without the adjuvant results in good to excellent foam. This may be due to there being not enough stabilizing power from the polymeric agents to stabilize the fatty acid in the water medium. Homogeneity requires attention.

Manufacturing Procedure (012)

Step 1: Preparation of Water Phase (B)
  1.1. Heat part of water to 90° C., Add Methocel K100M with agitation until thoroughly wetted and evenly dispersed, no clumps are detected. Cool the rest of water. Add the hot water to the cool water while mixing until homogeneous and no particles are observed.
  1.2. Heat (Step 1.1) to 50° C., add Xanthan gum with vigorous mixing. Add Polysorbate 60.
  1.3. cool to RT Step 2: Homogenization
  2.1. Add Benzoyl peroxide and homogenize for 15 minutes while cooling with ice bath.
  2.2. add water if necessary to obtain the correct weight.

Step 3: Canisters Filling and Crimping
  Fill canister with PFF and crimped with valves Step 4: Pressurizing
  Canisters are filled with 8% propellant.

Manufacturing Procedure (014)

Step 1: Preparation of Water Phase (B)
  1.1. Heat part of water to 90° C., Add Methocel K100M with agitation until thoroughly wetted and evenly dispersed, no clumps are detected. Cool the rest of water. Add the hot water to the cool water while mixing until homogeneous and no particles are observed.
  1.2 Heat (Step 1.1) to 50° C., add Xanthan gum with vigorous mixing. Add Polysorbate 60.
  1.3 cool to RT Step 2: Homogenization
  Add Benzoyl peroxide and homogenize for 15 minutes at 8000 RPMs while cooling with ice bath.
  Check the final weight of emulsion and add water if necessary to obtain the correct weight.

Step 3: Canisters Filling and Crimping
  Fill canister with PFF and crimped with valves Step 4: Pressurizing
  Canisters are filled with 8% propellant.

Manufacturing Procedure (015)

Step 1: Preparation of Water Phase (B)
  1.1. Heat part of water to 90° C., Add Methocel K100M with agitation until thoroughly wetted and evenly dispersed, no clumps are detected. Cool the rest of water. Add the hot water to the cool water while mixing until homogeneous and no particles are observed.
  1.2 Heat (Step 1.1) to 50° C., add Xanthan gum with vigorous mixing. Add Polysorbate 60 and Stearyl alcohol.
  1.3 cool to RT Step 2: Homogenization
Add Benzoyl peroxide and homogenize for 15 minutes at 8000 RPMs while cooling with ice bath.
Check the final weight of emulsion and add water if necessary to obtain the correct weight.
Step 3: Canisters Filling and Crimping
  Fill canister with PFF and crimped with valves
Step 4: Pressurizing
  Canisters are filled with 8% propellant.
Manufacturing Procedure (016)
Step 1: Preparation of Water Phase (B)
  1.2. Heat part of water to 90° C., Add Methocel K100M with agitation until thoroughly wetted and evenly dispersed, no clumps are detected. Cool the rest of water. Add the hot water to the cool water while mixing until homogeneous and no particles are observed.
  1.2 Heat (Step 1.1) to 50° C., add Xanthan gum with vigorous mixing. Add Stearyl alcohol.
  1.3 cool to RT
Step 2: Homogenization
Add Benzoyl peroxide and homogenize for 15 minutes at 8000 RPMs while cooling with ice bath.
Check the final weight of emulsion and add water if necessary to obtain the correct weight.
Step 3: Canisters Filling and Crimping
  Fill canister with PFF and crimped with valves
Step 4: Pressurizing
  Canisters are filled with 8% propellant.

Example 3

Over about 80% Water and High Amounts Polymer (about 7% to about % of Klucel or CMS with or without ASOS)

| chemical name | 019 | 020 | 022 |
|---|---|---|---|
| Polysorbate 60 | 2.00 | 2.00 | 2.00 |
| Sodium Carboxymethyl cellulose (30000) | | 7.00 | |
| Klucel EF | 7.00 | | 7.00 |
| ASOS | | | 2.00 |
| Benzoyl Peroxide | 6.0 | 6.0 | 6.0 |
| Purified water | 85.0 | 85.0 | 83.0 |
| Control: | 100.00 | 100.00 | 100.00 |
| Propellant (AP-70) | 8.00 | 8.00 | 8.00 |
| Results | | | |
| Viscosity (PFF) | 307.93 | | 184.96 |
| QUALITY | G-E | BLOCK | G-E |
| COLOR | W | | W |
| ODOR | NO ODOR | | NO ODOR |
| SHAKABILITY | GOOD | | GOOD |
| Density | 0.035 | | 0.035 |
| Collapse time (sec.) | | | >300/FG |
| FTC | | | |
| foam quality | | | E |
| color | | | White |
| odor | | | very faint odor |
| shakability | | | good |

Comments: High levels of CMC resulted in the formulation blocking the valve. However, when Klucel was used at high levels (7%) with and without ASOS (Aluminum Starch Octenylsuccinate) good to excellent foam was obtained.

Manufacturing Procedure (019)
Step 1: Preparation of Water Phase
  a. Add Klucel EF to water at 40 C while vigorously stirring.
  b. Heat to 40-50 C and add polysorbate 60 while stirring.
  c. Cool to RT and Add Benzoyl peroxide. Mix thoroughly
  d. add water if necessary to obtain the correct weight.
Step 2: Canisters Filling and Crimping
  Fill canister with PFF and crimped with valves
Step 3: Pressurizing
  Canisters are filled with 8% propellant.
Manufacturing Procedure (020)
Step 1: Preparation of Water Phase
  a. Add NaCMC to water at 40 C while vigorously stirring.
  b. Heat to 40-50 C and add polysorbate 60 while stirring.
  c. Cool to RT and Add Benzoyl peroxide. Mix thoroughly
  d. add water if necessary to obtain the correct weight.
Step 2: Canisters Filling and Crimping
  Fill canister with PFF and crimped with valves
Step 3: Pressurizing
  Canisters are filled with 8% propellant.
Manufacturing Procedure (022)
Step 1: Preparation of Water Phase
  a. Add Klucel EF and ASOS to water at 40 C while vigorously stirring.
  b. Heat to 40-50 C and add polysorbate 60 while stirring.
  c. Cool to RT and Add Benzoyl peroxide. Mix thoroughly
  d. add water if necessary to obtain the correct weight.
Step 2: Canisters Filling and Crimping
  Fill canister with PFF and crimped with valves
Step 3: Pressurizing
  Canisters are filled with 8% propellant.

Example 4

Over about 80% Water Plus Surfactants without Polymeric Agents

| chemical name | 021 | 032 |
|---|---|---|
| Polysorbate 20 | 3.00 | 3.00 |
| Ceteth 20 | 2.00 | 3.00 |
| sreareth 21 | | 2.00 |
| PEG 100-stearate | 3.00 | 2.00 |
| Purified water | 85.0 | 84.0 |
| Benzoyl Peroxide | 6.0 | 6.0 |
| Control: | 100.00 | 100.00 |
| Propellant (AP-70) | 8.00 | 8.00 |
| Results | | |
| Viscosity (PFF) | | 5 |
| QUALITY | G-E | G-E |
| COLOR | W | W |
| ODOR | NO ODOR | NO ODOR |
| SHAKABILITY | GOOD | GOOD |
| Density | | 0.041 |
| Bubble size (μm) | | 107 |
| Bubble size (above 500 μm) | | 0.0 |
| Collapse time (sec.) | | >300/G |

Comments: The combination surfactant systems used were able to generate good to excellent foams. Combinations or complex emulgators are generally superior in emulsion stability and foam quality. Also, combinations or complex emulgators contribute to collapse time especially when surfactants are solid at troom temp.

Manufacturing Procedure (021, 032)
a. Add all ingredients to water at 50 C while vigorously stirring till complete dissolution.
b. Cool to RT and Add Benzoyl peroxide. Mix thoroughly
c. add water if necessary to obtain the correct weight.
Step 2: Canisters Filling and Crimping
Fill canister with PFF and crimped with valves
Step 3: Pressurizing
Canisters are filled with 8% propellant.

Example 5

Combinations of Liquid or Liquid and Solid Surfactants Plus Stearyl Alcohol as Foam Adjuvant without Polymeric Agent Liquid surfactants do not affect viscosity, whereas solid surfactants increase viscosity by adding bulk to improve the quality of the foam.

a) liquid surfactants only with stearyl alcohol

| chemical name | 023 | 027 |
|---|---|---|
| Polysorbate 60 |  | 3.50 |
| Polysorbate 20 | 3.00 | 2.00 |
| sorbitan laurate (span 20) | 3.00 |  |
| Stearyl alcohol | 2.00 | 3.00 |
| Purified water | 86.0 | 85.5 |
| Benzoyl Peroxide | 6.0 | 6.0 |
| Control: | 100.00 | 100.00 |
| Propellant (AP-70) | 8.00 | 8.00 |
| Results |  |  |
| QUALITY | G-E | G-E |
| COLOR | W | W |
| ODOR | NO ODOR | NO ODOR |
| SHAKABILITY | GOOD | GOOD |
| Density |  |  | b) Liquid and solid surfactants only with stearyl alcohol

| chemical name | 028 | 029 | 030 | 031 | 033 |
|---|---|---|---|---|---|
| Propylene glycol |  |  |  | 3.00 |  |
| Polysorbate 60 | 3.00 |  |  |  |  |
| Polysorbate 20 | 2.00 | 3.60 | 3.60 | 3.60 | 2.50 |
| Ceteth 20 | 1.00 |  |  |  |  |
| sorbitan laurate (span 20) |  | 1.60 | 1.60 | 1.60 | 1.40 |
| PEG 100-stearate | 2.00 | 2.10 | 2.10 | 2.10 | 2.10 |
| Stearyl alcohol | 4.00 | 10.00 | 7.00 | 4.00 | 2.00 |
| Purified water | 82.0 | 76.7 | 79.7 | 79.7 | 86 |
| Benzoyl Peroxide | 6.0 | 6.0 | 6.0 | 6.0 | 6.0 |
| Control: | 100.00 | 100.00 | 100.00 | 100.00 | 100.00 |
| Propellant (AP-70) | 8.00 | 8.00 | 8.00 | 8.00 | 8.00 |
| Results |  |  |  |  |  |
| Viscosity (PFF) |  | 116.98 |  |  |  |
| Quality | G-E | G-E | G-E | G-E | G-E |
| Color | W | W | W | W | W |
| Odor | NO ODOR | NO ODOR | NO ODOR | NO ODOR | NO ODOR |
| Shakability | GOOD | GOOD | GOOD | GOOD | GOOD |
| Density |  | 0.052 |  |  |  |
| Bubble size (μm) |  | 101 |  |  |  |
| Bubble size (above 500 μm) |  | 4.0 |  |  |  |
| Collapse time (sec.) |  | >300/G |  |  |  |

Comments: Various formulations were explored with different surfactants and amounts of stearyl alcohol without polymer. The formulations contained at least one liquid surfactant and resulted in good to excellent quality foam.

Manufacturing Procedure (all Formulations in Example 5a & 5b)
a. Add all ingredients to water at 50-60 C while vigorously stirring to complete dissolution.
b. Cool to RT and Add Benzoyl peroxide. Mix thoroughly
c. add water if necessary to obtain the correct weight.

Step 2: Canisters Filling and Crimping
Fill canister with PFF and crimped with valves Step 3: Pressurizing
Canisters are filled with 8% propellant.

Example 6

Over about 70% Water Plus Cetylstearyl Alcohol an Emollient Foam Adjuvant, and Surfactants with and without 10% Silicone and 0.5% Polymer

| chemical name | 034 | 040 |
|---|---|---|
| cyclomethicone | | 10.00 |
| Polysorbate 60 | | 3.10 |
| Polysorbate 20 | 3.00 | |
| sorbitan laurate (span 20) | 1.50 | |
| sorbitan stearate (span 60) | | 2.90 |
| PEG 100-stearate | 2.00 | |
| Glyceryl stearate | | 1.00 |
| Cetostearyl alcohol | 4.00 | 2.00 |
| Hydroxypropyl methylcellulose (Methocel K100M) | | 0.25 |
| Xanthan gum | | 0.25 |
| Purified water | 83.50 | 74.5 |
| Benzoyl Peroxide | 6.0 | 6.0 |
| Control: | 100.00 | 100.00 |
| Propellant (AP-70) | 8.00 | 8.00 |
| Results | | |
| Viscosity (PFF) | 6142.69 | |
| QUALITY | G-E | G-E |
| COLOR | W | W |
| ODOR | NO ODOR | NO ODOR |
| SHAKABILITY | GOOD | GOOD |
| Density | 0.033 | |
| Bubble size (μm) | 226 | |
| Bubble size (above 500 μm) | 3.8 | |
| Collapse time (sec.) | >300/G | |

Comments: The formulations contained at least an emollient foam adjuvant, and a surfactant and resulted in good to excellent quality foam with and without a silicone. Polymer was added with the silicone to improve stability.

Manufacturing Procedure (034)
a. Add all ingredients to water at 50-60 C while vigorously stirring to complete dissolution.
b. Cool to RT and Add Benzoyl peroxide. Mix thoroughly
c. add water if necessary to obtain the correct weight.

Step 2: Canisters Filling and Crimping
Fill canister with PFF and crimped with valves Step 3: Pressurizing
Canisters are filled with 8% propellant.

Manufacturing Procedure (040)
Step 1: Preparation of Oily Phase (A)
Heat all ingredients to 65 C to complete dissolution.

Step 2: Preparation of Water Phase (B)
Add Methocel K100M to water at 5-20 C while vigorously mixing. Heat to 60 C and Add Xanthan gum while mixing. Add polysorbate 80.

Step 3: Preparation of PFF
Add A to B while mixing. Cool to 40 C. Add Cyclomethicone. Cool to RT
Add Benzoyl peroxide. Mix thoroughly while cooling with ice.
Add water if necessary to obtain the correct weight.

Step 4: Canisters Filling and Crimping
Fill canister with PFF and crimped with valves Step 5: Pressurizing
Canisters are filled with 8% propellant.

Example 7

5% Jojoba a Liquid Wax and High Klucel with about 79% Water

| chemical name | 024 | 025 |
|---|---|---|
| Jojoba Oil | 5.00 | 5.00 |
| Polysorbate 60 | 0.50 | |
| sorbitan stearate (span 60) | 2.50 | |
| sorbitan palmitate (span 40) | | 3.00 |
| Klucel EF | 7.00 | 7.00 |
| Purified water | 79.0 | 79.0 |
| Benzoyl Peroxide | 6.0 | 6.0 |
| Control: | 100.00 | 100.00 |
| Propellant (AP-70) | 8.00 | 8.00 |
| Results | | |
| Viscosity (PFF) | 1152.75 | 1190.75 |
| QUALITY | G-E | G-E |
| COLOR | W | W |
| ODOR | NO ODOR | NO ODOR |
| SHAKABILITY | GOOD | GOOD |
| Density | 0.052 | 0.05 |
| Collapse time (sec.) | >300/G | |
| FTC | | |
| Foam quality | G | G |
| Color | White | White |
| Odor | very faint odor | very faint odor |
| Shakability | good | good |

Comments: Jojoba oil is a liquid wax with sebum like qualities. Good quality foam was produced with high polymer levels and jojoba and different surfactants.

Manufacturing Procedure (024, 025)
Step 1: Preparation of Oil Phase(A)
Mix the Jojoba Oil and Span 60 and Heat up to 60-65 C Step 2: Preparation of Water Phase(B)
Add other ingredients (besides BPO) to water at 60-65 C while vigorously stirring till complete dissolution.

Step 3: Preparation of Emulsion (PFF)
Add the water phase to the oily phase while vigorously stirring at 60-65 C Step 4: BPO Addition.
Cool to RT and Add Benzoyl peroxide. Mix thoroughly add water if necessary to obtain the correct weight.

Step 5: Canisters Filling and Crimping
Fill canister with PFF and crimped with valves Step 6: Pressurizing
Canisters are filled with 8% propellant.

Example 8

5% PG and High Levels of Polymer (Klucel) with about 90% Water

| chemical name | 026 |
|---|---|
| Propylene glycol | 5.00 |
| Polysorbate 20 | 2.00 |
| Klucel EF | 7.00 |
| Purified water | 80.00 |
| Benzoyl Peroxide | 6.00 |
| Control: | 100.00 |
| Propellant (AP-70) | 8.00 |
| Results | |
| Viscosity (PFF) | 209.96 |
| QUALITY | G-E |
| COLOR | W |
| ODOR | NO ODOR |
| SHAKABILITY | GOOD |
| Density | 0.034 |
| Collapse time (sec.) | 150/FG |

Comments: It was possible to produce good to excellent quality foam in the presence of PG (a penetration enhancer) with high levels of polymer albeit with a shorter collapse time.

Manufacturing Procedure (026)

Step 1: Preparation of Water Phase a. Add Klucel EF to water at 40 C while vigorously stirring.

B. Add Propylene glycol and Polysorbate 20 while stirring.

c. Cool to RT and Add Benzoyl peroxide. Mix thoroughly d. add water if necessary to obtain the correct weight.

Step 2: Canisters Filling and Crimping

Fill canister with PFF and crimped with valves

Step 3: Pressurizing

Canisters are filled with 8% propellant.

Example 9

Over about 90% Water and 7% Cocoglycerides an Emollient with Some Emulsifying Properties with and without a Foam Adjuvant

| chemical name | 035 | 037 |
|---|---|---|
| Cocoglycerides | 7.00 | 7.00 |
| Polysorbate 80 | 2.00 | 2.50 |
| sorbitan oleate (span 80) | 5.00 | 4.50 |
| Glyceryl stearate | | 1.00 |
| Sodium Carboxymethyl cellulose (30000) | 0.50 | 0.50 |
| Purified water | 79.50 | 78.50 |
| Benzoyl Peroxide | 6.0 | 6.0 |
| Control: | 100.00 | 100.00 |
| Propellant (AP-70) | 8.00 | 8.00 |
| Results | | |
| Viscosity (PFF) | | 13197.18 |
| QUALITY | FG | G |
| COLOR | | W |
| ODOR | | v. f. od |
| SHAKABILITY | | GOOD |
| Density | | 0.072 |
| Bubble size (µm) | | 270 |
| Bubble size (above 500 µm) | | 3.7 |
| Collapse time (sec.) | | >300/G |

Comments: Cocoglyceride is an emollient with surfactant-like properties (semi-surfactant). Addition of glyceryl stearate to the cocoglycerides formulation with sodium CMC resulted in improving the foam quality to good foam with a collapse time in excess of 5 minutes.

Manufacturing Procedure (035, 037)

Step 1: Preparation of Oily Phase (A)

Heat all ingredients to 65 C to complete dissolution.

Step 2: Preparation of Water Phase (B)

Heat water to 65 C. Add Sodium Carboxymethyl cellulose while vigorously mixing

Step 3: Preparation of PFF

Add A to B while mixing. Cool to RT

Add Benzoyl peroxide. Mix thoroughly while cooling with ice.

Add water if necessary to obtain the correct weight.

Step 4: Canisters Filling and Crimping

Fill canister with PFF and crimped with valves

Step 5: Pressurizing

Canisters are filled with 8% propellant.

Example 10

Over about 70% Water and 10/11% Silicone with Polymer

| chemical name | 038 | 039 | 040 |
|---|---|---|---|
| cyclomethicone | 11.00 | 10.00 | 10.00 |
| Polysorbate 60 | | 2.40 | 3.10 |
| Polysorbate 80 | 3.00 | | |
| sorbitan stearate (span 60) | | 3.60 | 2.90 |
| sorbitan oleate (span 80) | 4.40 | | |
| Glyceryl stearate | 1.00 | 1.50 | 1.00 |
| Cetostearyl alcohol | | | 2.00 |
| Sodium Carboxymethyl cellulose (30000) | 0.50 | | |
| Hydroxypropyl methylcellulose (Methocel K100M) | | 0.25 | 0.25 |
| Xanthan gum | | 0.25 | 0.25 |
| Purified water | 74.1 | 76.0 | 74.5 |
| Benzoyl Peroxide | 6.0 | 6.0 | 6.0 |
| Control: | 100.00 | 100.00 | 100.00 |
| Propellant (AP-70) | 8.00 | 8.00 | 8.00 |

-continued

|  | 038 | 039 | 040 |
|---|---|---|---|
| Results | | | |
| QUALITY | FG | G-E | G-E |
| COLOR | | W | W |
| ODOR | | NO ODOR | NO ODOR |
| SHAKABILITY | | GOOD | GOOD |

Comments: The combination of Methocel/xanthan gum appeared to be more effective than a single polymer sodium CMC with 10% volatile silicone.

Manufacturing Procedure (038)
Step 1: Preparation of Oily Phase (A)
Heat all ingredients to 65 C to complete dissolution.
Step 2: Preparation of Water Phase (B)
Heat water to 65 C. Add Sodium Carboxymethyl cellulose while vigorously mixing Add polysorbate 80.
Step 3: Preparation of PFF
Add A to B while mixing. Cool to RT
Add Benzoyl peroxide. Mix thoroughly while cooling with ice.
add water if necessary to obtain the correct weight.
Step 2: Canisters Filling and Crimping
Fill canister with PFF and crimped with valves
Step 3: Pressurizing
Canisters are filled with 8% propellant.

Manufacturing Procedure (039, 040)
Step 1: Preparation of Oily Phase (A)
Heat all ingredients to 65 C to complete dissolution.
Step 2: Preparation of Water Phase (B)
Add Methocel K100M to water at 5-20 C while vigorously mixing. Heat to 60 C and Add Xanthan gum while mixing. Add polysorbate 80.
Step 3: Preparation of PFF
Add A to B while mixing. Cool to 40 C. Add Cyclomethicone. Cool to RT
Add Benzoyl peroxide. Mix thoroughly while cooling with ice.
add water if necessary to obtain the correct weight.
Step 2: Canisters Filling and Crimping
Fill canister with PFF and crimped with valves
Step 3: Pressurizing
Canisters are filled with 8% propellant.

Section B

Example 11

Non Oleaginous Formulation with and without a Moisturizing Complex of Glycerin and Sodium pCA

|  | 004 | 006 | 011 | 014 |
|---|---|---|---|---|
| BPO | 6 | 6 | 6 | 6 |
| Cyclomethicone | 1 | 1 | 1 | 1 |
| Steareth-21 | — | 2 | 2 | — |
| Steareth-2 | — | 3 | 3 | — |
| PEG-40 Stearate | 3 | — | — | 3 |
| Polysorbate 60 | 1 | — | — | 1 |
| Glyceryl monostearate | 1 | 1 | 1 | 1 |
| Stearyl alcohol | 1 | 1 | 1 | 1 |
| Sodium CMC | 1 | 1 | — | — |
| Xanthan gum | — | — | 0.35 | 0.35 |

-continued

|  | 004 | 006 | 011 | 014 |
|---|---|---|---|---|
| Methocel K100 | — | — | 0.35 | 0.35 |
| Citric acid | 0.31 | 0.31 | 0.31 | 0.31 |
| Sodium Citrate | 0.44 | 0.44 | 0.44 | 0.44 |
| Glycerin | 8 | — | 8 | — |
| Sodium PCA | 2 | — | 2 | — |
| Purified water | 75.25 | 84.25 | 74.55 | 85.55 |
| Propellant | AP-70 | AP-70 | AP-70 | 1681 |
| PFF | | | | |
| Centrifugation 3k (%) | 20% sedim | — | — | 10% sedim |
| Centrifugation 10k (%) | 20% sedim | — | 20% sedim | 20% sedim |
| Viscosity (PFF) (cps) | 5575 | — | 24864 | 6818 |
| Microscopic observation | agglom. | — | agglom | agglom |
| pH direct | 4.61 | — | 4.49 | 4.37 |
| Foam | | | | |
| Foam Quality | G | FG | G | G |
| Density (g/mL) | 0.036 | — | — | — |
| Shakability | 1 | 0 | 0 | 1 |
| Collapse Time | >300/FG | — | >300/G | >300/FG |

Comments: Replacing the surfactant system stearate21/stearate2 with PEG 40 Stearate and Polysorbate 60 improved the shakability of the formulations. The quality of the formulations with xanthan/Methocel appeared to be better. The presence of glycerin/sodium PCA may also help. The suspended BPO as expected precipitated on centrifugation (agglom=agglomeration). The moisture agents (glycerin and sodium PCA) affect the properties of the formulation, however, such moisture agents are preferred in a formulation containing BPO because BPO has a drying effect on skin.

Manufacturing Procedure (004, 006-w/o 4.1)
Step 1: Preparation of Water Phase (B)
1.1. Heat water to 65-70° C., add slowly CMC while vigorously stirring
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool the emulsion to 40° C.
Step 4: Glycerin, Sodium PCA and buffer addition
4.1. Add glycerine and sodium PCA to the emulsion while mixing thoroughly.
4.2. Cool to RT and not more then 30° C.
4.3. Add Citric acid and sodium citrate tribasic dihydrate to the water and mix.
Step 5: Homogenization
5.1. Add Benzoyl peroxide and homogenize 15 minutes
Step 6: pH adjustment
6.1. Verify temperature emulsion is less than 30° C. Check pH, to obtain a pH of 4.5±0.2.
6.2. Add water if necessary to obtain the correct weight.
Step 7: Canisters Filling and Crimping
Fill canister with PFF and crimped with valves
Step 8: Pressurizing
Canisters are filled with 8% propellant.
Manufacturing Procedure (011, 014-w/o 4.1)
Step 2: Preparation of water Phase (B)
1.1. Heat part of water to 90° C., Add Methocel K100M with vigorous agitation until thoroughly wetted and evenly dispersed, no clumps are detected. Cool the rest of water. Add the hot water to the cool water while mixing until homogeneous and no particles are observed.

1.2. Heat (Step 1.1) to 50° C., add Xanthan gum with vigorous mixing. Keep temperature at 70.
1.3. Add all other water phase ingredients and heat to 70° C. to obtain complete dissolution of all ingredients.

Step 2: Preparation of Oil Phase (A)
2.1. Heat all ingredients of the oil phase to 70° C. until complete melting and homogeneity is obtained.

Step 3: Emulsification
3.1. Add the oil phase to the water phase at 65-70° C. with agitation
3.2. Agitation continues until PFF uniformity is reached.
3.3. Cool the emulsion to 40° C.

Step 4: Glycerin, Sodium PCA and buffer addition
4.1. Add glycerine and sodium PCA to the emulsion while mixing thoroughly.
4.2. Cool to RT and not more then 30° C.
4.3. Add Citric acid and sodium citrate tribasic dihydrate to the water and mix.

Step 5: Homogenization
5.1. Add Benzoyl peroxide and homogenize for 15 minutes while cooling with ice bath.

Step 6: pH adjustment
6.1. Verify temperature emulsion is less than 30° C. Check pH, to obtain a pH of 4.5±0.2.
6.2. Add water if necessary to obtain the correct weight.

Step 7: Canisters Filling and Crimping
Fill canister with PFF and crimped with valves Step 8: Pressurizing
Canisters are filled with 8% propellant.

Example 12

Oleaginous Formulation of 6% Mineral Oil with and without a Moisturizing Complex of Glycerin and Sodium pCA

| | 005 | 007 | 008 | 012 | 013 |
|---|---|---|---|---|---|
| BPO | 6 | 6 | 6 | 6 | 6 |
| Mineral oil | 6 | 6 | 6 | 6 | 6 |
| Cyclomethicone | 1 | 1 | 1 | 1 | 1 |
| Steareth-21 | — | — | — | 2 | 2 |
| Steareth-2 | — | — | — | 3 | 3 |
| PEG-40 Stearate | 3 | 3 | 3 | — | — |
| Polysorbate 60 | 1 | 1 | 1 | — | — |
| Glyceryl monostearate | 1 | 1 | 1 | 1 | 1 |
| Stearyl alcohol | 1 | 1 | 1 | 1 | 1 |
| Sodium CMC | 0.5 | 1 | — | 0.5 | — |
| Xanthan gum | — | — | 0.35 | — | 0.35 |
| Methocel K100 | — | — | 0.35 | — | 0.35 |
| Citric acid | 0.31 | 0.31 | 0.31 | 0.31 | 0.31 |
| Sodium Citrate | 0.44 | 0.44 | 0.44 | 0.44 | 0.44 |
| Glycerin | 8 | 8 | 8 | — | — |
| Sodium PCA | 2 | 2 | 2 | — | — |
| Purified water | 69.75 | 69.25 | 69.55 | 78.75 | 78.55 |
| Propellant PFF | AP-70 | AP-70 | AP-70 | AP-70 | AP-70 |
| Centrifugation 3k (%) | — | 15% sedim | 10% sedim | — | — |
| Centrifugation 10k (%) | — | 15% sedim | 20% sedim 20% cream | 20% sedim | 20% sedim |
| Viscosity (PFF) (cps) | — | — | 6218 | — | 30486 |
| Microscopic observation | — | agglom | agglom | — | no agglom |
| pH direct Foam | — | 4.59 | 4.48 | 4.60 | 4.60 |
| Foam Quality | FG | G | G | G− | G |
| Density (g/mL) | — | — | 0.034 | — | — |
| Shakability | 2 | 1 | 1 | 0 | 0 |
| Collapse Time | — | — | >300/FG | — | 60/F |

Comments: By increasing the amount of polymer the foam quality was improved and good quality foam was achieved. The formulations with the moisturizing complex were shakable. In contrast the formulations without the moisturizing complex had poor or no shakability but were flowable. Replacing the surfactant system stearate21/stearate2 with PEG 40 Stearate and Polysorbate 60 improved shakability of the formulations.

Manufacturing Procedure (005, 007, 012-w/o 4.1)

Step 1: Preparation of Water Phase (B)
1.1. Heat water to 65-70° C., add slowly CMC while vigorously stirring using paddle stirrer.

Step 2: Preparation of Oil Phase (A)
2.1. Heat all ingredients of the oil phase to 70° C. until complete melting and homogeneity is obtained.

Step 3: Emulsification
3.1. Add the oil phase to the water phase at 65-70° C. with agitation
3.2. Agitation continues until PFF uniformity is reached.
3.3. Cool the emulsion to 40° C.

Step 4: Glycerin, Sodium PCA and buffer addition
4.1. Add glycerine and sodium PCA to the emulsion while mixing thoroughly.
4.2. Cool to RT and not more then 30° C.
4.3. Add Citric acid and sodium citrate tribasic dihydrate to the water and mix.

Step 5: Homogenization
5.1. Add Benzoyl peroxide and homogenize for 15 minutes while cooling with ice bath.

Step 6: pH adjustment
6.1. Verify temperature emulsion is less than 30° C. Check pH to obtain a pH of 4.5±0.2.
6.2. add water if necessary to obtain the correct weight.

Step 7: Canisters Filling and Crimping
Fill canister with PFF and crimped with valves Step 8: Pressurizing
Canisters are filled with 8% propellant.

Manufacturing Procedure (008, 013-w/o 4.1)

Step 1: Preparation of Water Phase (B)
1.4. Heat part of water to 90° C., Add Methocel K100M with vigorous agitation until thoroughly wetted and evenly dispersed, no clumps are detected. Cool the rest of water. Add the hot water to the cool water while mixing until homogeneous and no particles are observed.
1.5. Heat to 50° C., add Xanthan gum with vigorous mixing. Keep temperature at 70.
1.6. Add all other water phase ingredients and heat to 70° C. to obtain complete dissolution of all ingredients.

Step 2: Preparation of Oil Phase (A)
2.2. Heat all ingredients of the oil phase to 70° C. until complete melting and homogeneity is obtained.

Step 3: Emulsification
3.4. Add the oil phase to the water phase at 65-70° C. with agitation using 4-blade impeller.
3.5. Agitation continues until PFF uniformity is reached.
3.6. Cool the emulsion to 40° C.
Step 4: Glycerin, Sodium PCA and buffer addition
4.1. Add glycerine and sodium PCA to the emulsion while mixing thoroughly.
4.2. Cool to RT and not more then 30° C.
4.3. Add Citric acid and sodium citrate tribasic dihydrate to the water and mix.
Step 5: Homogenization and Benzoyl Peroxide addition
5.1. Start homogenization while cooling with ice bath. Add Benzoyl peroxide and keep homogenisation for 15 minutes.
Step 6: pH adjustment
6.1. Verify temperature emulsion is less than 30° C. Check pH, to obtain a pH of 4.5±0.2.
6.2. add water if necessary to obtain the correct weight.
Step 7: Canisters Filling and Crimping
Fill canister with PFF and crimped with valves
Step 8: Pressurizing
Canisters are filled with 8% propellant.

Example 13

Oleaginous Formulation with 6% MCT with and without a Moisturizing Complex of Glycerin and Sodium pCA

|  | 009 | 010 | 015 | 016 |
|---|---|---|---|---|
| BPO | 6 | 6 | 6 | 6 |
| MCT oil | 6 | 6 | 6 | 6 |
| Cyclomethicone | 1 | 1 | 1 | 1 |
| Steareth-21 | — | 2 | 2 | — |
| Steareth-2 | — | 3 | 3 | — |
| PEG-40 Stearate | 3 | — | — | 3 |
| Polysorbate 60 | 1 | — | — | 1 |
| Glyceryl monostearate | 1 | 1 | 1 | 1 |
| Stearyl alcohol | 1 | 1 | 1 | 1 |
| Sodium CMC | — | 0.5 | — | 0.5 |
| Xanthan gum | 0.35 | — | 0.35 | — |
| Methocel K100 | 0.35 | — | 0.35 | — |
| Citric acid | 0.31 | 0.31 | 0.31 | 0.31 |
| Sodium Citrate | 0.44 | 0.44 | 0.44 | 0.44 |
| Glycerin | — | 8 | 8 | — |
| Sodium PCA | — | 2 | 2 | — |
| Purified water | 79.55 | 68.75 | 68.55 | 79.75 |
| Propellant PFF | AP-70 | AP-70 | AP-70 | AP-70 |
| Centrifugation 3k (%) | 10% sedim | — | — | 20% sedim |
| Centrifugation 10k (%) | 10% sedim | 10% sedim | 20% sedim | 20% sedim 40% cream |
| Viscosity (PFF) (cps) | 6423 | 20183 | — | — |
| Microscopic observation | no agglom | agglom | agglom | agglom |
| pH direct | 4.30 | 4.57 | 4.46 | 4.39 |
| Foam |  |  |  |  |
| Foam Quality | G | G− | G | G |
| Density (g/mL) | — | — | — | — |
| Shakability | 1 | 0 | 0 | 2 |
| Collapse Time | >300/G | 30/F | >300/G | >300/FG |

Comments: When mineral oil was replaced by MCT then surprisingly the position was reversed with the moisturizing complex instead had poor shakability. Good quality foam was achieved.

Manufacturing Procedure (009)
Step 1: Preparation of Water Phase (B)
1.1. Heat part of water to 90° C., Add Methocel K100M with vigorous agitation until thoroughly wetted and evenly dispersed, no clumps are detected. Cool the rest of water. Add the hot water to the cool water while mixing until homogeneous and no particles are observed. The temperature should not exceed 10-15° C.
1.2 Heat to 50° C., add Xanthan gum with vigorous mixing. Keep temperature at 70.
1.3 Add all other water phase ingredients and heat to 70° C. to obtain complete dissolution of all ingredients.
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool the emulsion to RT and not more then 30° C.
Step 4: Buffer addition
4.1. Add Citric acid and sodium citrate tribasic dihydrate to the water and mix.
Step 5: Homogenization
5.1. Add Benzoyl peroxide and homogenize for 15 minutes while cooling with ice bath.
Step 6: pH adjustment
6.1. Verify temperature emulsion is less than 30° C. Check pH, to obtain a pH of 4.5±0.2.
6.2. add water if necessary to obtain the correct weight.
Step 7: Canisters Filling and Crimping
Fill canister with PFF and crimped with valves
Step 8: Pressurizing
Canisters are filled with 8% propellant.
Manufacturing Procedure (010)
Step 1: Preparation of Water Phase (B)
1.1. Heat water to 65-70° C., add CMC while vigorously stirring.
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool the emulsion to 40° C.
Step 4: Glycerin, Sodium PCA and buffer addition
4.1. Add glycerine and sodium PCA to the emulsion while mixing thoroughly.
4.2. Cool to RT and not more then 30° C.
4.3. Add Citric acid and sodium citrate tribasic dihydrate to the water and mix.
Step 5: Homogenization
5.1. Add Benzoyl peroxide and homogenize for 15 minutes at 8000 RPMs while cooling with ice bath.
Step 6: pH adjustment
6.1. Verify temperature emulsion is less than 30° C. Check pH, to obtain a pH of 4.5±0.2.
6.2. Add water if necessary to obtain the correct weight.
Step 7: Canisters Filling and Crimping
Fill canister with PFF and crimped with valves
Step 8: Pressurizing
Canisters are filled with 8% propellant.
Manufacturing Procedure (015)
Step 1: Preparation of Water Phase (B)
1.1 Heat part of water to 90° C., Add Methocel K100M with vigorous agitation until thoroughly wetted and evenly dispersed, no clumps are detected. Cool the rest of water. Add the hot water to the cool water while mixing until homogeneous and no particles are observed.
1.2 Heat to 50° C., add Xanthan gum with vigorous mixing. Keep temperature at 70.
1.3 Add all other water phase ingredients and heat to 70° C. to obtain complete dissolution of all ingredients.
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool the emulsion to 40° C.
Step 4: Glycerin, Sodium PCA and buffer addition
4.1. Add glycerine and sodium PCA to the emulsion while mixing thoroughly.
4.2. Cool to RT and not more then 30° C.
4.3. Add Citric acid and sodium citrate tribasic dihydrate to the water and mix.
Step 5: Homogenization
5.1. Add Benzoyl peroxide and homogenize for 15 minutes while cooling with ice bath.

Step 3: Emulsification
3.1. Add the oil phase to the water phase at 65-70° C. with agitation
3.2. Agitation continues until PFF uniformity is reached.
3.3. Cool the emulsion to RT and not more then 30° C.
Step 4: Buffer addition
4.1. Add Citric acid and sodium citrate tribasic dihydrate to the water and mix.
Step 5: Homogenization
5.1. Add Benzoyl peroxide and homogenize for 15 minutes while cooling with ice bath.
Step 6: pH adjustment
6.1. Verify temperature emulsion is less than 30° C. Check pH, to obtain a pH of 4.5±0.2.
6.2. Add water if necessary to obtain the correct weight.
Step 7: Canisters Filling and Crimping
Fill canister with PFF and crimped with valves
Step 8: Pressurizing
Canisters are filled with 8% propellant.

Example 14

Oleaginous Placebo Oil/Silicone Containing Formulations with and without a Moisturizing Complex of Glycerin and Sodium pCA

| | Treatment | | | | | |
|---|---|---|---|---|---|---|
| | 1 | 2 | 3 | 4 | 5 | 6 |
| | Formulation | | | | | |
| | BPO-008-071126P | BPO-016-071126P | BPO-invest-042-071125P | BPO-014-071126P | BPO-invest-041-071125P | BPO-invest-043-071126P |
| Mineral oil | 6.00 | — | 6.00 | — | — | — |
| MCT oil | — | 6.00 | — | — | — | 6.00 |
| Cyclomethicone | 1.00 | 1.00 | 1.00 | 1.00 | 1.00 | 1.00 |
| PEG-40 Stearate | 3.00 | 3.00 | 3.00 | 3.00 | 3.00 | 3.00 |
| Polysorbate 60 | 1.00 | 1.00 | 1.00 | 1.00 | 1.00 | 1.00 |
| Glyceryl monostearate | 1.00 | 1.00 | 1.00 | 1.00 | 1.00 | 1.00 |
| Stearyl alcohol | 1.00 | 1.00 | 1.00 | 1.00 | 1.00 | 1.00 |
| Hydroxypropyl methylcellulose | 0.35 | — | 0.35 | 0.35 | 0.35 | — |
| Xanthan gum | 0.35 | — | 0.35 | 0.35 | 0.35 | — |
| Sodium CMC | — | 0.50 | — | — | — | 0.50 |
| Purified water | 75.55 | 85.75 | 85.55 | 91.55 | 81.55 | 75.75 |
| Glycerin | 8.00 | — | — | — | 8.00 | 8.00 |
| Sodium PCA | 2.00 | — | — | — | 2.00 | 2.00 |
| Citric acid | 0.31 | 0.31 | 0.31 | 0.31 | 0.31 | 0.31 |
| Sodium citrate tribasic dehydrate | 0.44 | 0.44 | 0.44 | 0.44 | 0.44 | 0.44 |
| Control: | 100.00 | 100.00 | 100.00 | 100.00 | 100.00 | 100.00 |
| Propellant (AP-70) | 8.00 | 8.00 | 8.00 | 8.00 | 8.00 | 8.00 |

Step 6: pH adjustment
6.1. Verify temperature emulsion is less than 30° C. Check pH, to obtain a pH of 4.5±0.2.
6.2. Add water if necessary to obtain the correct weight.
Step 7: Canisters Filling and Crimping
Fill canister with PFF and crimped with valves
Step 8: Pressurizing
Canisters are filled with 8% propellant.
Manufacturing Procedure (016)
Step 1: Preparation of Water Phase (B)
1.1. Heat water to 65-70° C., add slowly CMC while stirring.
Step 2: Preparation of Oil Phase (A)
2.1. Heat all ingredients of the oil phase to 70° C. until complete melting and homogeneity is obtained.

Comments: The advantages of formulations with and without the moisturizing complex glycerin/pCA were explored with and without mineral oil or MCT oil. Chemical stability results with and without the moisturizing complex are shown below in Example 24.
Manufacturing Procedure for Treatment 1, 2 and 4—Describe in Section B (Just without B)
Manufacturing Procedure (041)
Step 1: Preparation of Water Phase (B)
1.1. Heat part of water to 90° C., Add Methocel K100M with vigorous agitation until thoroughly wetted and evenly dispersed, no clumps are detected. Cool the rest of water. Add the hot water to the cool water while mixing until homogeneous and no particles are observed. The temperature should not exceed 10-15° C.

1.2. Heat to 50° C. slowly, add Xanthan gum with vigorous mixing. Keep temperature at 70.
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool the emulsion to 40° C.
Step 4: Glycerin, Sodium PCA and buffer addition
4.1. Add glycerine and sodium PCA to the emulsion while mixing thoroughly.
4.2. Cool to RT and not more than 30° C.
4.3. Add Citric acid and sodium citrate tribasic dihydrate to the water and mix.
Step 5: Homogenization
5.1. Start homogenization and keep homogenization for 15 minutes.
Step 6: pH adjustment
6.1. Verify temperature emulsion is less than 30° C. Check pH, to obtain a pH of 4.5±0.2.
6.2. Add water if necessary to obtain the correct weight.
Step 7: Canisters Filling and Crimping
Fill canister with PFF and crimped with valves
Step 8: Pressurizing
Canisters are filled with 8% propellant.
Manufacturing Procedure (042)
Step 1: Preparation of Water Phase (B)
1.1. Heat part of water to 90° C., Add Methocel K100M with vigorous agitation until thoroughly wetted and evenly dispersed, no clumps are detected. Cool the rest of water. Add the hot water to the cool water while mixing until homogeneous and no particles are observed. The temperature should not exceed 10-15° C.
1.2 Heat to 50° C., add Xanthan gum with vigorous mixing. Keep temperature at 70.
1.3 Add all other water phase ingredients and heat to 70° C. to obtain complete dissolution of all ingredients.
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool to RT.
Step 4: Buffer Addition
4.1. Add Citric acid and sodium citrate tribasic dihydrate to the water and mix.
Step 5: Homogenization
5.1. Homogenize for 15 minutes
Step 6: pH adjustment
6.1. Verify temperature emulsion is less than 30° C. Check pH, to obtain a pH of 4.5±0.2.
6.2. Add water if necessary to obtain the correct weight.
Step 7: Canisters Filling and Crimping
Fill canister with PFF and crimped with valves
Step 8: Pressurizing
Canisters are filled with 8% propellant.
Manufacturing Procedure (043)
Step 1: Preparation of Water Phase (B)
1.1. Heat water to 65-70° C., add slowly CMC while vigorously stirring using paddle stirrer.
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool the emulsion to 40° C.
Step 4: Glycerin, Sodium PCA and buffer addition
4.1. Add glycerine and sodium PCA to the emulsion while mixing thoroughly.
4.2. Cool to RT and not more then 30° C.
4.3. Add Citric acid and sodium citrate tribasic dihydrate to the water and mix.
Step 5: Homogenization
5.1. Start homogenization and keep homogenization for 15 minutes.
Step 6: pH adjustment
6.1. Verify temperature emulsion is less than 30° C. Check pH, to obtain a pH of 4.5±0.2.
6.2. add water if necessary to obtain the correct weight.
Step 7: Canisters Filling and Crimping
Fill canister with PFF and crimped with valves
Step 8: Pressurizing
Canisters are filled with 8% propellant.

Example 15

Placebo Formulations without BPO

| | Order of Appearance in Corneometer Study Figs | | | | | |
|---|---|---|---|---|---|---|
| | 4<br>014P | 2<br>016P | 1<br>008P | 5<br>041P | 3<br>042P | 6<br>043P |
| Mineral oil | | | 6.00 | | 6.00 | |
| MCT oil | | 6.00 | | | | 6.00 |
| Cyclomethicone | 1.00 | 1.00 | 1.00 | 1.00 | 1.00 | 1.00 |
| PEG-40 Stearate | 3.00 | 3.00 | 3.00 | 3.00 | 3.00 | 3.00 |
| Polysorbate 60 | 1.00 | 1.00 | 1.00 | 1.00 | 1.00 | 1.00 |
| Glyceryl monostearate | 1.00 | 1.00 | 1.00 | 1.00 | 1.00 | 1.00 |
| Stearyl alcohol | 1.00 | 1.00 | 1.00 | 1.00 | 1.00 | 1.00 |
| Hydroxypropyl methylcellulose | 0.35 | | 0.35 | 0.35 | 0.35 | |
| Xanthan gum | 0.35 | | 0.35 | 0.35 | 0.35 | |
| Sodium CMC | | 0.50 | | | | 0.50 |
| Purified water | 91.55 | 85.75 | 75.55 | 81.55 | 85.55 | 75.75 |
| Glycerin | | | 8.00 | 8.00 | | 8.00 |
| Sodium PCA | | | 2.00 | 2.00 | | 2.00 |

-continued

| | Order of Appearance in Corneometer Study Figs | | | | | |
|---|---|---|---|---|---|---|
| | 4<br>014P | 2<br>016P | 1<br>008P | 5<br>041P | 3<br>042P | 6<br>043P |
| Citric acid | 0.31 | 0.31 | 0.31 | 0.31 | 0.31 | 0.31 |
| Sodium citrate tribasic dehydrate | 0.44 | 0.44 | 0.44 | 0.44 | 0.44 | 0.44 |
| Control: | 100.00 | 100.00 | 100.00 | 100.00 | 100.00 | 100.00 |
| Propellant (ap-70) | 8.00 | 8.00 | 8.00 | 8.00 | 8.00 | 8.00 |
| Results | | | | | | |
| PFF | | | | | | |
| Viscosity (PFF) | 2290.51 | 445.91 | 1628.65 | 2388.49 | 2025.57 | 455.90 |
| Centrifugation 3k | stable | 80% Creaming | stable | stable | stable | 75% Creaming |
| Centrifugation 10k | 15% Creaming | 30% Creaming | 20% Creaming | 10% Creaming | 20% Creaming | 25% Creaming |
| Ph Undiluted Foam | 4.45 | 4.53 | 4.59 | 4.49 | 4.37 | 4.64 |
| Quality | E | E | E | E | E | E |
| Color | White | White | White | White | White | White |
| Odor | No odor | Very faint odor | No odor | Very faint odor | No odor | Very faint odor |
| Shakability | 1 | 2 | 2 | 1 | 2 | 2 |
| Density | 0.033 | 0.033 | 0.035 | 0.033 | 0.036 | 0.039 |
| Collapse Time | >300/G | >300/FG | >300/FG | >300/G | >300/G | >300/G |

Comments: All the formulations produced excellent quality foam with low density and good collapse time. All were resistant to centrifugation at 3K with only two formulations showing some creaming but no phase separation. All of the formulations were stable following centrifugation, indicating physical stability of the formulations. To determine which formulations would be compatible with human skin, studies were carried out to determine the skin-hydration effect of the formulations (see Example 16).

Example 16

A Double-Blind Study of the Skin-Hydration Effect of Glycerin Sodium PCA Vehicle of Example 14

Healthy subjects were applied with single dose of formulations as shown in Example 14. Skin hydration is measured using a Corneometer® CM 825 instrument. (Courage+ Khazaka, Koln, Germany). The measuring principle of the Corneometer® CM 825 is based on capacitance measurement of dielectric medium. Any change in the dielectric constant due to skin surface hydration alters the capacitance of a measuring capacitor. It is capable of detecting even slight changes in the skin hydration level.

Study Flow chart is shown below:

| STUDY ACTIVITY | Baseline* | 6 hours | 7 hours |
|---|---|---|---|
| Inclusion/exclusion criteria | X | | |
| Application of the test preparations | x | | |
| Assessment of skin hydration | | X | X |
| Assessment of tolerability parameters and Adverse Events | | X | X |

Skin hydration level is assessed at baseline (fifteen minutes after each subject washed the left and right forearms) with the Corneometer® CM 825. The formulations are applied in designated chambers under occlusion for 6 hours which are then removed and the skin cleaned. Hydration is then measured one hour later.

Study protocol: The study was performed in a temperature controlled room (20-24° C.). Subjects washed their arms with water (no soap) and dried their arms with dry paper towel. Formulations were applied using test chambers. The location of each chamber within the stripe was marked once applied (maximum of 3 stripes on each arm). Each stripe contained only one formulation. One stripe served as a control, non treated area. Three replicates of each formulation were applied. Formulations, control products and control non treated areas were randomly assigned to the treatment sites according to a randomization list, provided by the study statistician. The application array was unknown to the study operator and subjects. An amount of approximately 4 mg (40 ul) of each of the study formulations was applied on the treatment sites as described by the randomization list. Skin hydration level was assessed at baseline T=0 (minimum 15 minutes following rinse), using the Corneometer® CM 825, and tested based on study design.

Figure 3:
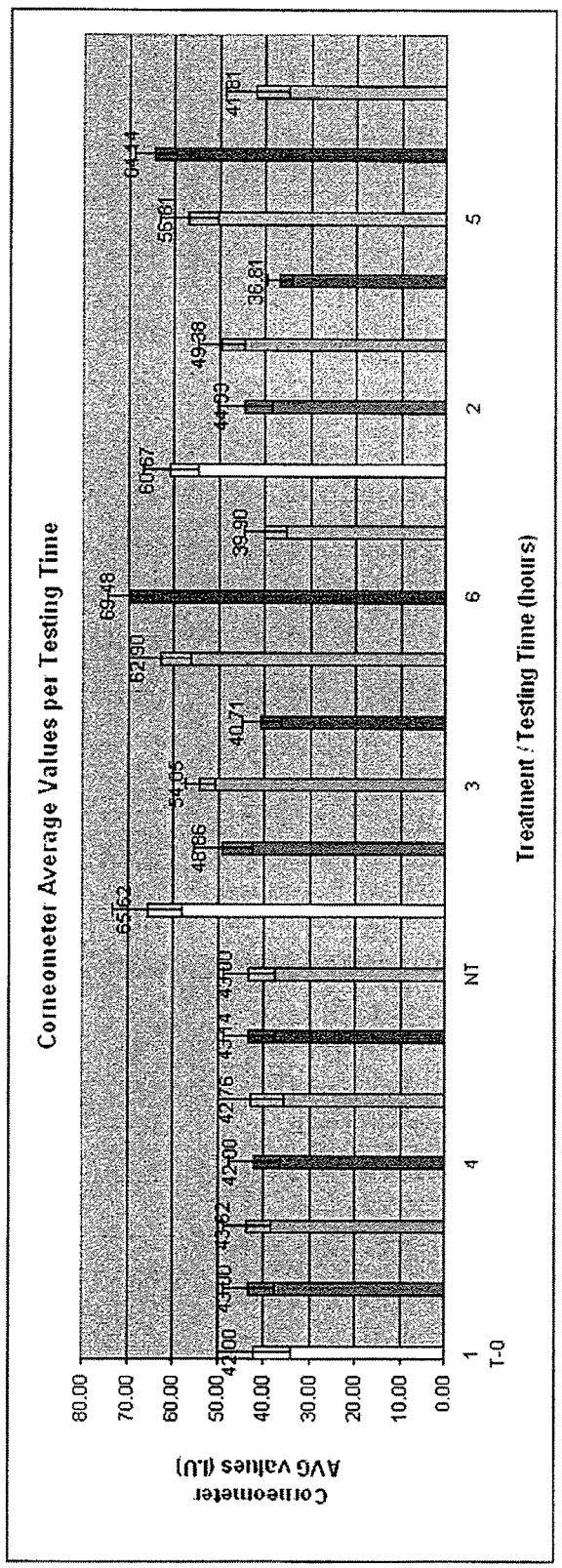
FIG. 3 shows Corneometer average values after treatment of skin using foamable compositions.
Figure 4:
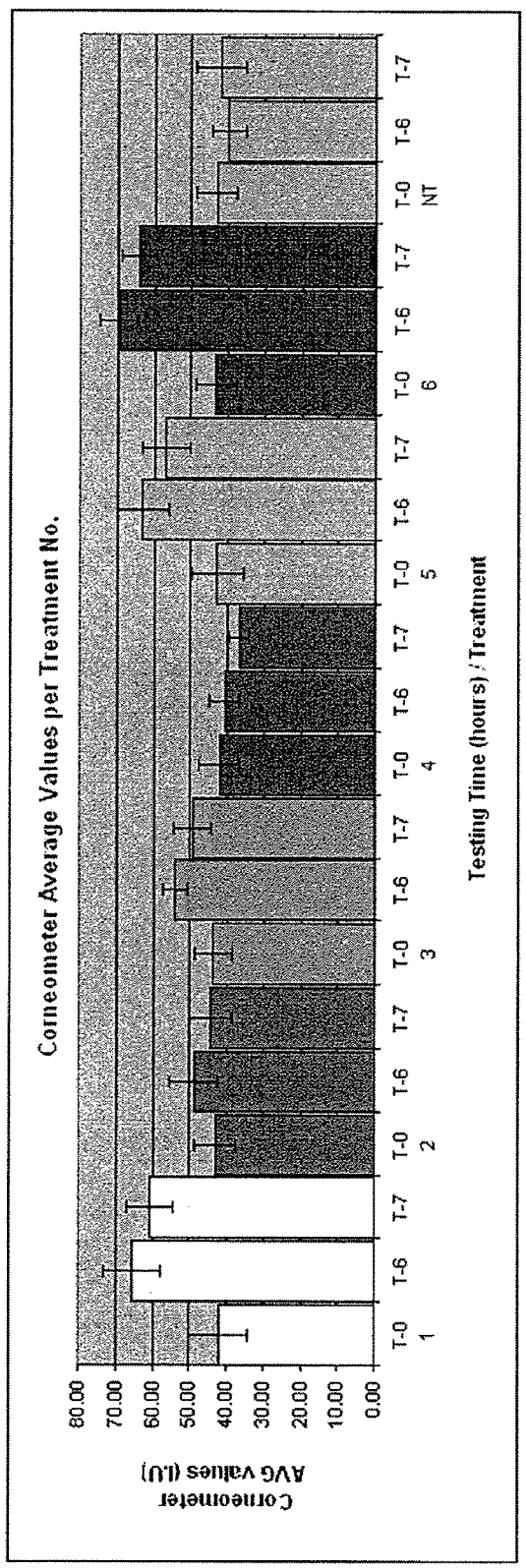
FIG. 4 shows Corneometer average values after treatment of skin using foamable compositions.
Figure 5:
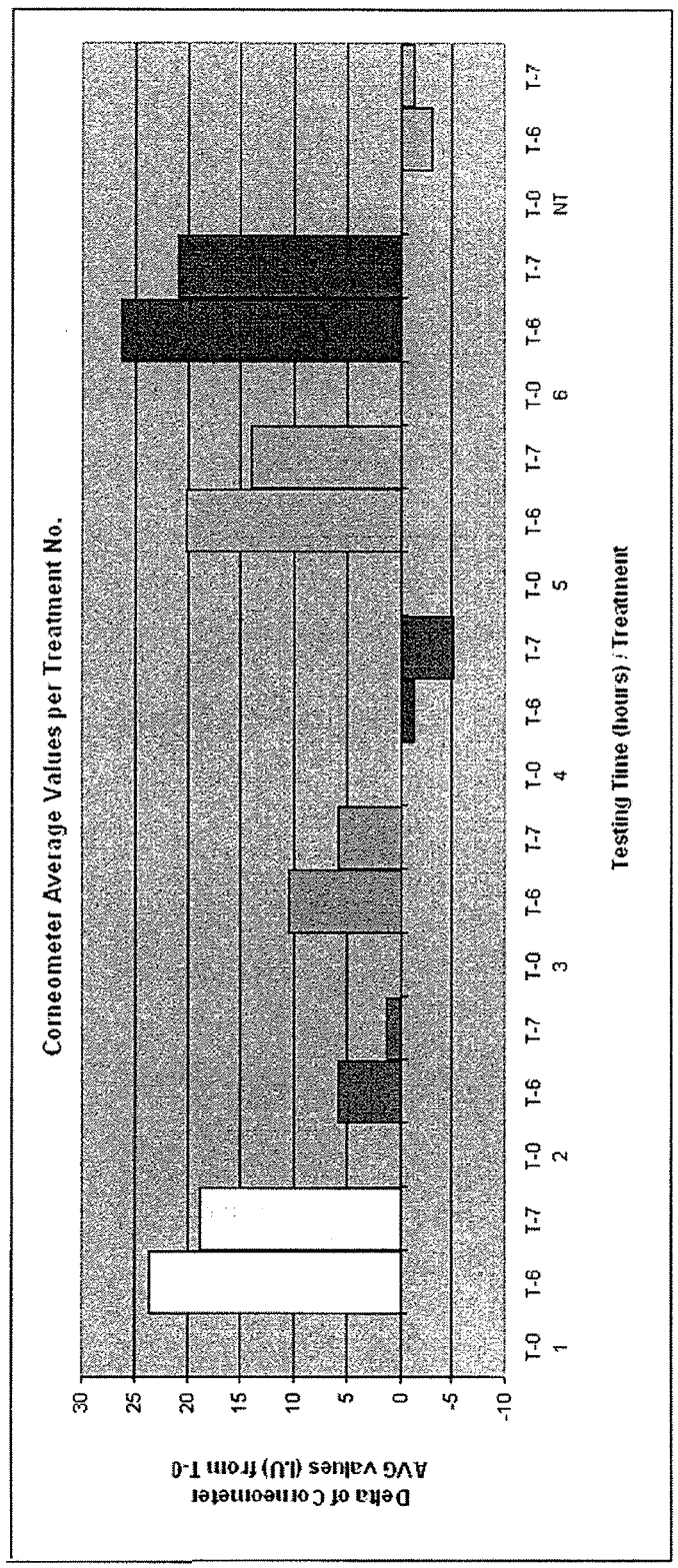
FIG. 5 shows Corneometer average values after treatment of skin using foamable compositions.

As shown in FIGS. 3-5, the formulations with glycerin/pCA have a substantial moisturizing effect when compared with the formulations lacking this combination. This is mostly beneficial since benzoyl proxide is known to cause undesired side effects such as skin dryness and irritation.

Example 17

Short Stability Study

| Ingredients | 008 | 014 | 016 |
|---|---|---|---|
| BPO | 6 | 6 | 6 |
| Mineral oil | 6 | — | — |
| MCT oil | — | — | 6 |
| Cyclomethicone | 1 | 1 | 1 |
| PEG-40 Stearate | 3 | 3 | 3 |
| Polysorbate 60 | 1 | 1 | 1 |
| Glyceryl monostearate | 1 | 1 | 1 |
| Stearyl alcohol | 1 | 1 | 1 |
| Sodium CMC | — | — | 0.5 |
| Xanthan gum | 0.35 | 0.35 | — |
| Methocel K100 | 0.35 | 0.35 | — |
| Citric acid | 0.31 | 0.31 | 0.31 |
| Sodium Citrate | 0.44 | 0.44 | 0.44 |
| Glycerin | 8 | — | — |
| Sodium PCA | 2 | — | — |
| Purified water | 69.55 | 85.55 | 79.75 |
| Propellant (propane, isobutane, butane) | 8 | 8 | 8 |

| | | 008 (PFF) | 008 (pressurized formulation) | 014 (PFF) | 014 (pressurized formulation) | 016 (PFF) | 016 (pressurized formulation) |
|---|---|---|---|---|---|---|---|
| API content (% w/w) | T-0 | 5.86 | 5.68 | 5.96 | 6.06 | 6.03 | 6.13 |
| | 2 Weeks/ 40° C. | 5.65 | 5.57 | 5.75 | 5.62 | 5.86 | 5.32 |
| | Degradation | | 1.94% | | 7.26% | | 13.2% |

Comments: Unexpectedly, the chemical stability of foamable compositions containing benzoyl peroxide appears to be significantly enhanced by adding moisturizing complex such as glycerin/pCA to the compositions. (Note in Example 17 the analytical method used BPO as a reference standard.)

So far as physical stability is concerned all these formulations without carbopol were homogenous on preparation but were found to separate over time. On shaking the separated formulations resuspended and were visually homogenous. In contrast, formulations with added carbopol, seen below in Example 23, remained homogenous for 6 months save that where some creaming was observed the creaming was readily reversible on shaking.

Section C

Example 18A

Comparison Between BPO Formulation with and without Carbopol

1. Formulations

| Ingredients | BPO-025 | BPO-032 |
|---|---|---|
| Cyclomethicone | 1.00 | 1.00 |
| PEG-40 Stearate | 3.00 | 3.00 |
| Polysorbate 60 | 1.00 | 1.00 |
| Glyceryl monostearate | 1.00 | 1.00 |
| Stearyl alcohol | 1.00 | 1.00 |
| Carbomer 934P (Carbopol 974P) | — | 0.35 |

-continued

| | 0.50 | 0.27 |
|---|---|---|
| Hydroxypropyl methylcellulose | | |
| Xanthan gum | 0.50 | 0.27 |
| Citric acid | 0.31 | 0.38 |
| Sodium citrate tribasic dihydrate | 0.44 | 0.59 |
| Hydrous benzoyl peroxide | 6.00 | 6.00 |
| Trolamine | — | 0.18 |
| Purified water | to 100 | to 100 |
| Propellant (AP-70) | 8 | 8 |

| Results | BPO 025 (To) | BPO 032 (To) |
|---|---|---|
| Shakability | Moderate | 2 |
| Foam Quality | Good | E |
| Foam Color | White | white |
| Foam Odor | No Odor | no odor |
| Density (mg/ml) | N\M* | 0.034 |
| pH diluted (1:5) | N\M* | 4.50 |
| Collapse Time (sec) | >300 | >300 |
| Expansion Time (sec) | N\M* | 50 |

N\M*—Not Measured

Figure 15:
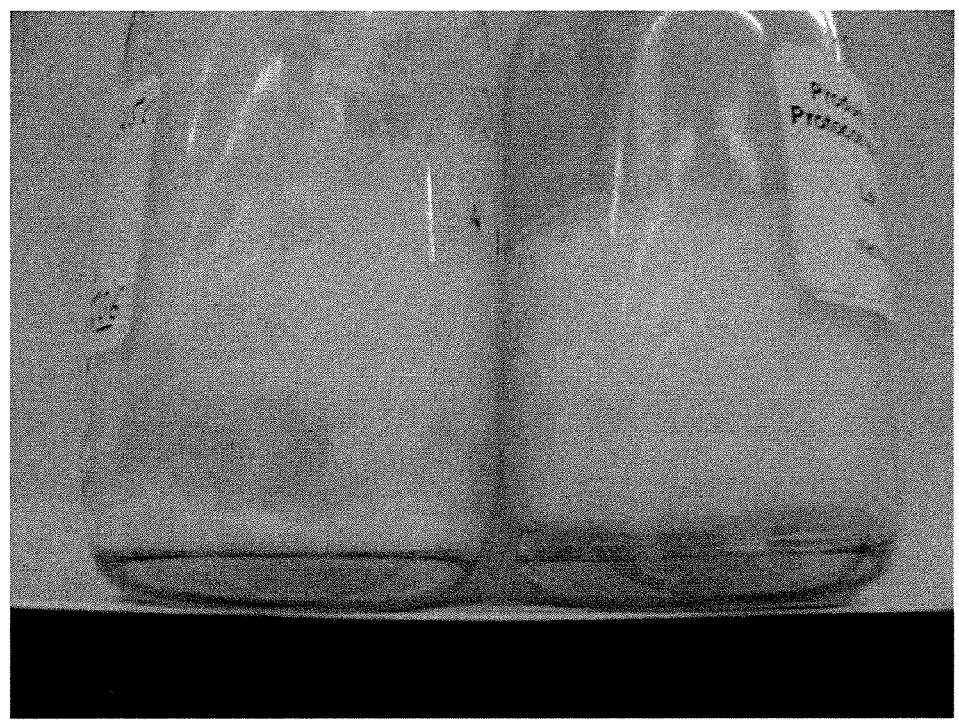
FIG. 15 shows formulations comprising propellant with and without carbomer.

Comments: In formulations (BPO-032, 035, 042, 047, 048) carbomer was added to hydroxypropylmethylcellulose and xanthan polymers, whose concentrations were in parallel reduced. Carbomer is a suspending agent and thickener. The unexpected advantage of this material is well observed in the homogeneity test (visual test). In formulation BPO-025 which does not have carbomer, migration of the particles to the bottom of the pressurized glass bottle can be seen in FIG. 15. In clear contrast in formulation BPO-032 which includes 0.35% carbomer, this phenomenon is not observed. Formulation BPO-032 as well as all other carbomer optimized formulation, looks homogeneous in particles aspect. FIG. 15 shows the effect of the presence and absence of carbomer after about 6 month at 25° C. The unexpected difference in homogeneity can be ascribed the addition of the buffered carbomer. It may be without being bound by any theory that somehow in the low viscous formulations the carbomer can maintain a fluid structural relationship with BPO which allows it to remain homogeneous even over time.

2. Procedure a) (BP032). See Example 23, part A for detailed procedure. In general terms where carbomer is used, base is added at the beginning to swell the polymer to form a gel. Subsequently after the oil phase is mixed with the aqueous phase to form a gel emulsion. The buffer (or pH adjuster) is added at the end of the procedure to produce a fluid low viscous emulsion to which the propellant is ultimately added.

b) (BP0025)

Step 1: Preparation of Water Phase (B)
1.1 Heat 70 g water to 70° C., add methocel with vigorous mixing until thoroughly wetted and evenly dispersed, no clumps are detected.
1.2 Cool to 50° C. and add Xanthan gum with vigorous mixing
1.3 Heat to 70° C.

Step 2: Preparation of Phase A
2.1. Heat all ingredients of phase A to 70° C. until complete melting and homogeneity is obtained.

Step 3: Emulsification
3.1. Add phase A to the water phase at 65-70° C. with agitation
3.2. Agitation continues until PFF uniformity is reached.
3.3. Cool to RT and not more than 30° C.
3.4. Check pH.

Step 4: Buffer addition
4.1. Add Citric acid and sodium citrate tribasic dihydrate to 25 g water and mix.
4.2. Add step 4.1 to step 3 and mix.
4.3. Check pH.
4.4. Check the final weight of emulsion and add water if necessary to obtain the correct weight.

Step 5: Homogenization and Benzyl Peroxide addition
5.1. Start homogenization step 4 while cooling with ice bath. Add Benzoyl peroxide and keep homogenization for 60 minutes until uniformity and no agglomeration is seen in microscopic observation.

Step 6: pH adjustment
6.1. Verify temperature emulsion (from step 5) is less than 30° C. Check pH, to obtain a pH of 4.5±0.2.

Step 7: Canisters Filling and Crimping
Fill canister with PFF and crimped with valves Step 8: Pressurizing
Canisters are filled with 8% propellant.

Example 18B

Comparison Between 1% BPO Formulation and 15% BPO Formulation with Carpopol

| phase | | BPO-47-1 (1%) | BPO-47-15 (15%) |
|---|---|---|---|
| A | Light mineral oil | 6.00 | 6.00 |
| | Cyclomethicone | 1.00 | 1.00 |
| | PEG-40 Stearate | 3.00 | 3.00 |
| | Polysorbate 60 | 1.00 | 1.00 |
| | Glyceryl monostearate | 1.00 | 1.00 |
| | Stearyl alcohol | 1.00 | 1.00 |
| B | Carbopol 981 solution | 0.50 | 0.50 |
| | Hydroxypropyl methylcellulose | 0.20 | 0.20 |
| | Xanthan gum | 0.20 | 0.20 |
| | Glycerin | 8.00 | 8.00 |
| | Sodium PCA | 2.00 | 2.00 |
| | Citric acid | 0.38 | 0.38 |
| | Sodium citrate tribasic dihydrate | 0.59 | 0.59 |
| | Benzoyl peroxide | 1.00 | 15.00 |
| | Sodium hydroxide 18% solution | 0.50 | 0.50 |
| | Purified water | to 100 | to 100 |
| | Propellant | 8.00 | 8.00 |
| Results: | | | |
| | Quality | E | E |
| | Color | white | white |
| | Odor | no odor | no odor |
| | Shakability | 2 | 2 |
| | Collapse Time | >180 | >180 |
| | Microscopic observation | crystals observed uniformity | crystals observed uniformity |
| | Bubble size | 71 | 91 |
| | Viscosity (PFF) | 1279.73 | 6558.6 |
| | viscosity + 8% pentane | 884.81 | 6494.62 |
| | % ratio viscosity between the foamable formulation with 8% pentane and the pre-foam formulation without pentane | 69.14 | 99.02 |

Procedure (for 1% and 15%):

Step 1: Preparation of Water Phase (B)
1.2. Add carbomer to water while mixing to dissolution and add base ("Carbomer solution"). In this formulation the base was sodium hydroxide. Heat carbomer solution and heat to 70° C. Add methocel with vigorous mixing.
1.3. Cool step 1.1 to 50° C. and add Xanthan gum with vigorous mixing.
1.4. Heat step 1.2 to 70° C.

Step 2: Preparation of Oil Phase (A)
2.2. Heat all ingredients of the oil phase to 70° C. until complete melting and homogeneity is obtained.

Step 3: Emulsification
3.1. Add the oil phase to the water phase at 65-70° C. with agitation
3.2. Agitation continues until PFF uniformity is reached.
3.3. Cool the emulsion to RT and not more than 40° C.
3.4. Add glycerin and sodium PCA to the emulsion while mixing thoroughly.
3.5. Cool to RT and not more than 30° C.
3.6. Check the final weight of emulsion and add water if necessary to obtain the correct weight.

Step 4: Buffer addition
4.1. Add Citric acid and sodium citrate tribasic dihydrate to 28 g water and mix.
4.2. Add to step 3 and mix.
4.3. Check pH.

Step 5: Homogenization and Benzyl Peroxide addition
5.1. Start homogenization step 4 while cooling with ice bath. Add Benzoyl peroxide and keep homogenization for 60 minutes.

Step 6: pH adjustment
- 6.1. Verify temperature emulsion is less than 30° C. Check pH, to obtain a pH of 4.5±0.2.
- 6.2. Add water if necessary to obtain the correct weight.

Step 7: Canisters Filling and Crimping
Fill canister with PFF and crimped with valves Step 8: Pressurizing
Canisters are filled with 8% propellant.

Comments: Both 1% and 15% BPO formulations achieved excellent, shakable non-breakable and uniform foam. These formulations were identical except for the amount of water and BPO present. In the high BPO formulation the water was 14% less. Increasing BPO's concentration dramatically caused an increase of the viscosity of the PFF. The viscosity remained high even when diluted with 8% pentane (a low volatile hydrocarbon) to simulate the volatile hydrocarbon propellants.

Example 19

10% BPO a) Comparison results between mineral oil emulsion formulations with different polymeric combinations.

| phase | Ingredients | BPC-054 | BPC-061 |
|---|---|---|---|
| A | Mineral oil | 6.00 | 6.00 |
| | Cyclomethicone | 1.00 | 1.00 |
| | PEG-40 Stearate | 3.00 | 3.00 |
| | Polysorbate 60 | 1.00 | 1.00 |
| | Glyceryl monostearate | 1.00 | 1.00 |
| | Stearyl alcohol | 1.00 | 1.20 |
| B | Carbomer 941 (Carbopol 981) | — | 0.25 |
| | Carbomer 940 (Carbopol 980) | 0.30 | — |
| | Crospovidone CL-M | 1.00 | — |
| | Hydroxypropyl methylcellulose | 0.10 | 0.10 |
| | Xanthan gum | 0.10 | 0.10 |
| | Glycerin | 8.00 | 8.00 |
| | Sodium PCA | 2.00 | 2.00 |
| | Citric acid | 0.38 | 0.38 |
| | Sodium citrate tribasic dihydrate | 0.59 | 0.59 |
| | Hydrous benzoyl peroxide | 10.00 | 10.00 |
| | Sodium hydroxide 18% solution | 0.30 | 0.25 |
| | Purified water | to 100 | to 100 |
| | Propellant (AP-70) | 8.00 | 8.00 |
| | Results: | | |
| | Quality | E | G+ |
| | Color | white | white |
| | Odor | no odor | no odor |
| | Shakability | 1 | 1 |
| | Density | 0.042 | 0.037 |
| | Collapse Time | >300 | >300 |
| | pH diluted | 4.65 | 4.62 |

Comments: Using a combination of a gelling agent, (Carbomer 940 (Carbopol 980) and a dispersing agent (Crospovidone CL-M) achieved excellent, shakable non-breakable foam. Changing gelling agent with much lower viscosity and dropping dispersing agent, caused a minimal decreasing to foam quality. Both formulations also had hydroxypropyl methylcellulose and xanthan present.

Procedure (for BPC054):

Step 1: Preparation of Water Phase (B)
- 1.1. Heat part of water to 70° C., add methocel with vigorous mixing until thoroughly wetted and evenly dispersed, no clumps are detected.
- 1.2. Add carbomer to water while mixing to dissolution and add base ("Carbomer solution"). Heat Carbomer solution to 50° C. while mixing.
- 1.3. Add step 1.1 to 1.2 and mix until no clumps are detected.
- 1.4. Adjust step 1.3 to 50° C. and add Xanthan gum with vigorous mixing
- 1.5. Heat step 1.4 to 70° C.
- 1.6. Heat another part of water to 70° C.
- 1.7. Add crospovidone to step 1.6 and mix.
- 1.8. Add step 1.7 to step 1.5 and mix.

Step 2: Preparation of Oil Phase (A)
- 2.1. Heat all ingredients of the oil phase to 70° C. until complete melting and homogeneity is obtained.

Step 3: Emulsification
- 3.1. Add the oil phase to the water phase at 65-70° C. with agitation
- 3.2. Agitation continues until PFF uniformity is reached.
- 3.3. Cool the emulsion to RT and not more than 40° C.
- 3.10 Add glycerin and sodium PCA to the emulsion while mixing thoroughly. Cool to RT and not more than 30° C. Check pH.

Step 4: Buffer addition
- 4.1. Add Citric acid and sodium citrate tribasic dihydrate to 8 g water and mix.
- 4.2. Add step 4.1 to step 3 and mix.
- 4.3. Check pH.
- 4.4. Add water if necessary to obtain the correct weight.

Step 5: Homogenization and Benzyl Peroxide addition
- 5.1. Start homogenization step 4 while cooling with ice bath. Add Benzoyl peroxide and keep homogenization for 60 minutes until uniformity and no agglomeration is seen in microscopic observation.

Step 6: pH adjustment
- 6.1. Verify temperature emulsion is less than 30° C. Check pH, to obtain a pH of 4.5±0.2.

Step 7: Canisters Filling and Crimping
Fill canister with PFF and crimped with valves Step 8: Pressurizing
Canisters are filled with 8% propellant.

Procedure (for BPC056):

Step 1: Preparation of Water Phase (B)
- 1.1. Heat 125 g water to 70° C., add methocel with vigorous mixing until thoroughly wetted and evenly dispersed, no clumps are detected.
- 1.2. Add carbomer to water while mixing to dissolution and add base ("Carbomer solution"). Add carbomer solution and mix until thoroughly wetted and evenly dispersed, no clumps are detected
- 1.3. Cool step 1.2 to 50° C. and add Xanthan gum with vigorous mixing
- 1.4. Heat step 1.3 to 70° C.
- 1.5. Heat 30 g water to 70° C.
- 1.6. Add crospovidone to step 1.5 and mix.
- 1.7. Add step 1.6 to step 1.4 and mix.

Step 2: Preparation of Oil Phase (A)
- 2.1 Heat all ingredients of the oil phase to 70° C. until complete melting and homogeneity is obtained.

Step 3: Emulsification
- 3.1. Add slowly the oil phase to the water phase at 65-70° C. with agitation
- 3.2. Agitation continues until PFF uniformity is reached.
- 3.3. Cool the emulsion to RT and not more than 30° C.
- 3.4. Check pH.

Step 4: Buffer addition
- 4.1. Add Citric acid and sodium citrate tribasic dihydrate to 17.5 g water and mix.
- 4.2. Add step 4.1 to step 3 and mix. Check pH.
- 4.3 add water if necessary to obtain the correct weight.

Step 5: Benzoyl Peroxide addition and Milling
  5.1. Place about ¼ of PFF quantity to the vessel while cooling with 10° C. external water bath and add slowly Benzoyl Peroxide to the PFF while mixing.
  5.2. Add the PFF left to the vessel while mixing Continue mixing until uniformity
Step 6: Canisters Filling and Crimping
  Fill canister with PFF and crimped with valves
Step 7: Pressurizing
  Canisters are filled with 8% propellant.

b) Comparison results between formulations without mineral oil containing 10% BPO

| Ingredients | BPC-057 | BPC-053 | BPC-060 |
|---|---|---|---|
| Cyclomethicone | 1.00 | 1.00 | 1.00 |
| PEG-40 Stearate | 3.00 | 3.00 | 3.00 |
| Polysorbate 60 | 1.00 | 1.00 | 1.00 |
| Glyceryl monostearate | 1.00 | 1.00 | 1.00 |
| Stearyl alcohol | 1.20 | 1.00 | 1.10 |
| Carbomer 934P (Carbopol 974P) | — | 0.35 | — |
| Carbomer 941 (Carbopol 981) | — | — | 0.20 |
| Carbomer 940 (Carbopol 980) | 0.25 | — | — |
| Crospovidone CL-M | 1.00 | — | 1.00 |
| Hydroxypropyl methylcellulose | 0.10 | 0.15 | 0.15 |
| Xanthan gum | 0.10 | 0.15 | 0.15 |
| Glycerin | 8.00 | — | — |
| Sodium PCA | 2.00 | — | — |
| Citric acid | 0.38 | 0.38 | 0.38 |
| Sodium citrate tribasic dihydrate | 0.59 | 0.59 | 0.59 |
| Hydrous benzoyl peroxide | 10.00 | 10.00 | 10.00 |
| Trolamine | — | 0.18 | — |
| Sodium hydroxide 18% solution | 0.25 | — | 0.20 |
| Purified water | to 100 | to 100 | to 100 |
| Propellant (AP-70) | 8.00 | 8.00 | 8.00 |
| Results | | | |
| Quality | E | G+ | G |
| Color | white | white | white |
| Odor | no odor | no odor | very faint odor |
| Shakability | 1 | 1 | 2 |
| Density | 0.033 | 0.035 | 0.040 |
| Collapse Time | >300 | >300 | >300 |
| pH diluted | 4.62 | 4.68 | 4.59 |

Comments: All formulations achieved good to excellent, shakable non-breakable foam. Glycerin and Sodium PCA appeared to have improved foam quality although there are also other small changes between formulations which may have contributed.

Procedure (for BPC053):
  Step 1: Preparation of Water Phase (B)
    1.1 Heat 70 g water to 70° C., add methocel with vigorous mixing until thoroughly wetted and evenly dispersed, no clumps are detected.
    1.2 Add carbomer to water while mixing to dissolution and add base ("Carbomer solution"). Heat carbomer solution to 50° C.
    1.3 Add step 1.1 to step 1.2 and mix until no clumps are detected.
    1.4 Adjust step 1.3 to 50° C. and add Xanthan gum with vigorous mixing
    1.5 Heat step 1.4 to 70° C.
  Step 2: Preparation of Oil Phase (A)
    2.1. Heat all ingredients of the oil phase to 70° C. until complete melting and homogeneity is obtained.
  Step 3: Emulsification
    3.1. Add the oil phase to the water phase at 65-70° C. with agitation
    3.2. Agitation continues until PFF uniformity is reached.
    3.3. Cool to RT and not more than 30° C.
    3.4. Check pH.
  Step 4: Buffer addition
    4.1. Add Citric acid and sodium citrate tribasic dihydrate to 17 g water and mix.
    4.2. Add step 4.1 to step 3 and mix.
    4.3. Check pH.
    4.4. Check the final weight of emulsion and add water if necessary to obtain the correct weight.
  Step 5: Homogenization and Benzyl Peroxide addition
    5.1. Start homogenization step 4 while cooling with ice bath. Add Benzoyl peroxide and keep homogenization for 60 minutes until uniformity
  Step 6: pH adjustment
    6.1. Verify temperature emulsion (from step 5) is less than 30° C. Check pH, to obtain a pH of 4.5±0.2.
  Step 7: Canisters Filling and Crimping
    Fill canister with PFF and crimped with valves
  Step 8: Pressurizing
    Canisters are filled with 8% propellant.

Procedure (for BPC057):
  Step 1: Preparation of Water Phase (B)
    1.1. Heat 45 g water to 70° C., add methocel with vigorous mixing until thoroughly wetted and evenly dispersed, no clumps are detected.
    1.2. Add carbomer to water while mixing to dissolution and add base ("Carbomer solution"). Heat Carbomer solution to 50° C. while mixing.
    1.3. Add step 1.1 to 1.2 and mix until no clumps are detected.
    1.4. Adjust step 1.3 to 50° C. and add Xanthan gum with vigorous mixing
    1.5. Heat step 1.4 to 70° C.
    1.6. Heat 30 g water to 70° C.
    1.7. Add crospovidone to step 1.6 and mix.
    1.8. Add step 1.7 to step 1.5 and mix.
  Step 2: Preparation of Oil Phase (A)
    2.1. Heat all ingredients of the oil phase to 70° C. until complete melting and homogeneity is obtained.
  Step 3: Emulsification
    3.1. Add the oil phase to the water phase at 65-70° C. with agitation
    3.2. Agitation continues until PFF uniformity is reached.
    3.3. Cool the emulsion to RT and not more than 40° C.
    3.4. Add glycerin and sodium PCA to the emulsion while mixing thoroughly.
    3.5. Cool to RT and not more than 30° C.
    3.6. Check pH.
  Step 4: Buffer addition
    4.1. Add Citric acid and sodium citrate tribasic dihydrate to 10 g water and mix.
    4.2. Add step 4.1 to step 3 and mix.
    4.3. Check pH.
    4.4. add water if necessary to obtain the correct weight.
  Step 5: Homogenization and Benzyl Peroxide addition
    5.1. Start homogenization step 4 while cooling with ice bath. Add Benzoyl peroxide and keep homogenization for 60 min. until uniformity and no agglomeration is seen in microscopic observation.
  Step 6: pH adjustment
    6.1. Verify temperature emulsion is less than 30° C. Check pH, to obtain a pH of 4.5±0.2.

Step 7: Canisters Filling and Crimping
Fill canister with PFF and crimped with valves
Step 8: Pressurizing
Canisters are filled with 8% propellant.

Procedure (for BPC060):
Step 1: Preparation of Water Phase (B)
1.1 Add to 300 g water:methocel, Carbomer, base and Xanthan gum while mixing with Jet impeller for 45 min.
1.2 Heat step 1.1 to 70° C.
1.3 Heat 75 g water to 70° C.
1.4 Add crospovidone to step 1.3 and mix.
1.5 Add step 1.4 to step 1.3 and mix.
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool to RT and not more than 30° C.
3.4. Check pH.
3.5. Check the final weight of emulsion and add water if necessary to obtain the correct weight.
Step 4: Benzoyl Peroxide addition and Milling
4.1. Place about ¼ of PFF quantity to the vessel while cooling with 10° C. external water bath and add slowly Benzoyl Peroxide to the PFF while mixing.
4.2. Continue mixing until uniformity and no agglomeration is seen in microscopic observation.
Step 5: Buffer addition
5.1. Add NaOH 18% and mix.
5.2. Check pH.
5.3. Add Citric acid and sodium citrate tribasic dihydrate to 10 g water and mix.
5.4. Add step 5.1 to step 4 and mix.
5.5. Check pH.
Step 6: Canisters Filling and Crimping
Fill canister with PFF and crimped with valves
Step 7: Pressurizing
Canisters are filled with 8% propellant.

Example 20

Preliminary Hydration Tests Comparing Formulations with and w/o Carbopol

Study protocol: See example 16. The procedure adopted is along the lines as described therein.

| STUDY ACTIVITY | Baseline* | 6 hours | 7 hours |
|---|---|---|---|
| Inclusion/exclusion criteria | x | | |
| Application of the test preparations | x | | |
| Assessment of skin hydration | | X | X |
| Assessment of tolerability parameters and Adverse Events | | X | X |

| Treatment ID | Treatment Name | Carbopol 981 | Methocel | Xanthan |
|---|---|---|---|---|
| A | No treatment | | | |
| B | BPO 008-081110P | No | Yes | Yes |
| C | BPO 047-081110P | Yes | Yes | Yes |

Figure 6:
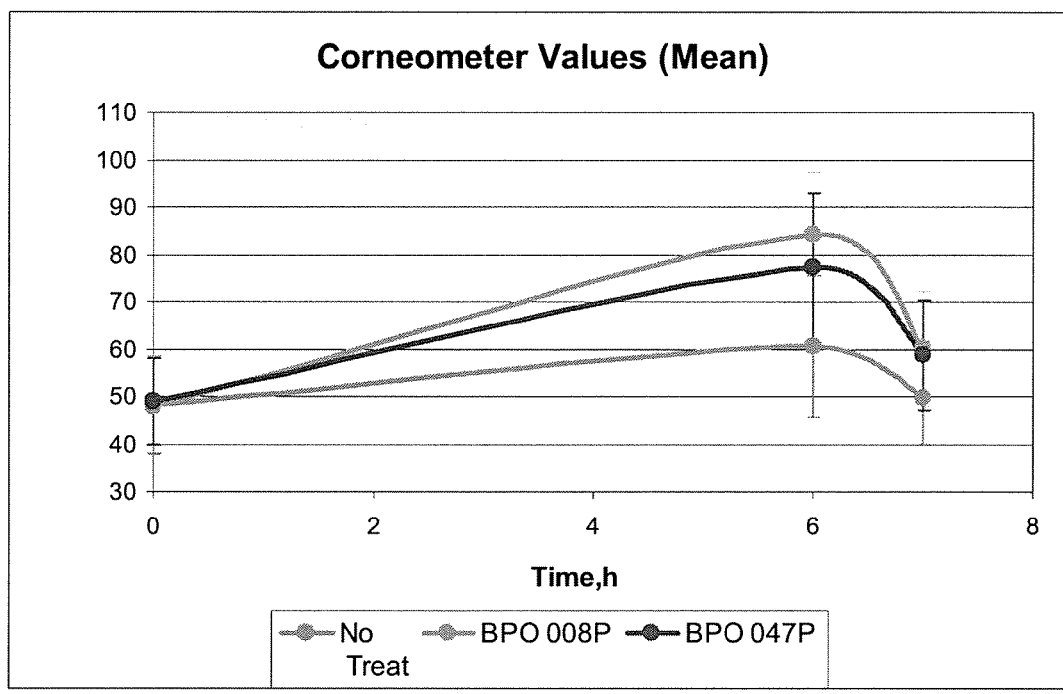
FIG. 6 shows Corneometer average values after treatment of skin using foamable compositions with and without carbomer.
Figure 7:
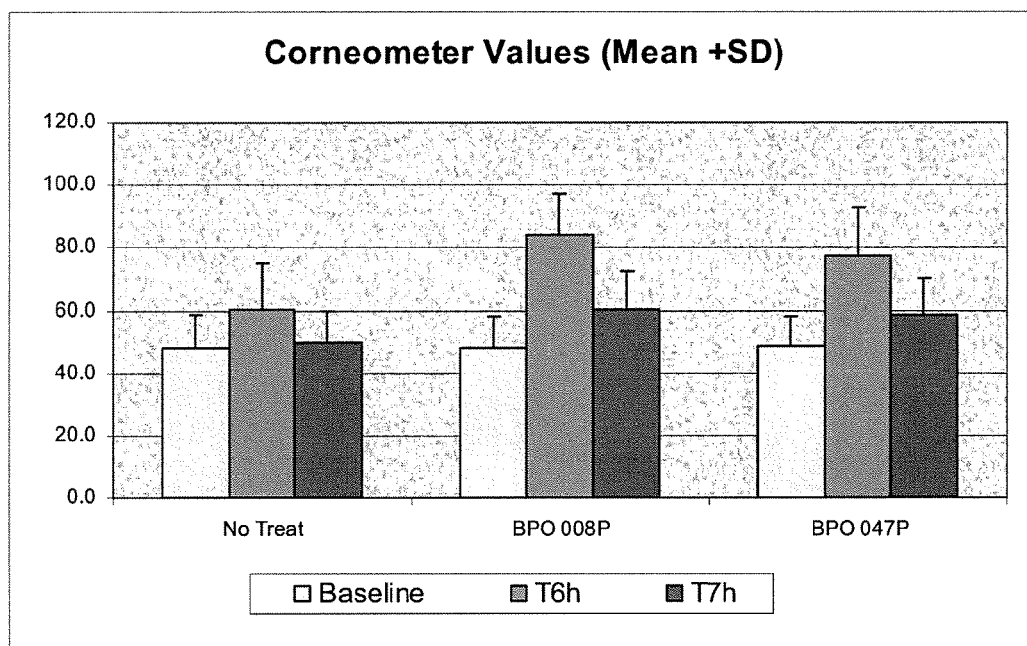
FIG. 7 shows Corneometer average values after treatment of skin using foamable compositions with and without carbomer.

Conclusions:

Based on the study results (see FIGS. 6 and 7), no major hydration difference was observed between the two formulations. The formulation without carbomer was slightly better at 6 hours. Almost no difference was observed at seven hours. Both formulations increased the hydration of the skin and maintained it significantly higher compared to the control following six and seven hours. One hour after the skin was washed, the hydration effects of the formulations remained higher than controls. Note: Formulation 008 hydration was also previously observed in Example 16. Formulation 008P was presented in Example 15 and formulation 047 with BPO was presented in Example 23, which similar to the placebo formulation used herein except that in the placebo BPO is replaced by water. Both formulations are comprised of polymeric agents, Methocel and Xanthan, however 047 employs lower concentrations and carbopol 047 was added.

Procedure for 047 Describes in Example 18

Procedure (for BPO008):
Step 1: Preparation of Water Phase (B)
1.1. Heat part of water to 90° C., Add Methocel K100M with vigorous agitation until thoroughly wetted and evenly dispersed, no clumps are detected. Cool the rest of water. Add the hot water to the cool water while mixing until homogeneous and no particles are observed. The temperature should not exceed 10-15° C.
1.2 Heat to 50° C., add Xanthan gum with vigorous mixing. Keep temperature at 70.
1.3 Add all other water phase ingredients and heat to 70° C. to obtain complete dissolution of all ingredients.
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool the emulsion to 40° C.
Step 4: Glycerin, Sodium PCA and buffer addition
4.1. Add glycerin and sodium PCA to the emulsion while mixing thoroughly.
4.2. Cool to RT and not more then 30° C.
4.3. Add Citric acid and sodium citrate tribasic dihydrate to the water and mix.
Step 5: Homogenization
5.1. Add Benzoyl peroxide and homogenize for 15 minutes while cooling with ice bath.
Step 6: pH adjustment
6.1. Verify temperature emulsion is less than 30° C. Check pH, to obtain a pH of 4.5±0.2.
6.2. add water if necessary to obtain the correct weight.
Step 7: Canisters Filling and Crimping
Fill canister with PFF and crimped with valves
Step 8: Pressurizing
Canisters are filled with 8% propellant.

Example 21

Comparative Hydration Tests for BPO Formulation (BPO-047) with and w/o, Glycerin, with and w/o NaPCA and with a Combination Thereof Study protocol: See Examples 16 and 20. The procedure adopted is along the lines as described therein.

| STUDY ACTIVITY | Baseline* | 6 hours | 7 hours |
|---|---|---|---|
| Inclusion/exclusion criteria | x | | |
| Application of the test preparations | x | | |
| Assessment of skin hydration | | X | X |
| Assessment of tolerability parameters and Adverse Events | | X | X |

| Treatment ID | Treatment Name | Glycerin | NaPCA |
|---|---|---|---|
| A | BPO 047-A-081116P | N/A | 2.00 |
| B | BPO 047-B-081116P | 8.00 | N/A |
| C | BPO 047-C-081116P | 2.00 | 8.00 |
| D | BPO 047-D-081116P | 5.00 | 5.00 |
| E | BPO 047-E-081116P | 2.00 | 5.00 |
| F (reference) | BPO 047--081110P | 8.00 | 2.00 |
| G | No treatment | | |

Figure 8:
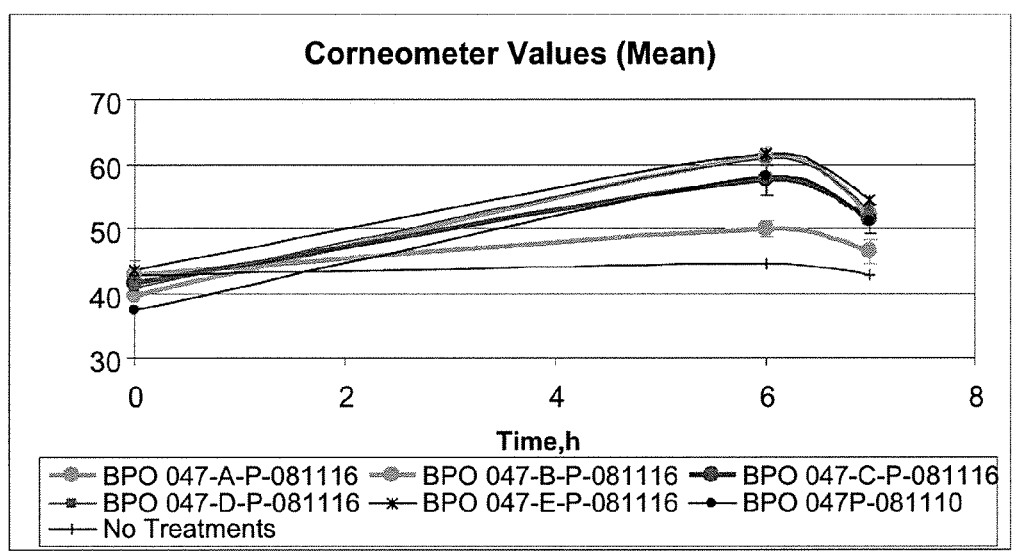
FIG. 8 shows Corneometer average values after treatment of skin using foamable compositions with various moisturizing complexes.
Figure 9:
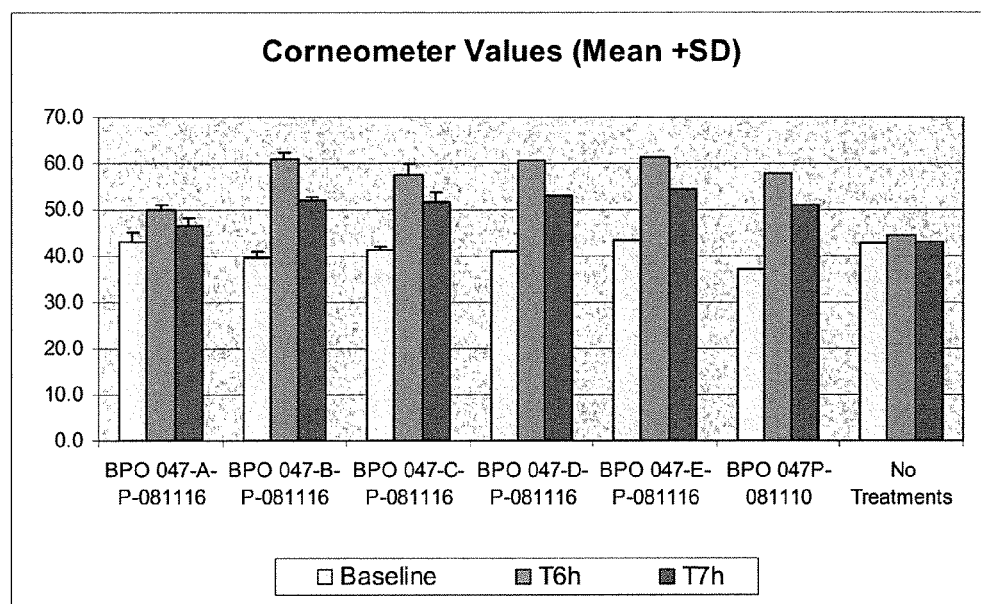
FIG. 9 shows Corneometer average values after treatment of skin using foamable compositions with various moisturizing complexes.
Figure 10:
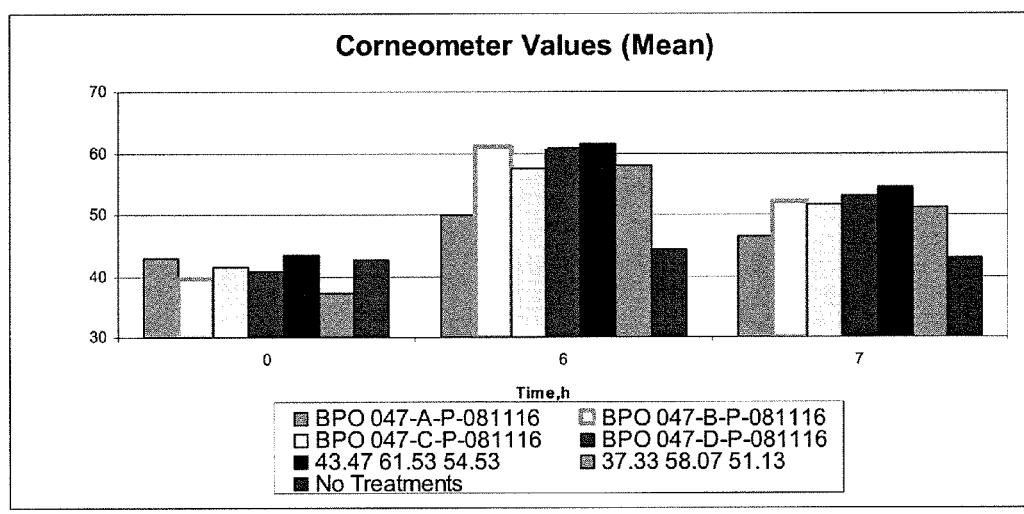
FIG. 10 shows Corneometer average values after treatment of skin using foamable compositions with various moisturizing complexes.
Figure 11:
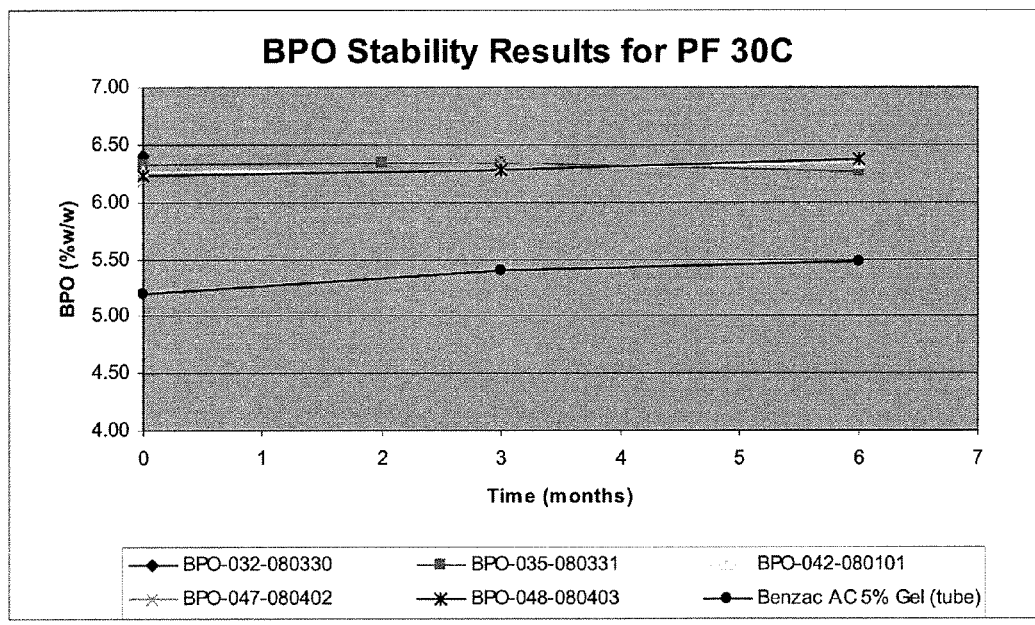
FIG. 11 shows stability measurements of BPO at 30 C.

Conclusions:

Based on the results shown in FIGS. 8-10, glycerin is a main contributor to the hydration effect. Sodium PCA at 2% also increases hydration but to a lesser extent compared to 8% glycerin. It may be that higher levels of sodium PCA improve hydration. Increasing sodium PCA at the account of glycerin also resulted in a similar level of improved hydration. It may be that at the combined levels of glycerin and sodium PCA in the presence of mineral oil hydration is maximized which may explain the minor differences between the results.

Example 22

Stability Studies Formulations and Results at and 30° C.

A six-month foam Chemical stability of BPO in 30° C.—in various formulations comparing to Benzac an existing BPO water based gel product comprising 5% BPO.

| | | Assay Results at 30° C. | | | | | |
|---|---|---|---|---|---|---|---|
| Formulation No. | T-0 | 2 month | % from T-0 | 3 month | % from T-0 | 6 month | % from T-0 |
| BPO-032-080330 | 6.40 | N/M* | 0.0 | N/M* | N/M* | N/M* | N/M* |
| BPO-035-080331 | 6.33 | 6.34 | 100.2 | 6.35 | 100.2 | 6.27 | 99.0 |
| BPO-042-080101 | 6.27 | N/M* | 0.0 | 6.28 | 100.1 | 6.33 | 101.1 |
| BPO-047-080402 | 6.18 | N/M* | 0.0 | 6.36 | 102.9 | 6.07 | 98.2 |
| BPO-048-080403 | 6.23 | N/M* | 0.0 | 6.27 | 100.8 | 6.37 | 102.4 |
| Benzac AC 5% Gel (tube) | 5.20 | N/M* | 0.0 | 5.40 | 103.8 | 5.47 | 105.2 |

*-N/M- not measured

Note: Benzac Ingredients: Benzoyl peroxide 5% in a water base gel. Non-medicinal ingredients: Acrylates copolymer, carbomer 940, docusate sodium, edetate disodium, glycerin, poloxamer 182, propylene glycol, purified water, silicon dioxide, and sodium hydroxide. May contain citric acid to adjust pH. Benzac is a gel BPO formulation currently on the market. BPO is in a gel and is not fluid.

Comments: BPO shows 6-month chemical stability in the different examples tested of the two types of formulations that have been developed at 30° C.: emollient (+6% oil) and mineral oil-free.

Example 23

A 6-Month Foam Physical Stability of BPO at 25° C. and at 30° C. with the Formulations Seen in Example 22

Part A—Formulation 032 (without Mineral Oil)

| Ingredients | BPO-032 |
|---|---|
| Cyclomethicone | 1.00 |
| PEG-40 Stearate | 3.00 |
| Polysorbate 60 | 1.00 |
| Glyceryl monostearate | 1.00 |
| Stearyl alcohol | 1.00 |
| Carbomer 934P (Carbopol 974P) | 0.35 |
| Hydroxypropyl methylcellulose (HPMC-Methocel K100M) | 0.27 |
| Xanthan gum | 0.27 |
| Citric acid | 0.38 |
| Sodium citrate tribasic dihydrate | 0.59 |
| Hydrous benzoyl peroxide | 6.00 |
| Trolamine | 0.18 |
| Purified water | to 100 |
| Propellant (AP-70) | 8.00 |

| Results | T-0 | T-2, 30° C. | T-2, 25° C. | T-6, 30° C. |
|---|---|---|---|---|
| Shakability | 2 | 1 | 1 | N/M* |
| Foam Quality | E | G | E | N/M* |
| Foam Color | white | white | white | N/M* |
| Foam Odor | no odor | v. f. odor | no odor | N/M* |
| Density (mg/ml) | 0.034 | 0.030 | 0.037 | N/M* |
| pH diluted (1:5) | 4.50 | 4.28 | 4.37 | N/M* |
| Collapse Time (sec) | >300 | >300 | >300/G | N/M* |
| Expansion Time (sec) | 50 | N/M* | N/M* | N/M* |

N/M*—not measured

Procedure (BPO032)

Step 1: Preparation of Water Phase (B)
1.4 Heat 70 g water to 70° C., add methocel with vigorous mixing until thoroughly wetted and evenly dispersed, no clumps are detected.
1.5 Add carbomer to water while mixing to dissolution and add base ("Carbomer solution"). In this formulation the base was trolamine. Heat carbomer solution to 50° C.
1.6 Add step 1.1 to step 1.2 and mix until no clumps are detected.
1.7 Adjust step 1.3 to 50° C. and add Xanthan gum with vigorous mixing
1.8 Heat step 1.4 to 70° C.
Step 2: Preparation of Phase A
2.2. Heat all ingredients of phase A to 70° C. until complete melting and homogeneity is obtained.
Step 3: Emulsification
3.5. Add phase A to the water phase at 65-70° C. with agitation
3.6. Agitation continues until PFF uniformity is reached.

3.7. Cool to RT and not more than 30° C.
3.8. Check pH.
Step 4: Buffer addition
4.5. Add Citric acid and sodium citrate tribasic dihydrate to 25 g water and mix.
4.6. Add step 4.1 to step 3 and mix.
4.7. Check pH.
4.8. Check the final weight of emulsion and add water if necessary to obtain the correct weight.
Step 5: Homogenization and Benzyl Peroxide addition
5.1. Start homogenization step 4 while cooling with ice bath. Add Benzoyl peroxide and keep homogenization for 60 minutes until uniformity and no agglomeration is seen in microscopic observation.
Step 6: pH adjustment
6.2. Verify temperature emulsion (from step 5) is less than 30° C. Check pH, to obtain a pH of 4.5±0.2.
Step 7: Canisters Filling and Crimping
Fill canister with PFF and crimped with valves
Step 8: Pressurizing
Canisters are filled with 8% propellant.

Part B—Formulation 035 (with Mineral Oil)

| Ingredients | BPO-035 |
|---|---|
| Mineral oil | 6.00 |
| Cyclomethicone | 1.00 |
| PEG-40 Stearate | 3.00 |
| Polysorbate 60 | 1.00 |
| Glyceryl monostearate | 1.00 |
| Stearyl alcohol | 1.00 |
| Carbomer 940 (Carbopol 980) | 0.30 |
| Crospovidone CL-M | 1.00 |
| Hydroxypropyl methylcellulose (HPMC-Methocel K100M) | 0.15 |
| Xanthan gum | 0.15 |
| Glycerin | 8.00 |
| Sodium PCA | 2.00 |
| Citric acid | 0.38 |
| Sodium citrate tribasic dihydrate | 0.59 |
| Hydrous benzoyl peroxide | 6.00 |
| Sodium hydroxide 18% solution | 0.30 |
| Purified water | to 100 |
| Propellant (AP-70) | 8.00 |

| Results | T-0 | T-2, 30° C. | T-2, 25° C. | T-6, 30° C. |
|---|---|---|---|---|
| Shakability | 2 | 1 | 1 | 2 |
| Foam Quality | G | G | E | G |
| Foam Color | white | white | white | white |
| Foam Odor | no odor | v. f. odor | no odor | v. f. odor |
| Density (mg/ml) | 0.038 | 0.032 | 0.035 | 0.038 |
| pH diluted (1:5) | 4.57 | 4.39 | 4.47 | 4.17 |
| Collapse Time (sec) | >300 | >300 | >300/G | >300 |
| Expansion Time (sec) | 48 | N/M* | N/M* | N/M* |

N/M*—not measured

Procedure (BPO035):
Step 1: Preparation of Water Phase (B)
1.1. Heat 50 g water to 70° C., add methocel with vigorous mixing until thoroughly wetted and evenly dispersed, no clumps are detected.
1.2. Add carbomer to water while mixing to dissolution and add base ("Carbomer solution"). Add carbomer solution and mix until thoroughly wetted and evenly dispersed, no clumps are detected
1.3. Cool step 1.2 to 50° C. and add Xanthan gum with vigorous mixing
1.4. Heat step 1.3 to 70° C.
1.5. Heat 100 g water to 70° C.
1.6. Add crospovidone to step 1.5 and mix.
1.7. Add step 1.6 to step 1.4 and mix.
Step 2: Preparation of Oil Phase (A)
2.1. Heat all ingredients of the oil phase to 70° C. until complete melting and homogeneity is obtained.
Step 3: Emulsification
3.1. Add the oil phase to the water phase at 65-70° C. with agitation
3.2. Agitation continues until PFF uniformity is reached.
3.3. Cool the emulsion to RT and not more than 40° C.
3.4. Add glycerin and sodium PCA to the emulsion while mixing thoroughly.
3.5. Cool to RT and not more than 30° C.
3.6. Check pH.
Step 4: Buffer addition
4.1. Add Citric acid and sodium citrate tribasic dihydrate to 18 g water and mix.
4.2. Add step 4.1 to step 3 and mix.
4.3. Check pH.
4.4. Check the final weight of emulsion and add water if necessary to obtain the correct weight.
Step 5: Homogenization and Benzyl Peroxide addition
5.1. Start homogenization step 4 while cooling with ice bath. Add Benzoyl peroxide and keep homogenization for 60 minutes until uniformity and no agglomeration is seen in microscopic observation.
Step 6: pH adjustment
6.1. Verify temperature emulsion (from step 5) is less than 30° C. Check pH, to obtain a pH of 4.5±0.2.
Step 7: Canisters Filling and Crimping
Fill canister with PFF and crimped with valves
Step 8: Pressurizing
Canisters are filled with 8% propellant.

Part C—Formulation 042 (without Mineral Oil)

| Ingredients | BPO-042 |
|---|---|
| Cyclomethicone | 1.00 |
| PEG-40 Stearate | 3.00 |
| Polysorbate 60 | 1.00 |
| Glyceryl monostearate | 1.00 |
| Stearyl alcohol | 1.00 |
| Carbomer 941 (Carbopol 981) | 0.20 |
| Crospovidone CL-M | 1.00 |
| Hydroxypropyl methylcellulose (HPMC-Methocel K100M) | 0.25 |
| Xanthan gum | 0.25 |
| Citric acid | 0.38 |
| Sodium citrate tribasic dihydrate | 0.59 |
| Hydrous benzoyl peroxide | 6.00 |
| Sodium hydroxide 18% solution | 0.20 |
| Purified water | to 100 |
| Propellant (AP-70) | 8.00 |

| Results | T-0 | T-2, 30° C. | T-2, 25° C. | T-6, 30° C. |
|---|---|---|---|---|
| Shakability | 2 | 1 | 1 | 1 |
| Foam Quality | E | G | E | G |
| Foam Color | white | white | white | white |
| Foam Odor | no odor | v. f. odor | no odor | strong |
| Density (mg/ml) | 0.04 | 0.03 | 0.04 | 0.04 |
| pH diluted (1:5) | 4.55 | 4.39 | 4.52 | 4.10 |
| Collapse Time (sec) | >300 | >300 | >300/G | >300 |
| Expansion Time (sec) | 68.00 | N/M* | N/M* | N/M* |

N/M*—not measured

Procedure (BPO042):
Step 1: Preparation of BPO paste (B)
1.1. Heat 50 g water to 90° C., Add Methocel K100M with vigorous agitation until thoroughly wetted and evenly dispersed, no clumps are detected. Cool to 10 to 15° C. while mixing until homogeneous and no particles are observed.
1.2. Add 4 g crospovidone to 10 g water and mix.
1.3. Add step 1.2 to step 1.1 and mix vigorously.
1.4. Start homogenization step 1.3 while cooling with ice bath. Add 31.76 g Benzoyl peroxide and keep homogenization for 60 minutes.
Step 2: Preparation of Water Phase (A)
2.1. Add carbomer to water while mixing to dissolution and add base ("Carbomer solution"). Add 118 g water to carbomer solution and heat to 50° C. while mixing vigorously.
2.2. Add Xanthan gum with vigorous mixing.
2.3. Heat step 2.2 to 70° C.
Step 3: Preparation of Oil Phase (A)
3.1. Heat all ingredients of the oil phase to 70° C. until complete melting and homogeneity is obtained.
Step 4: Emulsification
4.1. Add 0.6 g sodium hydroxide to 10 g purified water and mix
4.2. Add the oil phase (step 3) to the water phase (step 2) at 65-70° C. with agitation.
4.3. Add step 4.1 to step 4.2 and continue agitation until PFF uniformity is reached.
4.4. Cool the emulsion to RT and not more than 30° C.
4.5. Check pH.
4.6. add water if necessary to obtain the correct weight.
Step 5: BPO Paste Addition
5.1. Add 72.57 g of step 1.4 to the PFF (step 4) and mix for 30 min while cooling with ice bath. Check pH.
5.2. Add Citric acid and sodium citrate tribasic dihydrate to 15 g water and mix.
5.3. Add step 5.2 to step 5.1 and mix.
5.4. Check pH, If pH higher than 4.5, add citric acid while mixing to obtain a pH of 4.5±0.2.
Step 7: Canisters Filling and Crimping
Fill canister with PFF and crimped with valves
Step 8: Pressurizing
Canisters are filled with 8% propellant.

Part D—Formulation 047 (with Mineral Oil)

| Ingredients | BPO-047 |
|---|---|
| Mineral oil | 6.00 |
| Cyclomethicone | 1.00 |
| PEG-40 Stearate | 3.00 |
| Polysorbate 60 | 1.00 |
| Glyceryl monostearate | 1.00 |
| Stearyl alcohol | 1.00 |
| Carbomer 941 (Carbopol 981) | 0.30 |
| Hydroxypropyl methylcellulose (HPMC-Methocel K100M) | 0.20 |
| Xanthan gum | 0.20 |
| Glycerin | 8.00 |
| Sodium PCA | 2.00 |
| Citric acid | 0.38 |
| Sodium citrate tribasic dihydrate | 0.59 |
| Hydrous benzoyl peroxide | 6.00 |
| Sodium hydroxide 18% solution | 0.30 |
| Purified water | to 100 |
| Propellant (AP-70) | 8.00 |

| Results | T-0 | T-2, 30° C. | T-2, 25° C. | T-6, 30° C. |
|---|---|---|---|---|
| Shakability | 2 | 2 | 2 | 1 |
| Foam Quality | E | G | G | E |
| Foam Color | white | white | white | white |
| Foam Odor | no odor | no odor | no odor | strong |
| Density (mg/ml) | 0.04 | 0.03 | 0.04 | 0.04 |
| pH diluted (1:5) | 4.56 | 4.42 | 4.52 | 4.17 |
| Collapse Time (sec) | >300 | >300 | >300/G | >300 |
| Expansion Time (sec) | 68.00 | N/M* | N/M* | N/M* |

N/M*—not measured
Note
the Procedure for BPO047 is described in example 18

Part E—Formulation 048 (without Mineral Oil)

| Ingredients | BPO-048 |
|---|---|
| Cyclomethicone | 1.00 |
| PEG-40 Stearate | 3.00 |
| Polysorbate 60 | 1.00 |
| Glyceryl monostearate | 1.00 |
| Stearyl alcohol | 1.00 |
| Carbomer 940 (Carbopol 980) | 0.30 |
| Crospovidone CL-M | 1.00 |
| Hydroxypropyl methylcellulose (HPMC-Methocel K100M) | 0.20 |
| Xanthan gum | 0.20 |
| Glycerin | 8.00 |
| Sodium PCA | 2.00 |
| Citric acid | 0.38 |
| Sodium citrate tribasic dihydrate | 0.59 |
| Hydrous benzoyl peroxide | 6.00 |
| Sodium hydroxide 18% solution | 0.30 |
| Purified water | to 100 |
| Propellant (AP-70) | 8.00 |

| Results | T-0 | T-2, 30° C. | T-2, 25° C. | T-6, 30° C. |
|---|---|---|---|---|
| Shakability | 2 | 1 | 1 | 1 |
| Foam Quality | G+ | G | G | G |
| Foam Color | white | white | white | white |
| Foam Odor | no odor | v. f. odor | no odor | strong |
| Density (mg/ml) | 0.039 | 0.033 | 0.035 | 0.039 |
| pH diluted (1:5) | 4.58 | 4.46 | 4.57 | 4.19 |
| Collapse Time (sec) | >300 | >300 | >300/G | >300 |
| Expansion Time (sec) | 57 | — | — | — |

Procedure (BPO048):
Step 1: Preparation of Water Phase (B)
1.1. Heat 200 g water to 70° C., add methocel with vigorous mixing until thoroughly wetted and evenly dispersed, no clumps are detected.
1.2. Add carbomer to water while mixing to dissolution and add base ("Carbomer solution"). Add carbomer solution and mix until thoroughly wetted and evenly dispersed, no clumps are detected
1.3. Cool step 1.2 to 50° C. and add Xanthan gum with vigorous mixing
1.4. Heat step 1.3 to 70° C.
1.5. Heat 150 g water to 70° C.
1.6. Add crospovidone to step 1.5 and mix.
1.7. Add step 1.6 to step 1.4 and mix.
Step 2: Preparation of Oil Phase (A)
2.1. Heat all ingredients of the oil phase to 70° C. until complete melting and homogeneity is obtained.
Step 3: Emulsification
3.1. Add the oil phase (step 2) to the water phase (step 1) at 65-70° C. with agitation 3.2. Agitation continues until PFF uniformity is reached.
3.3. Cool the emulsion to RT and not more than 40° C.
3.4. Add glycerin and sodium PCA to the emulsion while mixing thoroughly.
3.5. Cool to RT and not more than 30° C.
3.6. Check pH.

Step 4: Buffer addition
4.1. Add Citric acid and sodium citrate tribasic dihydrate to 58 g water and mix.
4.2. Add step 4.1 to step 3 and mix.
4.3. Check pH.
4.4. Check the final weight of emulsion and add water if necessary to obtain the correct weight.

Comments: 6-month physical stability at 25° and at 30° C. can be seen for each of the different examples of the two types of formulations that have been developed emollient (+6% oil) and mineral oil-free.

Example 24

Viscosity and Physical Parameters Study

This example describes measurements with 8% pentane (to simulate viscosity of formulation in canister with propellant) and without 8% pentane for various formulations including a prior art formulation.

Part A—Physical Results

| Formula name (test material type, closure system) | Viscosity of PFF (cPs) | Viscosity PFF + 8% penthane (cPs) | Viscosity ratio (%) (cPs) | Foam quality | Density | Bubble size (μm) | Collapse Time To |
|---|---|---|---|---|---|---|---|
| BPO-032(see Example 23) | 7454 | 7214 / 7086 | 96.78% / 95.06% | E | 0.034 | 74 | >300 |
| BPO-035 (see Example 23) | 5103 | 1462 | 28.64 | G | 0.038 | 86 | >300 |
| BPO-042 (see Example 23) | 5551 | 2615 | 47.12 | E | 0.040 | 63 | >300 |
| BPO-047-6(see Example 23) | 5855 | 4463 | 76.23 | E | 0.039 | 99 | >300 |
| BPO-048 (see Example 23) | 5471 | 2516 | 46.00 | G+ | 0.039 | 76 | >300 |
| BPO-047(1%) (see Example 18) | 1280 | 885 | 69.14 | E | N/M | N/M | N/M |
| BPO-047 (15%) (see Example 18) | 6559 | 6495 | 99.02 | E | N/M | N/M | N/M |
| BPO-049 (Example 3 US 2007/0003585) | 1045377 | 930601 | 89.02 | N/R | N/M | N/M | |
| BPO-035 (0.85% Carbopol 980) (See Part B) | 16764 | 9870 | 58.87 | E | N/M | N/M | N/M |
| BPO-035 (only 0.30% Carbopol 980) (See Part B) | 484 | 63 | 0.13 | G+ | N/M | 67 | N/M |
| BPO-051 (only 0.30% pemulen TR-2) (See Part B) | 895 | 797 | 89.05 | G | N/M | 122 | N/M |
| BPO-050 (only 0.30% xanthan gum)(See Part B) | 879 | 802 | 91.24 | G− | N/M | 149 | N/M |

N/M Not Measured;
Note:
The formulations are set out below in Part D below.

Step 5: Homogenization and Benzyl Peroxide addition
5.1. Start homogenization step 4 while cooling with ice bath. Add Benzoyl peroxide and keep homogenization for 60-90 minutes until uniformity and no agglomeration is seen in microscopic observation.
Step 6: pH adjustment
6.1. Verify temperature emulsion (from step 5) is less than 30° C. Check pH, to obtain a pH of 4.5±0.2.
Step 7: Canisters Filling and Crimping
Fill canister with PFF and crimped with valves
Step 8: Pressurizing
Canisters are filled with 8% propellant.

Comments: The pre-foam formulation viscosities are low for formulations with carbopol. Addition of simulated propellant results in some reduction of viscosity except where the concentration of BPO is very high (15%). The ratio (blue) varies from about 25% to 75% with one or two exceptions. The unexpected little or no change in viscosity on adding pentane may be a reflection of lack of solubility of pentane in the formulation. When the level of carbopol was increased nearly threefold from 0.3 to 0.85% the viscosity of the pre foam formulation on average approximately tripled. When the formulation Example 3 of US 2007/0003585 was prepared the viscosity was found to be in excess of 1 million cps. A comparison of low levels of carbopol, pemulen and xanthan disclosed that whilst all produced good quality foam the foam appearance using carbopol alone and likewise bubble size was slightly better than pemulen which in turn was slightly better than xanthan.

Part B

Polymer Test—Visual Inspection (Pressurized Glass Bottle)

a) Benzoyl Peroxide:

|  | T-0 | 6 M |
|---|---|---|
| BPO-032-080330* | Homogenous | Homogenous |
| BPO-035-080331 | Homogenous | Homogenous |
| BPO-042-080401 | Homogenous | Homogenous |
| BPO-047-080402 | Homogenous | Homogenous |
| BPO-048-080403 | Homogenous | Homogenous | b) Formulation:

|  | T-0 | 6 M |
|---|---|---|
| BPO-032-080330* | Homogenous | Creaming 90/10-reversible. |
| BPO-035-080331 | Homogenous | Creaming 90/10-reversible. |
| BPO-042-080401 | Homogenous | Creaming 85/15-reversible. |
| BPO-047-080402 | Homogenous | Creaming 90/10-reversible. |
| BPO-048-080403 | Homogenous | Creaming 80/20-reversible |

Note
in the markes cases *- BPO-032 was tested just to 3 month.

Comments: although the formulations showed a small amount of creaming which was reversible after six months the BPO remained homogenous and caking and sedimentation were not observed.

Part C

Figure 12:
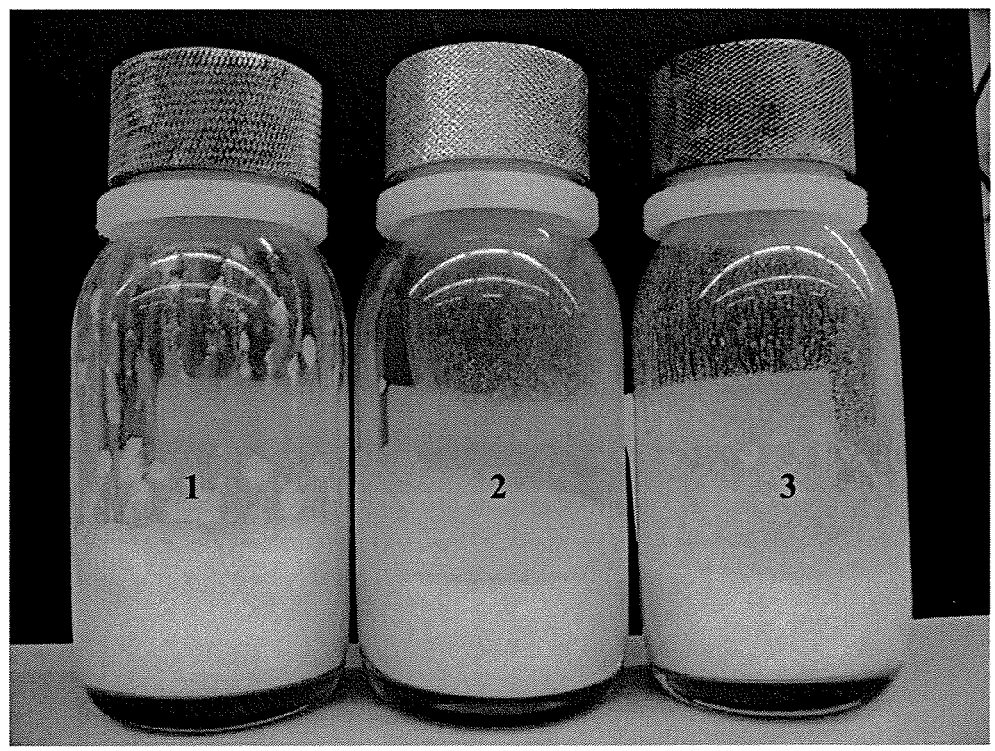
FIG. 12 shows formulations each comprising a different polymer.

Physical results (including Foam Quality) appear in example 24. See the photograph in FIG. 12. All three bottles represent formulation BPO035, but only with one polymer. In bottle #1 the polymer is Carbopol 980, 0.3% w/w. In bottle #2 the polymer is xanthan gum, 0.3% w/w. In bottle #1 the polymer is pemulen TR-2, 0.3% w/w.

Part D Formulations from Part A

Note

BPO-035-081123 (0.85% Carbopol 980)

| Ingredient name | % w/w |
|---|---|
| Mineral oil | 6.00 |
| Cyclomethicone | 1.00 |
| PEG-40 Stearate | 3.00 |
| Polysorbate 60 | 1.00 |
| Glyceryl monostearate | 1.00 |
| Stearyl alcohol | 1.00 |
| Hydroxypropyl methylcellulose | 0.15 |
| Xanthan gum | 0.15 |
| Purified water | 65.67 |
| Crospovidone | 1.00 |
| Carbopol 980 | 0.85 |
| NaOH 18% solution | 0.49 |
| Citric acid | 0.31 |
| Sodium citrate tribasic dihydrate | 0.44 |
| Glycerin | 8.00 |
| Sodium PCA | 2.00 |
| Benzoyl Peroxide | 7.94 |
| Control: | 100.00 |
| Propellant | 8.00 |

BPO-035-081124 (0.30% Carbopol 980)

| Ingredient name | % w/w |
|---|---|
| Mineral oil | 6.00 |
| Cyclomethicone | 1.00 |
| PEG-40 Stearate | 3.00 |
| Polysorbate 60 | 1.00 |
| Glyceryl monostearate | 1.00 |
| Stearyl alcohol | 1.00 |
| Purified water | 67.84 |
| Carbopol 980 | 0.30 |
| NaOH 18% solution | 0.17 |
| Citric acid | 0.31 |
| Sodium citrate tribasic dihydrate | 0.44 |
| Glycerin | 8.00 |
| Sodium PCA | 2.00 |
| Benzoyl Peroxide | 7.94 |
| Control: | 100.00 |
| Propellant | 8.00 |

BPO-051-081124 (0.30% Pemulen TR-21)

| Ingredient name | % w/w |
|---|---|
| Mineral oil | 6.00 |
| Cyclomethicone | 1.00 |
| PEG-40 Stearate | 3.00 |
| Polysorbate 60 | 1.00 |
| Glyceryl monostearate | 1.00 |
| Stearyl alcohol | 1.00 |
| Purified water | 67.84 |
| PemulenTR-2 | 0.30 |
| NaOH 18% solution | 0.17 |
| Citric acid | 0.31 |
| Sodium citrate tribasic dihydrate | 0.44 |
| Glycerin | 8.00 |
| Sodium PCA | 2.00 |
| Benzoyl Peroxide | 7.94 |
| Control: | 100.00 |
| Propellant | 8.00 |

BPO-050-081124 (0.30% Xanthan Gum)

| Ingredient name | % w/w |
|---|---|
| Mineral oil | 6.00 |
| Cyclomethicone | 1.00 |
| PEG-40 Stearate | 3.00 |
| Polysorbate 60 | 1.00 |
| Glyceryl monostearate | 1.00 |
| Stearyl alcohol | 1.00 |
| Purified water | 68.01 |
| Xanthan gum | 0.30 |
| Citric acid | 0.31 |
| Sodium citrate tribasic dihydrate | 0.44 |
| Glycerin | 8.00 |
| Sodium PCA | 2.00 |

-continued

| Ingredient name | % w/w |
|---|---|
| Benzoyl Peroxide | 7.94 |
| Control: | 100.00 |
| Propellant | 8.00 |

BPO-049-081123 (Stiefel Patent Application—Example 3)

| Ingredient name | % w/w |
|---|---|
| Water purified | 89.42 |
| Benzoyl peroxide hydrous | 2.84 |
| Clyndamycin phosphate | 1.28 |
| Tretinoin | 0.102 |
| Glycerin | 4.99 |
| Carbopol 980 | 0.84 |
| Sodium hydroxide (18% sol.)* | 0.49 |
| Methyl paraben | 0.04 |
| Total | 100.00 |

Example 25

Propellant Studies

In an initial study AP 70 was found to be preferred over AP 46. A visual foam quality comparison test between AP-70 and AP-46 was performed using BPO 014. The foam quality observed with AP-70 was slightly better.

In a further study formulation BPO042 was chosen as a representative example in which to examine the effects of different propellants.

Figure 13:
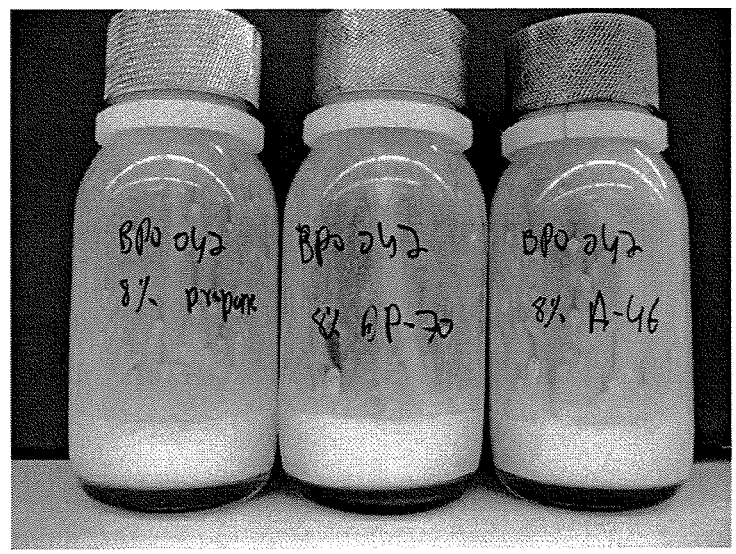
FIG. 13 shows formulations each comprising a different propellant.
Figure 14:
FIG. 14 shows formulations before and after addition of citrate buffer.

As shown in FIG. 13, 3 glass bottles were filled with 20 gr. PFF and 8% (1.6 gr.) different propellants: AP-70, AP-46 and Propane. All bottles were filled on Nov. 23, 2008. Photo was taken on Nov. 24, 2008
Comments:

As clearly demonstrates, after 24 hours at RT, all types of propellants showed similar behavior-stable and homogenous Example 26a Citrate Buffer Studies Procedure: 0.3 g Carbopol 980 was added to 67.84 g water with vigorous mixing until thoroughly wetted and evenly dispersed with no clumps detected. then, 0.17 g NaOH 18% solution was added (part of water phase BPO035). This combination produced the gel demonstrated in photographs #1 & 2 of FIG. 14. The final pH was 4.36. Then, Buffer was added (0.31 g citric acid and 0.44 g Sodium citrate) and the viscosity decreased dramatically, as demonstrated in photograph #3 of FIG. 14. The final pH was 4.13. Thus whilst the final pH of both the gel with NaOH and the liquid solution with the addition of citrate buffer was substantially identical the viscosity was radically and visually different. In the case of the whole emulsion formulation (BPO035) and the case of just the water phase of BPO035, the buffer was added at low temperature (25-30° C.).

Comments: Citrate buffer surprisingly destroys gel structure and significantly reduces formulation viscosity. Thus using citrate buffer with carbopol provides a significant advantage in that whilst viscosity appears low the polymer is unexpectedly able to hold the BPO suspension stable. Carbopol has a similar viscosity from pH=4 and way above, so these results are surprising.

Example 26b

Lactate Buffer Studies

Procedure: 0.3 gr. Carbopol 980 was added to 67.84 gr. water with vigorous mixing until thoroughly wetted and evenly dispersed with no clumps detected. then, 0.19 gr. NaOH 18% solution were added (part of water phase BPO035). This combination produced the gel demonstrated as demonstrate in "Citrate Buffer studies" The final pH was 4.75. Then, lactic acid (0.50 gr.) first and. then afterwards ammonium lactate (about 11 gr) were added for final pH 4.50. It was observed that the viscosity also decreased dramatically, upon addition of the acid and the formulation became fluid as demonstrated in FIG. 14 photograph #3 in "Citrate Buffer studies". It remained fluid after addition of ammonium lactate.

What is claimed is:

1. A foamable composition in an aerosol packaging assembly for treating skin comprising a prefoam emulsion composition and a liquefied or compressed gas propellant, the prefoam emulsion composition comprising:
   a)
      i) a suspended or entrapped active agent selected from the group consisting of benzoyl peroxide, imiquimod, acyclovir, zinc oxide, titanium oxide, an antibiotic, and a corticosteroid; or
      ii) an encapsulated or entrapped or suspended drug insoluble in the prefoam emulsion; and
   b) a carrier comprising:
      i) one or more surface-active agents;
      ii) about 0.01% to about 1% by weight of the emulsion composition of at least one pH sensitive polymeric additive comprising a polyacrylic acid polymer;
      iii) a hydrophobic solvent, wherein the hydrophobic solvent comprises at least 1% by weight of the emulsion composition of an oil;
      iv) water; and
      v) a buffer system, wherein up to about 2% by weight of the emulsion composition comprises the buffer system,
   wherein the buffer system is at a pH less than the pH of the prefoam emulsion before addition of the buffer system and is selected to provide a prefoam composition that is fluid at room temperature and that has a viscosity of less than about 8000 centipoises; wherein the liquefied or compressed gas propellant is at a concentration of about 3% to about 25% by weight of the foamable composition,
   wherein the pH sensitive polymeric additive is reversibly susceptible to buffer or pH adjuster, and the polymer together with the buffer system contributes to holding the active agent homogeneously dispersed in the foamable composition over a prolonged time,
   wherein the foamable composition is fluid at room temperature; and
   wherein the composition forms a breakable foam upon dispensing in which the active agent is homogenously dispersed.

2. The composition of claim 1, wherein the foam produced from the foamable composition has an average bubble size of less than about 150 microns; and/or wherein the foam produced has a density range between about 0.02 g/mL and about 0.1 g/mL.

3. The composition of claim 1, wherein the prefoam emulsion composition further comprises a pH adjusting component selected from the group consisting of a base and a buffer system, said pH adjusting component selected to be able to gel the polymeric additive.

4. The composition of claim 3, wherein the pH of the prefoam emulsion composition is between about 4.0 and about 6.0.

5. The composition of claim 4, wherein the buffer system is at a pH less than the pH of the prefoam emulsion before addition of the buffer and is selected to provide a liquid prefoam emulsion.

6. The composition of claim 1, wherein the buffer system is selected from the group consisting of citric acid, sodium citrate, lactic acid, ammonium lactate, and mixtures of any two or more thereof.

7. The composition of claim 1,
wherein the prefoam emulsion composition further comprises about 5% to about 30% by weight of a moisturizing complex comprising a moisturizing compound and a salt of 2-pyrrolidone-5-carboxylic acid (PCA),
wherein the hydrophobic solvent comprises mineral oil and a silicone oil,
wherein the prefoam emulsion composition improves the hydration of skin after 7 hours by at least about 20%.

8. The composition of claim 7, wherein the hydrophobic solvent is at a concentration from about 1% to about 15% by weight of the prefoam emulsion.

9. The foamable composition of claim 7, wherein the suspended or entrapped active agent/drug is benzoyl peroxide;
wherein the buffer system is selected to provide a prefoam composition that is fluid at room temperature, said prefoam composition having a viscosity of less than about 8000 centipoises; and
wherein the moisturizing complex enhances the stability of the foamable composition and/or reduces skin dryness or irritation associated with use of benzoyl peroxide.

10. The composition of claim 7, where the moisturizing complex comprises glycerin and a salt of PCA.

11. The composition of claim 7, wherein the prefoam emulsion composition comprises about 5% to about 15% by weight of the moisturizing complex.

12. The composition of claim 1, wherein the composition further comprises a phase-change polymer.

13. The composition of claim 1, wherein the one or more surface-active agents comprises between about 0.1% and about 5% by weight non ionic surface-active agents selected from the group consisting of steareth-21, steareth-2, steareth 20, polysorbate 80, polysorbate 60, polysorbate 20, ceteth 20, PEG 40-stearate, PEG 100-stearate, PEG-30 dipolyhydroxystearate, sorbitan stearate, sorbitan palmitate, sorbitan laurate, sorbitan monooleate, glyceryl stearate, laureth 4, ceteareth 20, macrogol cetostearyl ether, ceteth 2, sucrose distearate, polyoxyethylene (100) stearate, and mixtures of any two or more thereof.

14. The composition of claim 1, wherein the polymeric additive further comprises a polymeric agent selected from the group consisting of methylcellulose, hydroxypropyl cellulose, hydroxypropyl methylcellulose, hydroxyethyl cellulose, methylhydroxyethylcellulose, hydroxyethylcarboxymethylcellulose, carboxymethylcellulose, sodium carboxymethylcellulose, xanthan gum, guar gum, carrageenan gum, locust bean gum, tragacanth gum and mixtures of any two or more thereof.

15. The composition of claim 1, wherein the prefoam emulsion composition further comprises about 0.1% to about 5% by weight of a therapeutically active foam adjuvant selected from the group consisting of fatty alcohols having 15 or more carbons in their carbon chain; fatty acids having 16 or more carbons in their carbon chain; fatty alcohols derived from beeswax and including a mixture of alcohols, a majority of which has at least 20 carbon atoms in their carbon chain; fatty alcohols having at least one double bond; fatty acids having at least one double bond; branched fatty alcohols; branched fatty acids; fatty acids substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid and mixtures of any two or more thereof.

16. The composition of claim 1, wherein the prefoam emulsion composition further comprises at least one additional therapeutic agent selected from the group consisting of a steroidal anti-inflammatory agent, an immunosuppressive agent, an immunomodulator, an immunoregulating agent, a hormonal agent, an androgen, an estrogen, a prostaglandin, an antiandrogen agent, a testosterone inhibitor, a dihydrotestosterone inhibitor, an anti biotic agent, an antifungal agent, an antiviral agent, an antiparasitic agent, a retinoid, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, a keratolytic agent, urea, a urea derivative, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, an organo-metallic compound, an organo-boron compound, an organo-berrilium compound, talc, carbon, an anti wrinkle agent, a skin whitening agent, a skin protective agent, a masking agent, an anti-wart agent, a refatting agent, a lubricating agent and mixtures of any two or more thereof; and
wherein optionally the composition includes a stabilizing agent which acts as an effective barrier to a possible degradative interaction of the benzoyl peroxide and the at least one additional therapeutic agent.

17. The composition of claim 1, wherein the encapsulation or entrapping agent or particle is selected from the group comprising microsponges, polymer microspheres, zinc oxide, titanium oxide, silicone oxide and mixtures of any two or more thereof.

18. The composition of claim 1, further comprising a moisturizing complex, wherein the amount of hydrophobic solvent is about 1% to about 15% by weight of the prefoam emulsion composition.

19. The composition of claim 1, wherein the hydrophobic solvent is selected from the group consisting of a mineral oil, aliphatic, naphthalenic, and aromatic liquid hydrocarbons that derive from petroleum, a liquid oil originating from vegetable, marine or animal source, a saturated, unsaturated or polyunsaturated oil, a corn oil, a soybean oil, a canola oil, a cottonseed oil, a coconut oil, a sesame oil, a sunflower oil, a borage seed oil, a syzigium aromaticum oil, a hempseed oil, a herring oil, a cod-liver oil, a salmon oil, a flaxseed oil, a wheat germ oil, an evening primrose oil, a polyunsaturated oil containing poly-unsaturated fatty acids, omega-3 fatty acids, omega-6 fatty acids, linoleic acid, linolenic acid, gamma-linoleic acid (GLA), eicosapentaenoic acid (EPA), docosahexaenoic acid (DHA), an omega-3 oil, an omega-6 oil, a liquid hydrophobic plant-derived oil, a silicone oil, a non-volatile silicone, a polyalkyl siloxane, a polyaryl siloxane, a polyalkylaryl siloxane, a polyether siloxane copolymer, a polydimethylsiloxane, a dimethicone, a poly(dimethylsiloxane)-(diphenyl-siloxane) copolymer, a cyclic or linear polydimethylsiloxane containing from about 3 to about 9, or from about 4 to about 5, silicon atoms, a volatile silicone, acyclomethicone, and mixtures of any two or more thereof.

20. The composition of claim 1, wherein the prefoam emulsion composition comprises about 0.2% to about 0.85% by weight of the at least one pH sensitive polymeric additive.

21. The composition of claim 1, wherein the oil comprises a silicone oil.

22. The composition of claim 21, wherein the silicone oil is selected from a group consisting of a dimethicone, a cyclomethicone, a polyalkyl siloxane, a polyaryl siloxane, a polyalkylaryl siloxane, a polyether siloxane copolymer, a poly(dimethylsiloxane)-(diphenyl-siloxane) copolymer, and mixtures of any two or more thereof.

23. The composition of claim 1, wherein the amount of oil is about 1% to about 15% by weight of the emulsion composition.

24. The composition of claim 23, wherein the oil is selected from the group consisting of a mineral oil, a silicone oil, a jojoba oil, a MCT oil and mixtures of two or more thereof.

25. The composition of claim 24, wherein the surface-active agent comprises a combination of at least one non-ionic surfactant having HLB of less than 9 and at least one non-ionic surfactant having HLB of equal or more than 9.

26. The composition of claim 25, wherein the surface-active agent comprises at least two or more of a monoglyceride, a polyoxyethylene fatty acid ester, and a polysorbate.

27. The composition of claim 26, wherein the non-ionic surfactant having HLB of less than 9 and at least one non-ionic surfactant having HLB of equal or more than 9 are at a ratio of between 1:8 and 8:1, or at a ratio of 4:1 to 1:4.

28. The composition of claim 26, wherein the weighted average HLB of the combination of non-ionic surfactants is between about 5 and about 18.

29. The composition of claim 26, wherein the surface-active agent comprises two or more of glyceryl stearate, polysorbate 60 and PEG 40 stearate.

30. The composition of claim 1, wherein the prolonged time is at least two months.

31. The composition of claim 1, wherein the prolonged time is at least three months.

32. The composition of claim 1, wherein the prolonged time is at least six months.

33. A foamable composition in an aerosol packaging assembly comprising a prefoam emulsion composition and a liquefied or compressed gas propellant, the prefoam emulsion composition comprising:
  i. a suspended solid active agent;
  ii. one or more surface-active agents;
  iii. about 0.01% to about 1% by weight of the emulsion composition of at least one pH sensitive polymeric additive comprising a polyacrylic acid polymer;
  iv. about 5% to about 15% by weight of the emulsion composition of a moisturizing complex;
  v. a hydrophobic solvent;
  vi. water; and
  vii. a buffer system, wherein up to about 2% by weight of the emulsion composition comprises the buffer system,
  wherein the buffer system is at a pH less than the pH of the prefoam emulsion before addition of the buffer system and is selected to provide a prefoam composition that is fluid at room temperature, said prefoam composition having a viscosity of less than about 8000 centipoises (cps);
  wherein the pH sensitive polymeric additive is reversibly susceptible to buffer or pH adjuster, and the polymer together with the buffer system contributes to holding the active agent homogeneously dispersed in the foamable composition over a prolonged time,
  wherein the liquefied or compressed gas propellant is at a concentration of about 3% to about 25% by weight of the foamable composition;
  wherein the foamable composition is fluid at room temperature;
  wherein the suspended solid active agent has an average particle size of less than about 35 microns;
  wherein the composition further comprises at least one organic carrier selected from the group consisting of an organic polar solvent, an emollient and mixtures thereof, at a concentration of about 2% to about 50% by weight;
  wherein the at least one organic carrier comprises a penetration enhancer selected from the group consisting of propylene glycol, butylene glycols, hexylene glycol, glycerol, pentaerythritol, sorbitol, mannitol, oligosaccharides, dimethyl isosorbide, monooleate of ethoxylated glycerides having about 8 to 10 ethylene oxide units, polyethylene glycol 200-600, transcutol, glycofurol and cyclodextrins; and
  wherein the composition forms a breakable foam upon dispensing in which the active agent is homogenously dispersed.

34. The foamable composition of claim 33, wherein the polar solvent is about 1% to about 25% by weight of the emulsion composition and the polar solvent is selected from the group consisting of polyols, glycerol, propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, sulfoxides, dimethylsulfoxide, dimethylformanide, methyl dodecyl sulfoxide, dimethylacetamide, monooleates of ethoxylated glycerides with 8 to 10 ethylene oxide units, azone (1-dodecylazacycloheptan-2-one), 2-(n-nonyl)-1,3-dioxolane, isopropyl myristate, isopropyl palmitate, ethyl acetate, butyl acetate, methyl proprionate, capric/caprylic triglycerides, octylmyristate, dodecyl-myristate, lauryl alcohol, lauric acid, lauryl lactate, ketones, amides, acetamide oleates, triolein, alkanoic acids, caprylic acid, lactam compounds, alkanols, dialkylamino acetates, a polyethylene glycol, PEG 200, PEG 300, PEG 400, PEG600, PEG 4000, PEG 6000, PEG 10000 and mixtures of any two or more thereof.

35. The composition of claim 33, wherein the prefoam emulsion composition further comprises a pH adjusting component selected from the group consisting of a base and a buffer system, said pH adjusting component selected to be able to gel the polymeric additive.

36. A method of making the foamable composition of claim 35 comprising:

a) forming the prefoam emulsion comprising the active agent, the one or more surface-active agents; the at least one polymeric additive; the hydrophobic solvent; the pH adjusting component; the moisturizing complex; and the water, wherein the aqueous phase of the prefoam emulsion has a thickness sufficient to suspend the active agent;
b) adding the buffer system to the prefoam emulsion to reduce the viscosity of the prefoam emulsion; and
c) introducing the liquefied or compressed gas propellant to the prefoam emulsion to obtain a foamable composition having a stable suspended active solid and that is fluid at room temperature.

37. The method of claim 36, wherein the prefoam emulsion has a pH in the range from 4 to 6 or has a pH of less than about 5.

38. The method of claim 36, wherein the foamable composition forms a breakable foam upon dispensing in which the active agent is homogenously dispersed and wherein the foam produced from the foamable composition has an average bubble size of less than about 150 microns.

39. The method of claim 36, wherein the hydrophobic solvent is selected from the group consisting of a mineral oil, aliphatic, naphthalenic, and aromatic liquid hydrocarbons that derive from petroleum, a liquid oil originating from vegetable, marine or animal source, a saturated, unsaturated or polyunsaturated oil, a corn oil, a soybean oil, a canola oil, a cottonseed oil, a coconut oil, a sesame oil, a sunflower oil, a borage seed oil, a syzigium aromaticum oil, a hempseed oil, a herring oil, a cod-liver oil, a salmon oil, a flaxseed oil, a wheat germ oil, an evening primrose oil, a polyunsaturated oil containing poly-unsaturated fatty acids, omega-3 fatty acids, omega-6 fatty acids, linoleic acid, linolenic acid, gamma-linoleic acid (GLA), eicosapentaenoic acid (EPA), docosahexaenoic acid (DHA), an omega-3 oil, an omega-6 oil, a liquid hydrophobic plant-derived oil, a silicone oil, a non-volatile silicone, a polyalkyl siloxane, a polyaryl siloxane, a polyalkylaryl siloxane, a polyether siloxane copolymer, a polydimethylsiloxane, a dimethicone, a poly(dimethylsiloxane)-(diphenyl-siloxane) copolymer, a cyclic or linear polydimethylsiloxane containing from about 3 to about 9, or from about 4 to about 5, silicon atoms, a volatile silicone, acyclomethicone, and mixtures of any two or more thereof.

40. A method of treating a skin disorder, the method comprising administering a foam produced from a foamable composition of claim 1 topically onto the skin of a subject having said disorder.

* * * * *